(12) United States Patent
Perez et al.

(10) Patent No.: US 9,115,384 B2
(45) Date of Patent: *Aug. 25, 2015

(54) METHODS AND COMPOSITIONS FOR DETECTING RECEPTOR-LIGAND INTERACTIONS IN SINGLE CELLS

(75) Inventors: Omar D. Perez, San Francisco, CA (US); Garry P. Nolan, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/098,932

(22) Filed: May 2, 2011

(65) Prior Publication Data

US 2011/0207145 A1 Aug. 25, 2011

Related U.S. Application Data

(63) Continuation of application No. 12/551,333, filed on Aug. 31, 2009, which is a continuation of application No. 11/655,785, filed on Jan. 18, 2007, now Pat. No. 7,695,924, which is a continuation of application No.

(Continued)

(51) Int. Cl.
*G01N 33/68* (2006.01)
*C12Q 1/48* (2006.01)
(Continued)

(52) U.S. Cl.
CPC ............ *C12Q 1/485* (2013.01); *G01N 33/5008* (2013.01); *G01N 33/5041* (2013.01);
(Continued)

(58) Field of Classification Search
CPC .............. C12Q 1/485; G01N 33/5008; G01N 33/5041; G01N 33/5091; G01N 33/5094; G01N 33/56966; G01N 33/573; Y10S 435/973; Y10T 436/101666; Y10T 436/13; Y10T 436/25
USPC ................................... 435/7.1, 7.91
See application file for complete search history.

(56) References Cited

U.S. PATENT DOCUMENTS

| 4,469,863 A | 9/1984 | Ts'o et al. |
| 4,568,649 A | 2/1986 | Bertoglio-Matte |

(Continued)

FOREIGN PATENT DOCUMENTS

| JP | 2005-535328 A | 11/2005 |
| JP | 2008-501770 A | 1/2008 |

(Continued)

OTHER PUBLICATIONS

U.S. Appl. No. 13/094,735, filed Apr. 26, 2011, Perez et al.
(Continued)

*Primary Examiner* — Bao-Thuy L Nguyen
*Assistant Examiner* — Pensee Do
(74) *Attorney, Agent, or Firm* — Bret E. Field; Bozicevic, Field & Francis LLP

(57) ABSTRACT

The invention provides methods and compositions for simultaneously detecting the activation state of a plurality of proteins in single cells using flow cytometry. The invention further provides methods and compositions of screening for bioactive agents capable of coordinately modulating the activity of a plurality of proteins in single cells. The methods and compositions can be used to determine the protein activation profile of a cell for predicting or diagnosing a disease state, and for monitoring treatment of a disease state.

23 Claims, 21 Drawing Sheets

Related U.S. Application Data

10/346,620, filed on Jan. 16, 2003, now Pat. No. 7,381,535, which is a continuation-in-part of application No. 10/193,462, filed on Jul. 10, 2002, now Pat. No. 7,563,584.

(60) Provisional application No. 60/304,434, filed on Jul. 10, 2001, provisional application No. 60/310,141, filed on Aug. 2, 2001.

(51) Int. Cl.
    *G01N 33/50*     (2006.01)
    *G01N 33/569*     (2006.01)
    *G01N 33/573*     (2006.01)

(52) U.S. Cl.
    CPC ........ *G01N33/5091* (2013.01); *G01N 33/5094* (2013.01); *G01N 33/56966* (2013.01); *G01N 33/573* (2013.01); *Y10S 435/973* (2013.01); *Y10T 436/101666* (2015.01); *Y10T 436/13* (2015.01); *Y10T 436/25* (2015.01)

(56) References Cited

U.S. PATENT DOCUMENTS

| | | | |
|---|---|---|---|
| 4,979,824 | A | 12/1990 | Mathies et al. |
| 5,034,506 | A | 7/1991 | Summerton et al. |
| 5,137,809 | A | 8/1992 | Loken et al. |
| 5,216,141 | A | 6/1993 | Benner |
| 5,234,816 | A | 8/1993 | Terstappen |
| 5,235,033 | A | 8/1993 | Summerton et al. |
| 5,386,023 | A | 1/1995 | Sanghvi et al. |
| 5,599,681 | A | 2/1997 | Epstein et al. |
| 5,602,240 | A | 2/1997 | De Mesmaeker et al. |
| 5,637,684 | A | 6/1997 | Cook et al. |
| 5,644,048 | A | 7/1997 | Yau |
| 5,919,646 | A | 7/1999 | Okun et al. |
| 5,968,738 | A | 10/1999 | Anderson et al. |
| 5,998,212 | A | 12/1999 | Corio et al. |
| 6,248,550 | B1 | 6/2001 | Tsien et al. |
| 6,280,967 | B1 | 8/2001 | Ransom et al. |
| 6,379,917 | B1 | 4/2002 | Okun et al. |
| 6,495,333 | B1 | 12/2002 | Willmann et al. |
| 6,558,916 | B2 | 5/2003 | Veerapandian et al. |
| 6,592,822 | B1 | 7/2003 | Chandler |
| 6,673,554 | B1 | 1/2004 | Kauvar |
| 6,733,743 | B2 | 5/2004 | Jordan |
| 6,821,740 | B2 | 11/2004 | Darzynkiewicz et al. |
| 6,872,574 | B2 | 3/2005 | Cravatt et al. |
| 6,906,320 | B2 | 6/2005 | Sachs et al. |
| 6,958,221 | B2 | 10/2005 | Veerapandian et al. |
| 6,972,198 | B2 | 12/2005 | Craig et al. |
| 7,001,725 | B2 | 2/2006 | Singh et al. |
| 7,018,850 | B2 | 3/2006 | Raymond et al. |
| 7,070,943 | B2 | 7/2006 | Darzynkiewicz et al. |
| 7,102,005 | B2 | 9/2006 | Agnew et al. |
| 7,183,385 | B2 | 2/2007 | Comb et al. |
| 7,236,888 | B2 | 6/2007 | Allbritton et al. |
| 7,300,753 | B2 | 11/2007 | Rush et al. |
| 7,316,897 | B2 | 1/2008 | Bisconte de Saint Julien et al. |
| 7,326,577 | B2 | 2/2008 | Shults et al. |
| 7,351,546 | B2 | 4/2008 | Willmann et al. |
| 7,381,535 | B2 | 6/2008 | Perez et al. |
| 7,392,199 | B2 | 6/2008 | Karlov et al. |
| 7,393,656 | B2 | 7/2008 | Perez et al. |
| 7,419,777 | B2 | 9/2008 | Bacus |
| 7,563,584 | B2 | 7/2009 | Perez et al. |
| 7,695,924 | B2 | 4/2010 | Perez et al. |
| 7,695,926 | B2 | 4/2010 | Perez et al. |
| 7,939,278 | B2 | 5/2011 | Perez et al. |
| 7,939,331 | B2 | 5/2011 | Leite et al. |
| 8,187,885 | B2 | 5/2012 | Purvis, Jr. |
| 8,214,157 | B2 | 7/2012 | Moser et al. |
| 8,227,202 | B2 | 7/2012 | Fantl et al. |
| 8,242,248 | B2 | 8/2012 | Soper et al. |
| 8,394,599 | B2 | 3/2013 | Perez et al. |
| 2002/0028450 | A1* | 3/2002 | Greene et al. ..................... 435/6 |
| 2002/0127604 | A1 | 9/2002 | Albritton et al. |
| 2002/0177179 | A1 | 11/2002 | Glickman et al. |
| 2002/0197658 | A1 | 12/2002 | Delaney et al. |
| 2003/0148321 | A1 | 8/2003 | Pecker et al. |
| 2003/0190688 | A1 | 10/2003 | Crosby et al. |
| 2003/0190689 | A1 | 10/2003 | Crosby et al. |
| 2003/0203416 | A1 | 10/2003 | Staudt et al. |
| 2003/0219827 | A1 | 11/2003 | Comb et al. |
| 2003/0232364 | A1 | 12/2003 | Shaughnessy et al. |
| 2004/0063088 | A1 | 4/2004 | Berg et al. |
| 2004/0072184 | A1 | 4/2004 | Yoganathan et al. |
| 2004/0106156 | A1 | 6/2004 | Perez et al. |
| 2004/0126784 | A1 | 7/2004 | Hitoshi et al. |
| 2004/0137539 | A1 | 7/2004 | Bradford |
| 2004/0170995 | A1 | 9/2004 | Lograsso et al. |
| 2004/0180380 | A1 | 9/2004 | Lee et al. |
| 2004/0219592 | A1 | 11/2004 | Berg et al. |
| 2004/0224371 | A1 | 11/2004 | DeMatos et al. |
| 2004/0229284 | A1 | 11/2004 | Luciw et al. |
| 2004/0241636 | A1 | 12/2004 | Michnick et al. |
| 2004/0248151 | A1 | 12/2004 | Bacus et al. |
| 2005/0009112 | A1 | 1/2005 | Edgar et al. |
| 2005/0042694 | A1 | 2/2005 | Darzynkiewicz et al. |
| 2005/0074834 | A1 | 4/2005 | Chaplen et al. |
| 2005/0084924 | A1 | 4/2005 | Shults et al. |
| 2005/0131006 | A1 | 6/2005 | Mukherjee et al. |
| 2005/0216961 | A1 | 9/2005 | Delaney |
| 2005/0250127 | A1 | 11/2005 | Fisher et al. |
| 2005/0281743 | A1 | 12/2005 | Delaney |
| 2006/0029944 | A1 | 2/2006 | Huang et al. |
| 2006/0035211 | A1 | 2/2006 | Levinson et al. |
| 2006/0040338 | A1 | 2/2006 | Westwick et al. |
| 2006/0046249 | A1 | 3/2006 | Huang et al. |
| 2006/0046272 | A1 | 3/2006 | Chow et al. |
| 2006/0073474 | A1 | 4/2006 | Perez et al. |
| 2006/0216760 | A1 | 9/2006 | Dieterich et al. |
| 2007/0009923 | A1 | 1/2007 | Nolan et al. |
| 2007/0105165 | A1 | 5/2007 | Goolsby et al. |
| 2007/0196869 | A1 | 8/2007 | Perez et al. |
| 2008/0254489 | A1 | 10/2008 | Perez et al. |
| 2008/0274118 | A1 | 11/2008 | Aukerman et al. |
| 2009/0068681 | A1 | 3/2009 | Perez et al. |
| 2009/0081699 | A1 | 3/2009 | Perez et al. |
| 2009/0098594 | A1 | 4/2009 | Fantl et al. |
| 2009/0148462 | A1 | 6/2009 | Chevrier et al. |
| 2009/0269773 | A1 | 10/2009 | Fantl et al. |
| 2009/0269800 | A1 | 10/2009 | Covey et al. |
| 2009/0291458 | A1 | 11/2009 | Cohen et al. |
| 2010/0006787 | A1 | 1/2010 | Nakata et al. |
| 2010/0009364 | A1 | 1/2010 | Fantl et al. |
| 2010/0014741 | A1 | 1/2010 | Banville et al. |
| 2010/0030719 | A1 | 2/2010 | Covey et al. |
| 2010/0042351 | A1 | 2/2010 | Covey et al. |
| 2010/0086951 | A1 | 4/2010 | Hedley et al. |
| 2010/0099109 | A1 | 4/2010 | Fantl et al. |
| 2010/0105074 | A1 | 4/2010 | Covey et al. |
| 2010/0151472 | A1 | 6/2010 | Nolan et al. |
| 2010/0184092 | A1 | 7/2010 | Perez et al. |
| 2010/0204973 | A1 | 8/2010 | Parkinson et al. |
| 2010/0209929 | A1 | 8/2010 | Fantl et al. |
| 2010/0215644 | A1 | 8/2010 | Fantl et al. |
| 2010/0233733 | A1 | 9/2010 | Fantl et al. |
| 2010/0240542 | A1 | 9/2010 | Soper et al. |
| 2010/0285594 | A1 | 11/2010 | Purvis, Jr. |
| 2010/0297676 | A1 | 11/2010 | Fantl et al. |
| 2011/0020839 | A1 | 1/2011 | Perez et al. |
| 2011/0059861 | A1 | 3/2011 | Nolan et al. |
| 2011/0104717 | A1 | 5/2011 | Fantl et al. |
| 2011/0201018 | A1 | 8/2011 | Perez et al. |
| 2011/0201019 | A1 | 8/2011 | Perez et al. |
| 2011/0207146 | A1 | 8/2011 | Perez et al. |
| 2011/0207149 | A1 | 8/2011 | Perez et al. |
| 2011/0250614 | A1 | 10/2011 | Perez et al. |
| 2011/0262468 | A1 | 10/2011 | Fantl et al. |
| 2011/0269154 | A1 | 11/2011 | Fantl et al. |
| 2011/0269634 | A1 | 11/2011 | Perez et al. |
| 2012/0070849 | A1 | 3/2012 | Perez et al. |

(56) References Cited

U.S. PATENT DOCUMENTS

| | | | |
|---|---|---|---|
| 2012/0157340 A1 | 6/2012 | Cesano et al. | |
| 2012/0309026 A1 | 12/2012 | Perez et al. | |
| 2013/0071860 A1 | 3/2013 | Hale et al. | |
| 2013/0177970 A1 | 7/2013 | Perez et al. | |

FOREIGN PATENT DOCUMENTS

| | | | |
|---|---|---|---|
| JP | 2010-004750 A | 1/2010 | |
| WO | 99/44067 | 9/1999 | |
| WO | WO 99/44067 A1 | 9/1999 | |
| WO | 99/54494 | 10/1999 | |
| WO | WO 03/067210 A2 | 8/2003 | |
| WO | WO 03/067210 A3 | 12/2003 | |
| WO | WO 2006/012507 A2 | 2/2006 | |
| WO | WO 2006/012507 A3 | 10/2006 | |
| WO | WO 2007/056192 A2 | 5/2007 | |
| WO | WO 2007/056192 A3 | 7/2007 | |
| WO | 2011/031803 | 7/2008 | |
| WO | WO 2008/129296 A2 | 10/2008 | |
| WO | WO 2009/025847 A2 | 2/2009 | |
| WO | WO 2009/025847 A3 | 6/2009 | |
| WO | WO 2010/006291 A1 | 1/2010 | |
| WO | WO 2010/028277 A1 | 3/2010 | |
| WO | WO 2010/045651 A1 | 4/2010 | |
| WO | WO 2010/135608 A1 | 11/2010 | |

OTHER PUBLICATIONS

U.S. Appl. No. 13/094,737, filed Apr. 26, 2011, Perez et al.

U.S. Appl. No. 13/098,902, filed May 2, 2011, Perez et al.

Aziz, et al. Modulation of endothelial cell expression of ICAM-1, E-selectin, and VCAM-1 by beta-estradiol, progesterone, and dexamethasone. Cell Immunol. Jan. 10, 1996;167(1):79-85.

Benekli, et al. Signal transducer and activator of transcription proteins in leukemias. Blood. Apr. 15, 2003;101 (8):2940-54.

Khalidi, et al. The immunophenotype of adult acute myeloid leukemia: high frequency of lymphoid antigen expression and comparison of immunophenotype, French-American-British classification, and karyotypic abnormalities. Am J Clin Pathol. Feb. 1998;109(2):211-20.

Irish, et al. Single cell profiling of potentiated phospho-protein networks in cancer cells. Cell. Jul. 23, 2004;118 (2):217-28.

Solling, et al. Free light chains of immunoglobulins in serum from patients with leukaemias and multiple myeloma. Scand J Haematol. Apr. 1982;28(4):309-18.

U.S. Appl. No. 60/304,434, filed Jul. 10, 2001, Perez et al.

U.S. Appl. No. 60/310,141, filed Aug. 2, 2001, Nolan et al.

Allende, et al. A novel CD18 genomic deletion in a patient with severe leucocyte adhesion deficiency: a possible CD2/lymphocyte function-associated antigen-1 functional association in humans. Immunology. 2000; 99: 440-50.

Anderson, et al. Simultaneous fluorescence-activated cell sorter analysis of two distinct transcriptional elements within a single cell using engineered green fluorescent proteins. Proc Natl Acad Sci USA. 1996; 93: 8508-11.

Apperley, et al. Bone marrow transplantation for chronic myeloid leukaemia in first chronic phase: importance of a graft-versus-leukaemia effect. Br J Haematol. Jun. 1988;69(2):239-45.

Bagrintseva, et al. FLT3-ITD-TKD dual mutants associated with AML confer resistance to FLT3 PTK inhibitors and cytotoxic agents by overexpression of Bcl-x(L). Blood. May 1, 2005;105(9):3679-85.

Bartram, et al. Translocation of c-abl oncogene correlates with the presence of a Philadelphia chromosome in chronic myelocytic leukaemia. Nature. Nov. 17-23, 1983;306(5940):277-80.

Belloc, et al. Flow cytometry detection of caspase 3 activation in preapoptotic leukemic cells. Cytometry. Jun. 1 2000;40(2):151-60.

Bene, et al. Detection of receptor clustering by flow cytometric fluorescence anisotropy measurements. Cytometry. 2000; 40: 292-306.

Birkenkamp, et al. Regulation of constitutive STAT5 phosphorylation in acute myeloid leukemia blasts. Leukemia. 2001; 15(12):1923-31.

Bleijs, et al. A single amino acid in the cytoplasmic domain of the beta 2 integrin lymphocyte function-associated antigen-1 regulates avidity-dependent inside-out signaling. J Biol Chem. 2001; 276: 10338-46.

Cairo, et al. Contol of multivalent interactions by binding epitope density. J Am Chem Soc. 2002; 124(8): 1615-9.

Caligaris-Cappio, et al. Infrequent normal B lymphocytes express features of B-chronic lymphocytic leukemia. J Exp Med. Feb. 1, 1982;155(2):623-8.

Calo, et al. STAT proteins: from normal control of cellular events to tumorigenesis. J Cell Physiol. Nov. 2003;197(2):157-68.

Cantley, et al. Oncogenes and signal transduction. Cell. Jan. 25, 1991;64(2):281-302.

Castillo, et al. Proliferative response of mantle cell lymphoma cells stimulated by CD40 ligation and IL-4. Leukemia. Feb. 2000;14(2):292-8.

Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.

Chung, et al. The biology of Abl during hemopoietic stem cell differentiation and development. Oncogene. Apr. 6, 1995;10(7):1261-8.

Clark, et al. Regulation of human B-cell activation and adhesion. Annu Rev Immunol. 1991;9:97-127.

Cochran, et al. Receptor clustering and transmembrane signaling in T cells. TRENDS in Biochemical Sciences. 2001; 26(5): 304-10.

Colucci, et al. Redundant role of the Syk protein tyrosine kinase in muse NK cell differentiation. J Immunol. 1999; 163: 1769-74.

Countouriotis, et al. Cell surface antigen and molecular targeting in the treatment of hematologic malignancies. Stem Cells. 2002;20(3):215-29.

Crans-Vargas, et al. CREB as a prognostic marker in acute leukemia. Abstract. Blood. 2001; 98(11), part 1, p. 316a.

Czech, M. PIP3 and PIP2: Complex Roles at the Cell Surface. Cell, 2000; 100:603-606.

Damle, et al. Differential regulatory effects of intercellular adhesion molecule-1 on costimulation by CD28 counter-receptor B7. J Immunol. 1992; 149: 2541-8.

Dantuma, et al. Short-lived green fluorescent proteins for quantifying ubiquitin/proteasome-dependent proteolysis in living cells. Nat Biotechnol. 2000; 18: 538-43.

Davis, et al. Determination of CD4 antigen density on cells: role of antibody valency, avidity, clones, and conjugation. Cytometry. 1998; 33: 197-205.

De Fougerolles, et al. Characterization of ICAM-2 and evidence for a third counter-receptor for LFA-1. J Exp Med. 1991; 174: 253-67.

De Fougerolles, et al. Heterogenous glycosylation of ICAM-3 and lack of interaction with Mac-1 and p150,95. Eur J Immunol. 1995; 25: 1008-12.

De Rosa, et al. 11-color, 13-parameter flow cytometry: Identification of human naive T cells by phenotype, function, and T-cell receptor diversity. Nat Med. 2001; 7: 245-8.

Deeths, et al. ICAM-1 and B7-1 provide similar but distinct costimulation for CD8+ T cells, while CD4+ T cells are poorly costimulated by ICAM-1. Eur J Immunol. 1999; 29: 45-53.

Devine, et al. Role of LFA-1, ICAM-1, VLA4 and VCAM-1 in lymphocyte migration across retinal pigment epithelial monolayers in vitro. Immunology. 1996; 88: 456-62.

Di Bacco, et al. Molecular abnormalities in chronic myeloid leukemia: deregulation of cell growth and apoptosis. Oncologist. 2000;5(5):405-15.

Diacovo, et al. A functional integrin ligand on the surface of platelets: intercellular adhesion molecule-2. J Clin Invest. 1994; 94: 1243-51.

Dikic, et al. A role for Pyk2 and Src in linking G-protein-coupled receptors with MAP kinase activation. Nature. 1996; 383: 547-50.

Donskov, et al. Expression and function of LFA-1 on A-NK and T-LAK cells: role in tumor target killing and migration into tumor tissue. Nat Immun. 1996; 15: 134-46.

(56) References Cited

OTHER PUBLICATIONS

Erlanson, et al. Flow cytometric quantification of cyclin E in human cell lines and hematopoietic malignancies. Cytometry. Jul. 1, 1998;32(3):214-22.
European search report Jul. 10, 2006 for Application No. 02805693.5.
European search report and search opinion dated Feb. 22, 2011 for Application No. 10180167.8.
Fiering, et al. Improved FACS-Gal: flow cytometric analysis and sorting of viable eukaryotic cells expressing reporter gene constructs. Cytometry. 1991; 12: 291-301.
Fine, et al. The role of LFA-1/ICAM-1 interactions during murine T lymphocyte development. J Immunol. 1991; 147: 2852-9.
Friedman, et al. Bayesian network classifiers. Machine Learning. 1997; 29:131-163.
Friedman, et al. Inferring cellular networks using probabilistic graphical models. Science. Feb. 6, 2004;303(5659):799-805.
Friedman, et al. Using Bayesian networks to analyze expression data J Comput Biol. 2000;7(3-4):601-20.
Garrido, et al. Three-color versus four-color multiparameter cell cycle analyses of primary acute myeloid leukemia samples. Cytometry. Apr. 15, 2000;42(2):83-94.
Geiger, et al. Cytohesion-1 regulates beta-2 integrin-mediated adhesion through both ARF-GEF function and interaction with LFA-1. Embo J. 2000; 19: 2525-36.
Griffioen, et al. Endothelial intercellular adhesion molecule-1 expression is suppressed in human malignancies: the role of angiogenic factors. Cancer Res. 1996; 56: 1111-7.
Griffioen, et al. Tumor angiogenesis is accompanied by a decreased inflammatory response of tumor-associated endothelium. Blood. 1996; 88: 667-73.
Hamblin, et al. Unmutated Ig V(H) genes are associated with a more aggressive form of chronic lymphocytic leukemia. Blood. Sep. 15, 1999;94(6):1848-54.
Hartemink, et al. Using graphical models and genomic expression data to statistically validate models of genetic regulatory networks. Pac Symp Biocomput. 2001;:422-33.
Haswell, et al. Analysis of the oligomeric requirements for signaling by CD40 using soluble multimeric forms of its ligands, CD154. Eur J Immunol. 2001; 31(10): 3094-100.
Helander, et al. ICAM-2 redistributed by ezrin as a target for killer cells. Nature. 1996; 382: 265-8.
Hogg, et al. A novel leukocyte adhesion deficiency caused by expressed by nonfunctional beta2 integrins Mac-1 and LFA-1. J Clin Invest. 1999; 103: 97-106.
Hunter. Cooperation between oncogenes. Cell. Jan. 25, 1991;64(2):249-70.
Igietseme, et al. The intercellular adhesion molecule type-1 is required for rapid activation of T helped type 1 lymphocytes that control early acute phase of genital chlamydial infection of mice. Immunology. 1999; 98: 510-8.
International preliminary report on patentability dated May 5, 2008 for PCT Application No. US06/43050.
International search report Jul. 10, 2006 for PCT Application No. US2005/026026.
International Search Report dated Oct. 5, 2006 fro PCT Application No. US2006/002583.
International search report dated Oct. 15, 2003 fro PCT Application No. US02/22328.
International search report dated Oct. 15, 2009 for PCT Application No. No. US2008/000655.
International search report dated May 2, 2007 for PCT Application No. US06/43050.
International written opinion dated May 2, 2007 for PCT Application No. US06/43050.
Irish, et al. Mapping normal and cancer cell signalling networks: towards single-cell proteomics. Nat Rev Cancer. Feb. 2006;6(2):146-55.
Iyer, et al. Quantitation of CD38 expression using QuantiBRITE™ beads. Cytometry. 1998; 33: 206-12.

Jiang, et al. Pivotal role of phosphoinositide-3 kinase in regulation of cytotoxicity in natural killer cells. Nat Immunol. 2000; 1: 419-25.
Johnson, et al. Effector caspases are dispensable for the early nuclear morphological changes during chemical-induced apoptosis. J Cell Sci. 2000; 113: 2941-53.
Kennedy, et al. Akt/Protein kinase B inhibits cell death by preventing the release of cytochrome c from mitochondria. Mol Cell Biol. 1999; 19: 5800-10.
Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.
Kliche, et al. Signaling by human herpesvirus 8 kaposin A through direct membrane recruitment of cytohesin-1. Mol Cell. 2001; 7: 833-43.
Koester, et al. Intracellular markers. J Immunol Methods. Sep. 21, 2000;243(1-2):99-106.
Kornblau, et al. Dynamic single-cell network profiles in acute myelogenous leukemia are associated with patient response to standard induction therapy. Clin Cancer Res. Jul. 15, 2010;16(14):3721-33. (abstract).
Krutzik, et al. Analysis of protein phosphorylation and cellular signaling events by flow cytometry: techniques and clinical applications. Clinical Immunology. 2004; 110: 206-21.
Krutzik, et al. Intracellular phospho-protein staining techniques for flow cytometry: monitoring single cell singaling events. Cytometry Part A. 2003; 55A:61-70.
Kulik, et al. Antiapoptotic signaling by the insulin-like growth factor I receptor, phosphatidylinositol 3-kinase, and Akt. Mol Cell Biol. 1997; 17: 1595-606.
Lecoeur, et al. A novel flow cytometric assay for quantitation and multiparametric characterization of cell-mediated cytotoxicity. J Immunol Methods. 2001; 253: 177-87.
Lenkei, et al. Performance of calibration standards for antigen quantitation with flow cytometry. Cytometry. 1998; 33: 188-96.
Liu, et al. Overexpression of cyclin D1 in accelerated-phase chronic myeloid leukemia. Leuk Lymphoma. Dec. 2004;45(12):2419-25.
Lub, et al. Dual role of the actin cytoskeleton in regulating cell adhesion mediated by the integrin lymphocyte function-associated molecule-1. Mol Biol Cell. 1997; 8: 341-51.
Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].
Matsumoto, et al. Adhesion mediated by LFA-1 is required for efficient IL-12-induced NK and NKT cell cytotoxicity. Eur J Immunol. 2000; 30: 3723-31.
McDowall, et al. The I domain of integrin leukocyte function-associated antigen-1 is involved in a conformational change leading to high affinity binding to ligand intercellular adhesion molecule 1 (ICAM-1). J Biol Chem. 1998; 273: 27396-403.
Miller, et al. Intercellular adhesion molecule-1 dimerization and its consequences for adhesion mediated by lymphocyte function associated-1. J Exp Med. 1995; 182: 1231-41.
Morgan, et al. Cell-cycle-dependent activation of mitogen-activated protein kinase kinase (MEK-1/2) in myeloid leukemia cell lines and induction of growth inhibition and apoptosis by inhibitors of RAS signaling. Blood. Mar. 15, 2001;97(6):1823-34.
Morgan, et al. Superantigen-induced T cell:B cell conjugation is mediated by LFA-1 and required signaling though Lck, but not ZAP-70. J Immunol. 2001; 167: 5708-18.
Morkve, et al. Quantitation of biological tumor markers (p53, c-myc, Ki-67 and DNA ploidy) by multiparameter flow cytometry in non-small-cell lung cancer. Int J Cancer. Dec. 2, 1992;52(6):851-5.
Moser, et al. Improved outcome of chronic *Pseudomonas aeruginosa* lung infection associated with induction of a Th1-dominated cytokine response. Clin Exp Immunol. 2002; 127: 206-13.
Mukai, et al. Critical role of CD11a (LFA-1) in therapeutic efficacy of systemically transferred antitumor effector T cells. Cell Immunol. 1999; 192: 122-32.

(56) References Cited

OTHER PUBLICATIONS

Neben, et al. Gene expression patterns in acute myeloid leukemia correlate with centrosome aberrations and numerical chromosome changes. Oncogene. Mar. 25, 2004;23(13):2379-84.
Neeson, et al. Characterization of activated lymphocyte-tumor cell adhesion. J Leukoc Biol. 2000; 67: 847-55.
Nielsen, et al. Expression of the activation antigen CD69 predicts functionality of in vitro expanded peripheral blood mononuclear cells (PBMC) from healthy donors and HIV-infected patients. Clin Exp Immunol. 1998; 114: 66-72.
Nishimura, et al. Distinct role of antigen-specific T helper type 1 (Th1) and Th2 cells in tumor eradication in vivo. J Exp Med. 1999; 190: 617-27.
Nolan, et al. Fluorescence activated cell analysis and sorting of viable mammalian cells based on beta-D-galactosidase activity after transduction of *Escherichia coli* lacZ. Proc Natl Acad Sci USA. 1988; 85: 2603-7.
Norris. Multivariate analysis and reverse engineering of signal transduction pathways. Masters thesis. The University of British Columbia. Apr. 2002; pp. 152.
Nurse. Universal control mechanism regulating onset of M-phase. Nature. 1990; 344:503-508.
Olsen, et al. Function-based isolation of novel enzymes from a large library. Nat Biotechnol. 2000; 18: 1071-4.
Onishi, et al. Applications of retrovirus-mediated expression cloning. Exp Hematol. 1996; 24: 324-9.
Pallis, et al. Flow cytometric measurement of phosphorylated STAT5 in AML: lack of specific association with FLT3 internal tandem duplications. Leuk Res. Sep. 2003;27(9):803-5.
Pascual, et al. Analysis of somatic mutation in five B cell subsets of human tonsil. J Exp Med. Jul. 1, 1994;180(1):329-39.
Pe'er, et al. Inferring subnetworks from perturbed expression profiles. Bioinformatics. 2001;17 Suppl 1:S215-24.
Perez, et al. Activation of the PKB/AKT pathway by ICAM-2. Immunity. 2002; 16: 51-65.
Perez, et al. Flow cytometric analysis of kinase signaling cascades. Methods Mol Biol. 2004;263:67-94.
Perez, et al. Leukocyte functional antigen 1 lowers T cell activation thresholds and signaling through cytohesin-1 and Jun-activating binding protein 1. Nat Immunol. Nov. 2003;4(11):1083-92.
Perez, et al. LFA-1 signaling through p44/42 is coupled to perforin degranulation in CD56+CD8+ natural killer cells. Blood. Aug. 15, 2004;104(4):1083-93.
Perez, et al. Simultaneous measurement of multiple active kinase states using polychromatic flow cytometry. Nat Biotechnol. 2002; 20: 155-62.
Perfetto, et al. Seventeen-colour flow cytometry: unravelling the immune system. Nat Rev Immunol. Aug. 2004;4(8):648-55.
Peterson, et al. Coupling of the TCR to integrin activation by Slap-130/Fyb. Science. 2001; 293: 2263-5.
Pettersen, et al. CD47 signals T cell death. The American Association of Immunologists. 1999; 162: 7031-40.
Radoja, et al. CD8+ tumor-infiltrating T cells are deficient in perforin-mediated cytolytic activity due to defective microtubule-organizing center mobilization and lytic granule exocytosis. J Immunol. 2001; 167: 5042-51.
Rezaei, et al. Leukemia markers expression of peripheral blood vs bone marrow blasts using flow cytometry. Med Sci Monit. Aug. 2003;9(8):CR359-62.
Risso, et al. CD69 in resting and activated T lymphocytes. Its association with a GTP binding protein and biochemical requirements for its expression. J Immunol. 1991; 146: 4105-14.
Rosen, et al. Functional characterization of FLT3 receptor signaling deregulation in acute myeloid leukemia by single cell network profiling (SCNP). PLoS One. Oct. 27, 2010;5(10):e13543.
Sachs, et al. Analysis of signaling pathways in human T-cells using bayesian network modeling of single cell data Proceedings of the 2004 IEEE computational systems bioinformatics conferences. 2004; p. 644.
Sachs, et al. Bayesian network approach to cell signaling pathway modeling. Sci STKE. Sep. 3, 2002;2002(148):PE38.
Sachs, et al. Causal protein-signaling networks derived from multiparameter single-cell data. Science. Apr. 22, 2005;308(5721):523-9.
Salomon, et al. LFA-1 interaction with ICAM-1 and ICAM-2 regulates Th2 cytokine production. J Immunol. 1998; 161: 5138-42.
Scharffetter-Kochanek, et al. Spontaneous skin ulceration and defective T cell function in CD18 null mice. J Exp Med. 1998; 188: 119-31.
Schlessinger, et al. Growth factor signaling by receptor tyrosine kinases. Neuron. Sep. 1992;9(3):383-91.
Shankar, et al. CREB is amplified in AML blasts and is associated with an increased risk of relapse and decreased event-free survival. Abstract. Blood. 2004; 104(11), Part 1, p. 166A.
Shankar, et al. Role of cyclic AMP response element binding protein in human leukemias. Cancer. Nov. 1, 2005;104(9):1819-24.
Shankar, et al. The role of CREB as a proto-oncogene in hematopoiesis and in acute myeloid leukemia. Cancer Cell. Apr. 2005;7(4):351-62.
Shankaran, et al. IFNgamma and lymphocytes prevent primary tumour development and shape tumour immunogenicity. Nature. Apr. 26, 2001;410(6832):1107-11.
Shibuya, et al. Physical and functional association of LFA-1 with DNAM-1 adhesion molecule. Immunity. 1999; 11: 615-23.
Shier, et al. Defective CD8+ T cell activation and cytolytic function in the absence of LFA-1 cannot be restored by increased TCR signaling. J Immunol. 1999; 163: 4826-32.
Soede, et al. LFA-1 to LFA-1 signals invole zeta-associated protein-70 (ZAP-70) tyrosine kinase: relevance for invasion and migration of a T cell hybridoma. J Immunol. 1999; 163: 4253-61.
Somersalo, et al. Activation of natural killer cell migration by leukocyte integrin-binding peptide from intracellular adhesion molcule-2 (ICAM-2). J Biol Chem. 1995; 270: 8629-36.
Song, et al. Flow cytometry based biosensor for detection of multivalent proteins. Anal Biochem. 2000; 284: 35-41.
Spiekermann, et al. Overexpression and constitutive activation of FLT3 induces STAT5 activation in primary acute myeloid leukemia blast cells. Clinical Cancer Research. Jun. 2003; 9:2140-2150.
Staquet, et al. Expression of ICAM-3 on human epidermal dendritic cells. Immunobiology. 1995; 192: 249-61.
Starling, et al. Intercellular adhesion molecule-3 is the predominant co-stimulatory ligand for leukocyte function antigen-1 on human blood dendritic cells. Eur J Immunol. 1995; 25: 2528-32.
Sugai, et al. Allelic losses of 17p, 5q, and 18q loci in diploid and aneuploid populations of multiploid colorectal carcinomas. Hum Pathol. 2000; 31: 925-30.
Szegedi, et al. A new method to localize acid phosphatase using the confocal laser-scanning microscope. Pathol Oncol Res. 1998;4(3):217-23.
Tanaka, et al. Intercellular adhesion molecule 1 underlies the functional heterogeneity of synovial cells in patients with rheumatoid arthritis: involvement of cell cycle machinery. Arthritis Rheum. 2000; 43(11): 2513-22.
Taylor, et al. Complement-opsonized IgG antibody/dsDNA immune complexes bind to CR1 clusters on isolated human erythrocytes. Clinical Immunology and Immunopathology. 1991; 61: 143-60.
Trinchieri. Biology of natural killer cells. Adv Immunol. 1989;47:187-376.
UK office action and search report dated Feb. 22, 2011 for GB Application No. 1017857.2.
Weber, et al. Cytohesin-1 is a dynamic regulator of distinct LFA-1 functions in leukocyte arrest and transmigration triggered by chemokines. Curr Biol. 2001; 11: 1969-74.
Woolf, et al. Bayesian analysis of signaling networks governing embryonic stem cell fate decisions. Bioinformatics. Mar. 2005;21(6):741-53.
Yu, et al. IL-2 activation of NK cells: involvement of MKK1/2/ERK but not p38 kinase pathway. J Immunol. 2000; 164: 6244-51.
Zheng, et al. Regulation of STAT3 and STAT5 in the differentiation of FLT3/ITD expressing 32Dc13 cells induced by G-CSF and CEP-701. Abstract 2935.Blood. 2002; 100(11) and 44th Annual Meeting of the American Society of Hematology. Philadelphia, PA, USA. Dec. 6-10, 2002.

(56) References Cited

OTHER PUBLICATIONS

Zupo, et al. CD38 expression distinguishes two groups of B-cell chronic lymphocytic leukemias with different responses to anti-IgM antibodies and propensity to apoptosis. Blood. Aug. 15, 1996;88(4):1365-74.
Fiering, S. N. et al. "Improved FACS-gal:flow cytometric analysis and sorting of viable eukaryotic cells expressing reporter gene constructs." Cytometry, 12:291-301. (1991).
Fine, J. S., and Kruisbeek, A. M. (1991). "The role of LFA-1IICAM-1 interactions during murine T lymphocyte development." J Immunol 147. 2852-2859.
Geiger, C., et al. (2000). "Cytohesin-1 regulates beta-2 integrin-mediated adhesion through both ARF-GEF function and interaction with LFA-1." Embo J 19, 2525-2536.
Griffioen, A. W., et al. (1996). "Endothelial intercellular adhesion molecule-1 expression is suppressed in human malignancies: the role of angiogenic factors." Cancer Res 56,111 1-1 7.
Griffioen, A. W., et al. (1996). "Tumor angiogenesis is accompanied by a decreased inflammatory response of tumor-associated endothelium." Blood 88,667-73.
Haswell, L. E., et al., "Analysis of the oligomeric requirement for signaling by CD40 using soluble multimeric forms of its ligands, CD154", Eur. J. Immunol., 2001, 31(10):3094-3100.
Helander, T. S., et al. (1996). :ICAM-2 redistributed by ezrin as a target for killer cells. Nature 382, 265-8.
Hogg, N., et al. (1999). "A novel leukocyte adhesion deficiency caused by expressed but nonfunctional beta2 integrins Mac-1 and LFA-1." J Clin Invest 103, 97-106.
Igietseme, J. U., eta. (1999). "The intercellular adhesion molecule type-I is required for rapid activation of T helper type 1 lymphocytes that control early acute phase of genital chlamydia1 infection in mice." Immunology 98, 510-8.
Iyer, S. B., et al. (1998). "Quantitation of CD38 expression using QuantiBRITETM beads." Cytometry 33, 206-12.
Jiang, K., et al. (2000). "Pivotal role of phosphoinositide-3 kinase in regulation of cytotoxicity in natural killer cells." Nat Immunol 1, 419-425.
Johnson, V. L., et al. (2000). "Effector caspases are dispensable for the early nuclear morphological changes during chemical-induced apoptosis." J Cell Sci 11 3, 2941-53.
Kennedy, S. G., et al. (1999). "AktlProtein kinase B inhibits cell death by preventing the release of cytochrome c from mitochondria." Mol Cell Biol 19, 5800-10.
Kliche, S., et al. (2001). "Signaling by human herpesvirus 8 kaposin A through direct membrane recruitment of cytohesin-1." Mol Cell 7, 833-843.
Kulik, G., et al. (1997). "Antiapoptotic signalling by the insulin-like growth factor I receptor, phosphatidylinositol 3-kinase, and Akt." Mol Cell Biol 17,1595-606.
Lecoeur, H., et al. (2001). "A novel flow cytometric assay for quantitation and multiparametric characterization of cell-mediated cytotoxicity." J Immunol Methods 253, 177-1 87.
Lenkei, R., et al. (1998). "Performance of calibration standards for antigen quantitation with flow cytometry." Cytometry 33,188-96.
Lub, M., et al. (1997). "Dual role of the actin cytoskeleton in regulating cell adhesion mediated by the integrin lymohocvte function-associated molecule-I ." Mol Biol Cell 8, 341-351.
Matsumoto, G., et al. (2000). "Adhesion mediated by LFA-1 is required for efficient IL-12-induced NK and NKT cell cytotoxicity." Eur J Immunol 30, 3723-3731.
McDowall, A., et al. (1998). "The I domain of integrin leukocyte function-associated antigen-1 is involved in a conformational change leading to high affinity binding to ligand intercellular adhesion molecule 1 (ICAM-I)." J Biol Chem 273,27396-27403.
Miller, J., et al. (1995). "Intercellular adhesion molecule-1 dimerization and its consequences for adhesion mediated by lymphocyte function associated-1 ." J Exp Med 182, 1231-41.
Morgan, M. M., et al. (2001). "Superantigen-induced T cell:B cell conjugation is mediated by LFA-1 and requires sinnalinn through Lck, but not ZAP-70." J Immunol 167, 5708-5718.

Moser, C., et al. (2002). "Improved outcome of chronic *Pseudomonas aeruginosa* lung infection is associated with induction of a Thl-dominated cytokine response." Clin Exp Immunol 127, 206-213.
Mukai, S., et al. (1999). "Critical role of CDI I a (LFA-1) in therapeutic efficacy of systemically transferred antitumor effector T cells." Cell Immunol 192, 122-1 32.
Neeson, P. J., et al. (2000). "Characterization of activated lymphocyte-tumor cell adhesion." J Leukoc Biol 67, 847-855.
Nielsen, S. D., et al. "Expression of the activation antigen CD69 predicts functionality of in vitro expanded peripheral blood mononuclear cells (PBMC) from healthy donors and HIV-infected patients." Clin Exp Immunol 114, 66-72. (1 998).
Nishimura, T., et al. (1999). "Distinct role of antigen-specific T helper type 1 (Thl) and Th2 cells in tumor eradication in vivo." J Exp Med 190, 61 7-627.
Nolan, G. P., et al. "Fluorescence activated cell analysis and sorting of viable mammalian cells based on beta-D-galactosidase activitvafter transduction of *Escherichia coli* lacZ." Proc Natl Acad Sci U S A 85, 2603-7. (1988).
Olsen, M. J. et al. "Function-based isolation of novel enzymes from a large library." Nat Biotechnol 18,1071-4; (2000).
Onishi, M., et al. (1996). "Applications of retrovirus-mediated expression cloning." Exp Hematol 24,324-9.
Perez, 0. D., and Nolan, G. P. (2002). "Simultaneous measurement of multiple active kinase states using polychromatic flow cytometry." Nat Biotechnol 20, 155-1 62.
Perez, 0. D., eta;. (2002). "Activation of the PKBIAKT Pathway by ICAM-2." Immunity 26, 51-65.
Peterson, E. J., et al. (2001). "Coupling of the TCR to integrin activation by Slap-130IFyb." Science 293, 2263-2265.
Radoja, S., et al. (2001). "CD8+ tumor-infiltrating T cells are deficient in perforin-mediated cytolytic activity due to defective microtubule-organizing center mobilization and lytic granule exocytosis." J Immunol 167, 5042-5051.
Risso, A. et al. "CD69 in resting and activated T lymphocytes. Its association with a GTP binding protein and biochemical requirements for its expression." J Immunol 146, 41 05-14. (1991).
Salomon, B., and Bluestone, J. A. (1998). "LFA-1 interaction with ICAM-1 and ICAM-2 regulates Th2 cytokine production." J Immunol 161, 5138-5142.
Scharffetter-Kochanek, K., et al. (1998). "Spontaneous skin ulceration and defective T cell function in CD18 null mice." J Exp Med 188, 119-131.
Shibuya, K., et al. (1999). "Physical and functional association of LFA-1 with DNAM-1 adhesion molecule." Immunity 11, 615-623.
Shier, P., et al. (1999). "Defective CD8+ T cell activation and cytolytic function in the absence of LFA-1 cannot be restored by increased TCR signaling." J Immunol 163,4826-4832.
Soede, R. D., et al. (1999). "LFA-1 to LFA-1 signals involve zeta-associated protein-70 (ZAP-70) tyrosine kinase: relevance for invasion and migration of a T cell hybridoma." J Immunol 163,4253-4261.
Somersalo, K., et al. (1995). "Activation of natural killer cell migration by leukocyte integrin-binding peptide from intracellular adhesion molecule-2 (ICAM-2)." J Biol Chem 270, 8629-8636.
Song, X., et al. "Flow cytometry-based biosensor for detection of multivalent proteins." Anal Biochem 284, 35-41. (2000).
Staquet, M. J., et al. (1995). "Expression of ICAM-3 on human epidermal dendritic cells." Immunobiology 192, 249-61.
Starling, G. C., et al. (1995). "Intercellular adhesion molecule-3 is the predominant co-stimulatory ligand for leukocyte function antigen-I on human blood dendritic cells." Eur J Immunol25, 2528-2532.
Sugai, T., et al. (2000). "Allelic losses of 17p, 5q, and 18q loci in diploid and aneuploid populations of multiploid colorectal carcinomas." Hum Pathol 31, 925-30.
Tanaka Y, et al. "Intercellular adhesion molecule 1 underlies the functional heterogeneity of synovial cells in patients with rheumatoid arthritis: involvement of cell cycle machinery." Arthritis Rheum. Nov. 2000;43(11):2513-22.

(56) References Cited

OTHER PUBLICATIONS

Taylor, R.P., et al., "Complement-Opsonized IgG Antibody/dsDNA Immune Complexes Bind to CR1 Clusters on Isolated Human Erythrocytes", Clinical Immunology and Immunopathology, 1991, 61:143-160.
Weber, K. S., et al. (2001). "Cytohesin-I is a dynamic regulator of distinct LFA-1 functions in leukocyte arrest and transmigration triggered by chemokines." Curr Biol 11, 1969-1 974.
Yu, T. K., et al. (2000). "11-2 activation of NK cells: involvement of MKKIIZERK but not p38 kinase pathway." J Immunol 164, 6244-6251.
Krutzik et al. "Analysis of Protein Phosphorylation and Cellular Signaling Events by Flow Cytometry: Techniques and Clinical Applications," Clinical Immunology (2004) 110:206-221.
Pettersen et al. "CD47 Signals T Cell Death," The American Association of Immunologists (1999)—162:7031-7040.
Perez, Omar; et al., "Methods for the simultaneous determination of the activation state of multiple proteins", U.S. Appl. No. 60/304,434, filed Jul. 10, 2001.
Nolan, Garry; et al., "Methods for determining kinase activity", U.S. Appl. No. 60/310,141, filed Aug. 2, 2001.
Perez OD, Mitchell D, Jager GC, Nolan GP. LFA-1 signaling through p44/42 is coupled to perforin degranulation in CD56+CD8+ natural killer cells. Blood. Aug. 15, 2004;104(4):1083-93.
Perez OD, Krutzik PO, Nolan GP. Flow cytometric analysis of kinase signaling cascades. Methods in Molecular Biology. 2004;263:67-94.
Perez OD, Mitchell D, Jager GC, South S, Murriel C, McBride J, Herzenberg LA, Kinoshita S, Nolan GP. Leukocyte functional antigen 1 lowers T cell activation thresholds and signaling through cytohesin-1 and Jun-activating binding protein 1. Nature Immunology. Nov. 2003;4(11):1083-92.
Krutzik PO, Nolan GP. Intracellular phospho-protein staining techniques for flow cytometry: monitoring single cell signaling events. Cytometry (A). Oct. 2003;55(2):61-70.
Belloc; et al., "Flow Cytometry Detection of Caspase 3 Activation in Preapoptotic Leukemic Cells", Cytometry (2000), 40:151-160.
Demirovic, PIP3 and PIP2: Complex Roles at the Cell Surface, Cell (2000), 100:603-606.
De Rosa, Stephen C.; et al., "11-color, 13-parameter flow cytometry: Identification of human naive T cells by phenotype, function, and T-cell receptor diversity", Nature Medicine, Feb. 2001, 7(2): 245-8.
Koester; et al., Intracellular Markers, Journal of Immunological Methods, 2000, 243:99-106.
Krutzik, Peter O.; et al, "Intracellular phospho-protein staining techniques for flow cytometry: monitoring single cell signaling events", Cytometry (A), Oct. 2003, 55(2):61-70.
Morgan, Michael A.; et al., "Cell-cycle-dependent activation of mitogen-activated protein kinase kinase (MEK-1/2) in myeloid leukemia cell lines and induction of growth inhibition and apoptosis by inhibitors of RAS signaling", Neoplasia, Blood, Mar. 15, 2001, vol. 97, No. 6, pp. 1823-1834, The American Society of Hematology.
Perez, Omar D.; et al, "Leukocyte functional antigen 1 lowers T cell activation thresholds and signaling through cytohesin-1 and Jun-activating binding protein 1", Nature Immunology, Nov. 2003, 4(11):1083-92.
Perez, Omar D.; et al., "LFA-1 signaling through p44/42 is coupled to perforin degranulation in CD56+CD8+ natural killer cells", Blood, Aug. 15, 2004, 104(4):1083-93.
Perez, Omar D.; et al, "Flow cytometric analysis of kinase signaling cascades", Methods in Molecular Biology, 2004, 263:67-94.
Allende, L. M., et al., (2000). "A novel CD18 genomic deletion in a patient with severe leucocyte adhesion deficiency: a possible CD2Ilymphocyte function-associated antigen-1 functional association in humans." Immunology 991440-50.
Anderson, M. T. et al. "Simultaneous fluorescence-activated cell sorter analysis of two distinct transcriptional elements within a single cell using engineered green fluorescent proteins." Proc Natl Acad Sci U S A 93, 8508-11 (1996).

Bleijs, D. A., et al. (2001). "A single amino acid in the cytoplasmic domain of the beta 2 integrin lymphocyte function-associated antigen-1 regulates avidity-dependent inside-out signaling." J Biol Chem 276, 10338-1 0346.
Cairo, C.W., et al., "Control of Multivalent Interactions by Binding Epitope Density", J. Am. Chem. Soc., 2002, 124(8):1615-1619.
Cochran, J. R., et al., "Receptor clustering and transmembrane signaling in T cells", TRENDS in Biochemical Sciences, May 2001, 26(5):304-310.
Colucci, F., et al. (1999). "Redundant role of the Syk protein tyrosine kinase in mouse NK cell differentiation." J Immunol 163. 1769-17 74.
Damle, N. K., et al. (1992~)".D ifferential regulatory effects of intercellular adhesion molecule-1 on costimulation by the CD28 counter-receptor 87." J Immunol 149, 2541-2548.
Dantuma, N. P., et al. "Short-lived green fluorescent proteins for quantifying ubiquitin/proteasome-dependent proteolysis in living cells." Nat Biotechnol 18, 538-43. (2000).
Davis, K. A., et al. (1998). "Determination of CD4 antigen density on cells: role of antibody valency, avidity, clones, and conjugation." Cytometry 33,197-205.
De Fougerolles, A. R., et al. (1995). "Heterogenous glycosylation of ICAM-3 and lack of interaction with Mac-1 and p150,95." Eur J Immunol 25, 1008-12.
De Fougerolles, et al. (1991). "Characterization of ICAM-2 and evidence for a third counter-receptor for LFA-1." Exp Med 174. 253-67.
De Rosa, S. C., et al. "11-color, 13-parameter flow cytometry: Identification of human naive T cells by phenotype, function, and T-cell receptor diversity." Nat Med 7. 245-248. (2001 ).
Deeths, M. J., and Mescher, M. F. (1 999). "ICAM-1 and 87-1 provide similar but distinct costimulation for CD8+ T cells, while CD4+ T cells are poorly costimulated by ICAM-1." Eur J Immunol 29, 45-53.
Devine, L., et al. "Role of LFA-1, ICAM-1, VLA4 and VCAM-1 in lymphocyte migration across retinal pigment epithelial monolayers in vitro." Immunology 88, 456-62.
Diacovo, T. G., et al. (1994). "A functional integrin ligand on the surface of platelets: intercellular adhesion molecule-2." J Clin Invest 94,1243-51.
Dikic, I., et al. (1996). "A role for Pyk2 and Src in linking G-protein-coupled receptors with MAP kinase activation." Nature 383, 547-50.
Donskov, F., et al. (1996). "Expression and function of LFA-1 on A-NK and T-LAK cells: role in tumor target killing and migration into tumor tissue." Nat Immun 15, 134-146.
Wang; et al. "Regulation of Rb and E2F by signal transduction cascades: divergent effects of JNK1 and p38 kinases", The EMBO Journal (Mar. 1999), 18(6):1559-1570.
U.S. Appl. No. 13/453,636, filed Apr. 23, 2012, Purvis, Jr.
U.S. Appl. No. 13/464,254, filed May 4, 2012, Moser et al.
U.S. Appl. No. 13/473,829, filed May 17, 2012, Fantl et al.
U.S. Appl. No. 13/493,857, filed Jun. 11, 2012, Fantl et al.
U.S. Appl. No. 13/544,053, filed Jul. 9, 2012, Soper et al.
Amico, et al. Differential response of human acute myeloid leukemia cells to gemtuzumab ozogamicin in vitro: role of Chk1 and Chk2 phosphorylation and caspase 3. Blood. Jun. 1, 2003;101(11):4589-97.
Kumar, et al. 2-methoxyestradiol blocks cell-cycle progression at G(2)/M phase and inhibits growth of human prostate cancer cells. Mol Carcinog. Jul. 2001;31(3):111-24.
Mack, et al. Detection of caspase-activation in intact lymphoid cells using standard caspase substrates and inhibitors. J Immunol Methods. Jul. 31, 2000;241(1-2):19-31.
Benati; et al., "SRC family kinases as potential therapeutic targets for malignancies and immunological disorders", Curr Med Chern (2008), 15(12): 1154-1165.
Chow; et al., "Constitutive phosphorylation of the S6 ribosomal protein via mTOR and ERK signaling in the peripheral blasts of acute leukemia patients", Experimental hematology (2006), 34(9):1182-1190.
Cuenda; et al., "p38 MAP-kinases pathway regulation, function and role in human diseases", Biochimica et Biophysica Acta. (Aug. 2007), 1773(8):1358-1375.

(56) References Cited

OTHER PUBLICATIONS

Gualillo; et al.,"Leptin promotes the tyrosine phosphorylation of SHC proteins and SHC association with GRB2", Molecular and Cell Endocrinology (Apr. 2002), 190(1-2):83-89.

Hayakawa; et al.,"SFK-STAT pathway: an alternative and important way to malignancies", Ann. N.Y. Acad. Sci. (Nov. 2006), 1086:213-222.

Ingley; et al., "Src family kinases: regulation of their activities, levels and identification of new pathways", Biochimica et Biophysica Acta (Jan. 2008), 1784:56-65.

Kishimoto; et al., "Signal transduction through homo- or heterodimers of gp130", Stem Cells. 1994;12(Suppl):37-44; abstract only.

Krutzik; et al., "High-content single-cell drug screening with phosphospecific flow cytometry", Natural Chemical Biology (Feb. 2008). 4(2):132-142.

Neote; et al., "Molecular cloning, functional expression, and signaling characteristics of a C—C chemokine receptor", Cell. (Feb. 1993), 12;72(3):415-425.

Schulz; et al., "Single-cell phospho-protein analysis by flow cytometry", Curr Protoc Immunol (2007), Chapter 8:Unit 8.17.

Tanner; et al., "Multiplex bio-assay with inductively coupled plasma mass spectrometry: Towards a massively multivariate single-cell technology", Spectrochimia Acta Part B. (2007), 62(3):188-95.

Tefferi; et al., "JAK and MPL mutations in myeloid malignancies. Leuk Lymphoma", (Mar. 2008), 49(3):388-397.

Tse; et al., "Intracellular antibody capture technology: application to selection of intracellular antibodies recognising the BCR-ABL oncogenic protein", J Mol Biol. (Mar. 2002), 15;317(1):85-94.

Kinter et al., "The Common γ-Chain Cytokines IL-2, IL-7, IL-15, and IL-21 Induce the Expression of Programmed Death-1 and Its Ligands", J. Immunol., 2008, 181:6738-6746.

Fang; et al., "CGP57148B (STI-571) induces differentiation and apoptosis and sensitizes Bcr-Abl-positive human leukemia cells to apoptosis due to antileukemic drugs", Blood (Sep. 2000),96(6):2246-2253.

Office Action issued Apr. 15, 2015 in related Japanese Application No. 2012-555157, 12 pages.

Baines et al. "The MEK inhibitor, PD98059, reduces survival but does not block acute myeloid leukemia blast maturation in vitro", European Journal of Haematology, vol. 64, pp. 211-218 (2000).

Milella et al. "Therapeutic targeting of the MEK/MAPK signal transduction module in acute myeloid leukemia", Journal of Clinical Investigation, vol. 108, pp. 851-859 (2001).

Tse et al. "Inhibition of the transforming activity of FLT3 internal tandem duplication mutants from AML patients by a tyrosine kinase inhibitor", Leukemia, vol. 16, pp. 2027-2036 (2002).

Hagiwara; et al. "Tyrosine Phosphorylation of Proteins in Primary Human Myeloid Leukemic Cells Stimulated by Macrophage Colony-Stimulating Factor: Analysis by Disease Type and Comparison With Normal Human Hematopoietic Cells", Int J Hematol (Jan. 2007), 73(1)100-107.

Xu; et al. "Tandem duplication of the FLT3 gene is found in acute lymphoblastic leukaemia as well as acute myeloid leukaemia but not in myelodysplastic syndrome or juvenile chronic myelogenous leukaemia in children", Br J Haematol (Apr. 1999), 105(1):155-162 (abstract only).

Lunghi; et al. "Downmodulation of ERK activity inhibits the proliferation and induces the apoptosis of primary acute myelogenous leukemia blasts", Leukemia (Sep. 2003), 17(9):1783-1793.

\* cited by examiner

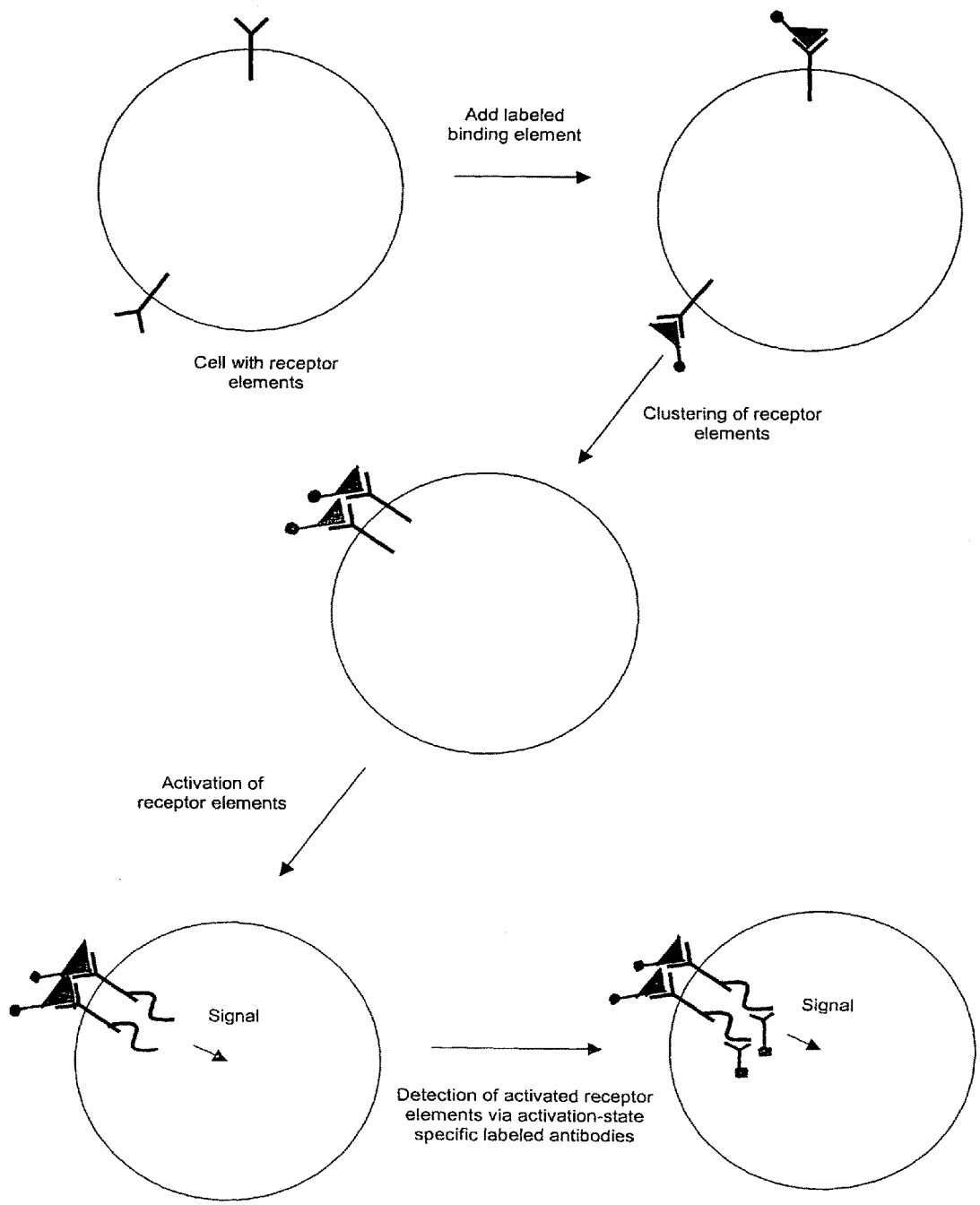
FIG_1

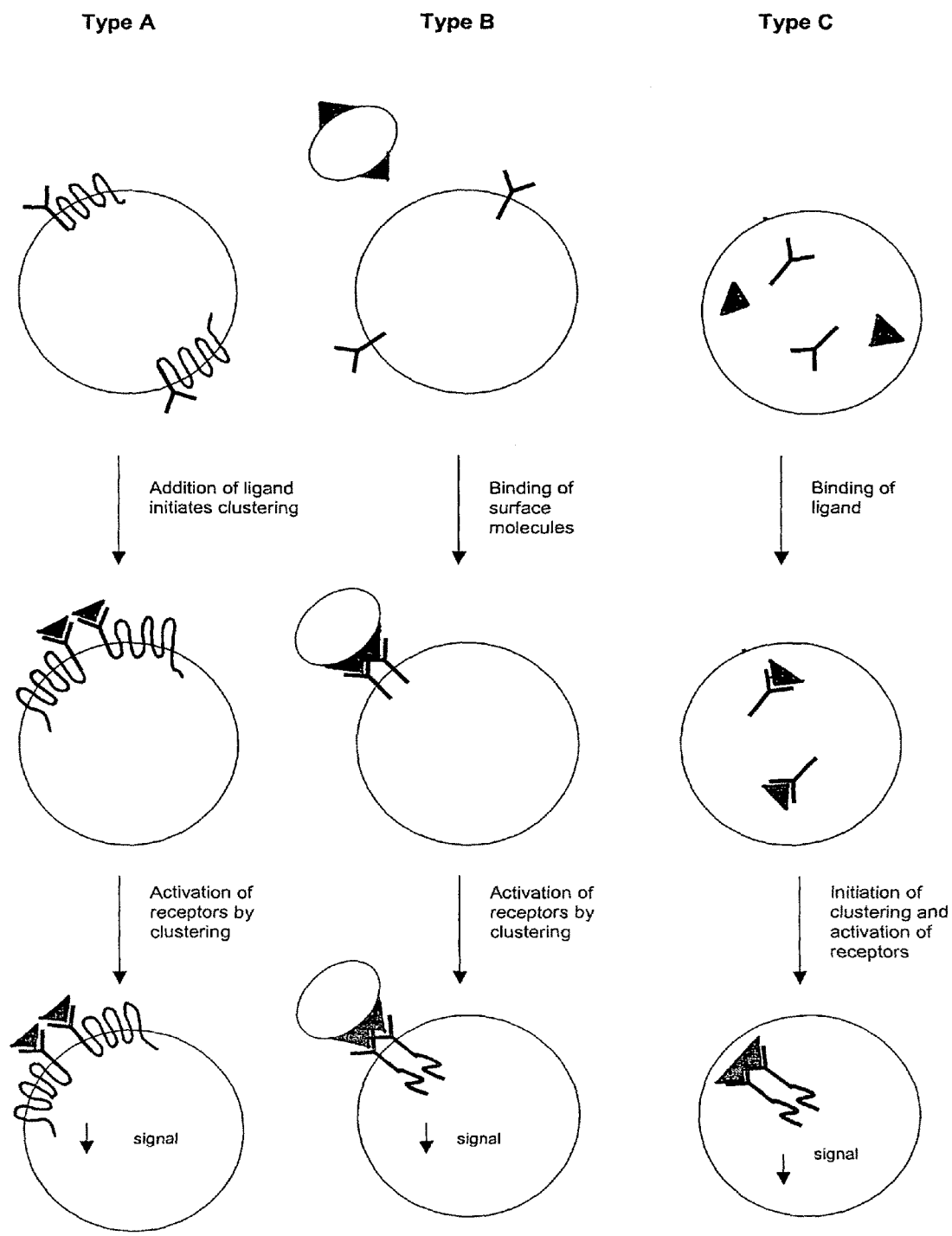
FIG_2

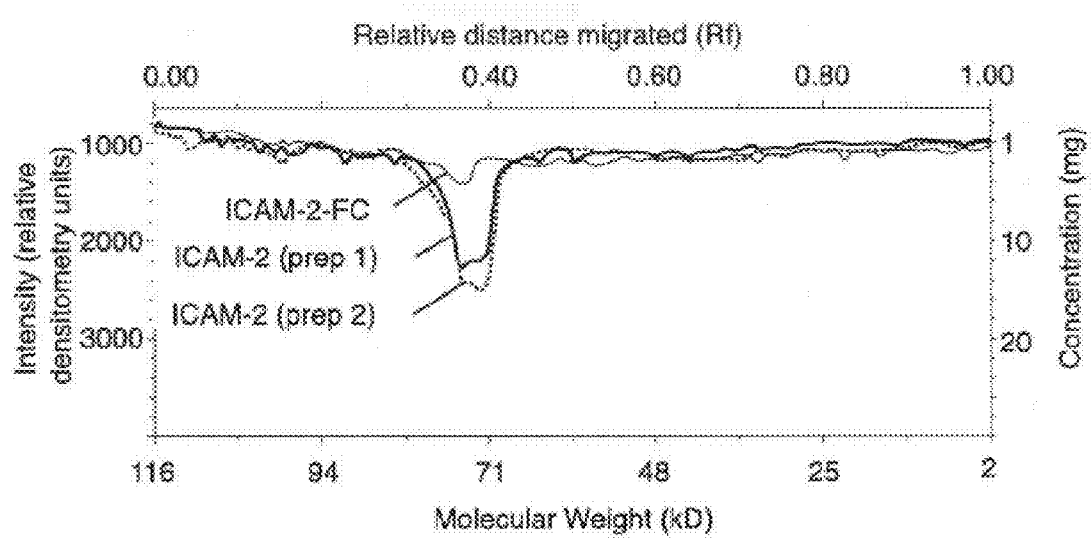
FIG_3A
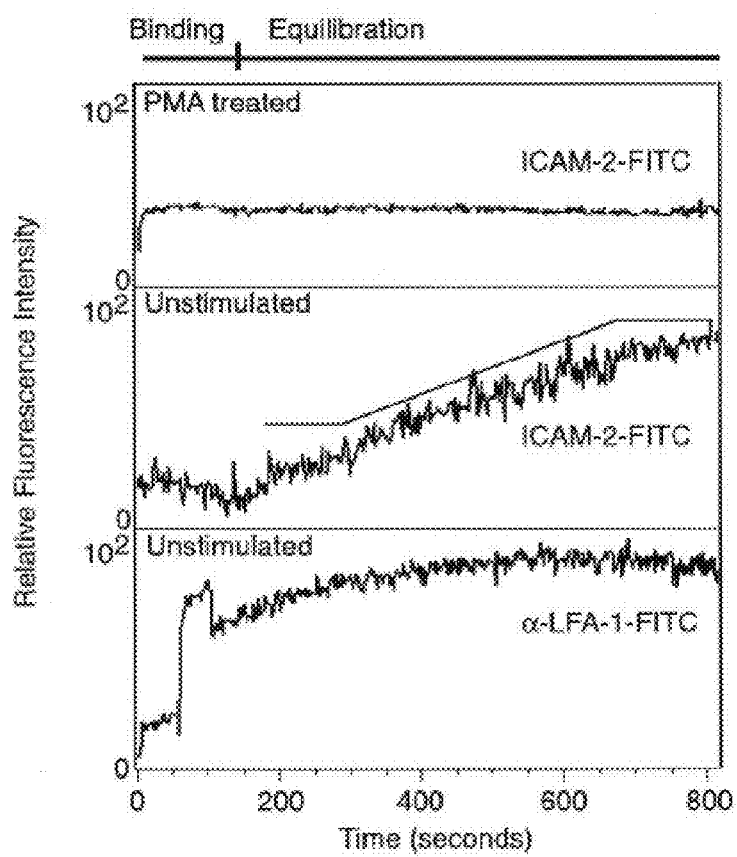
FIG_3B

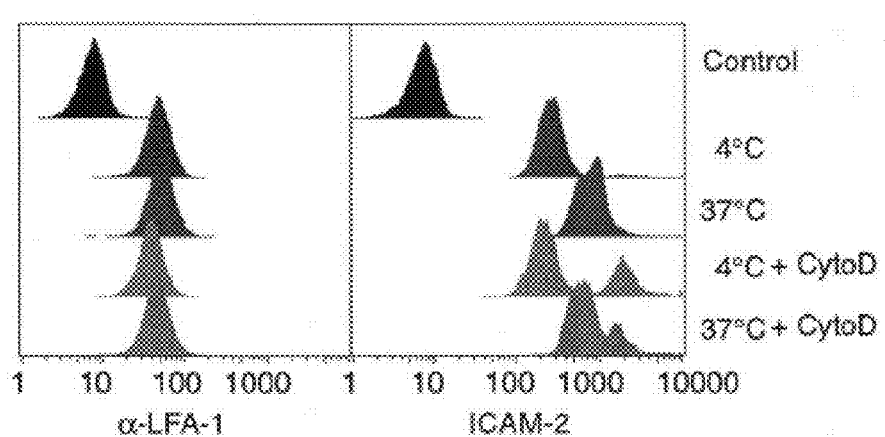
FIG_3C
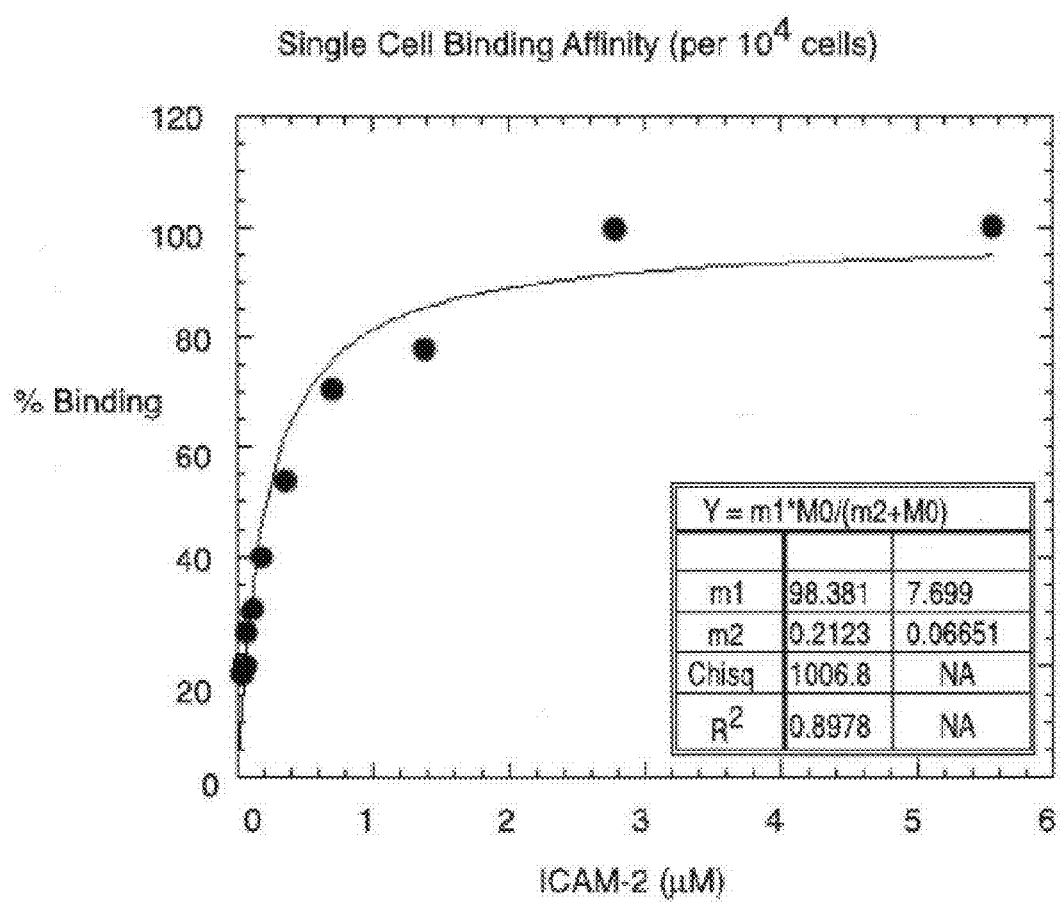
FIG_3D

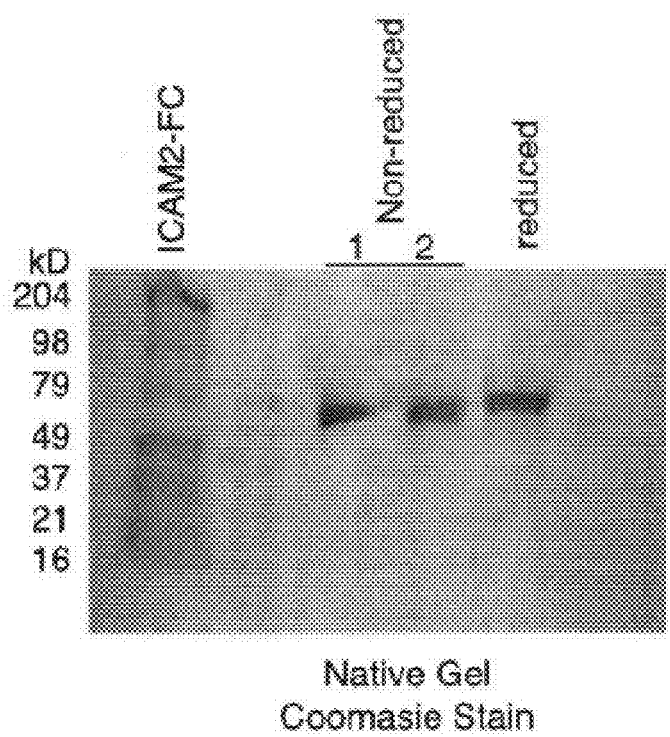
FIG_3E
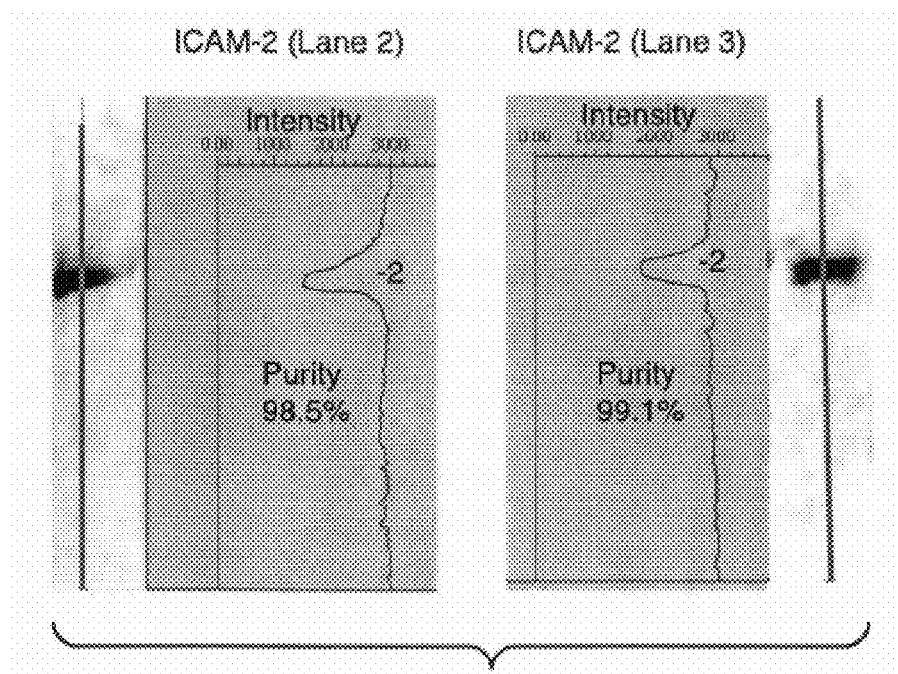
FIG_3F

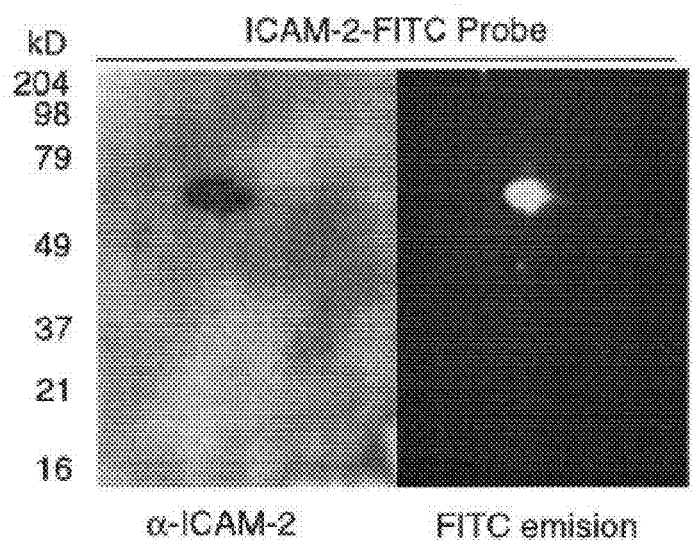
FIG_3G
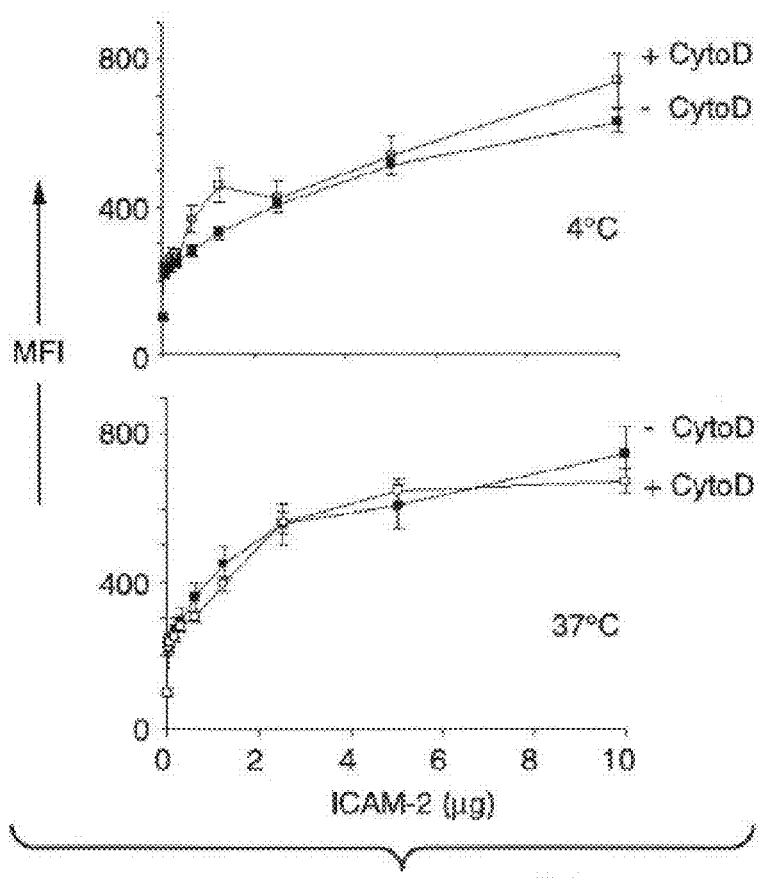
FIG_3H

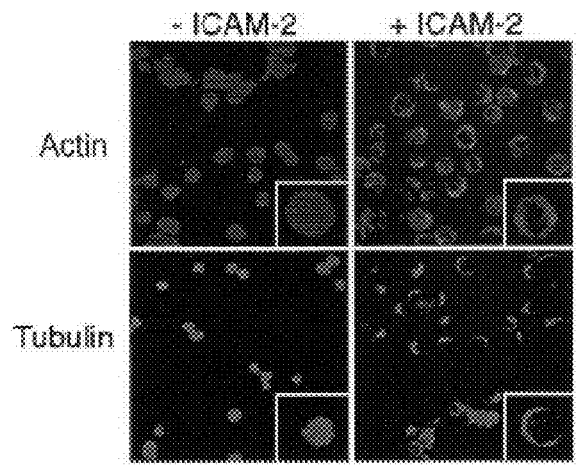
FIG_4A
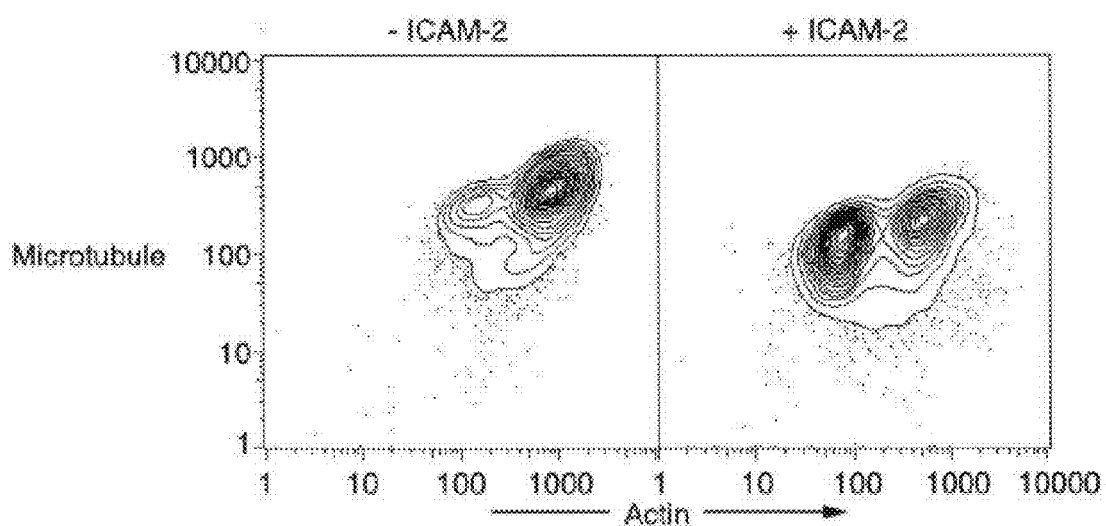
FIG_4B

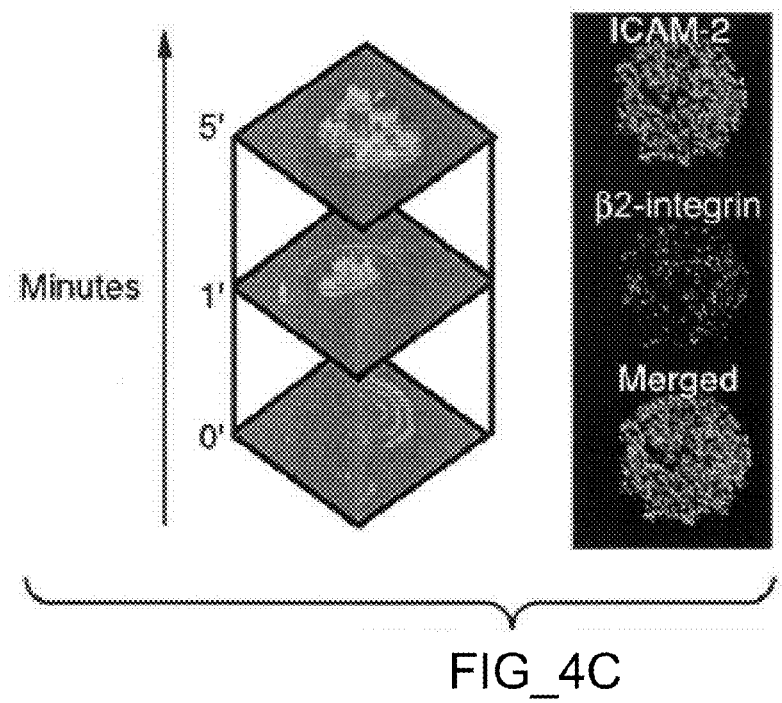
FIG_4C
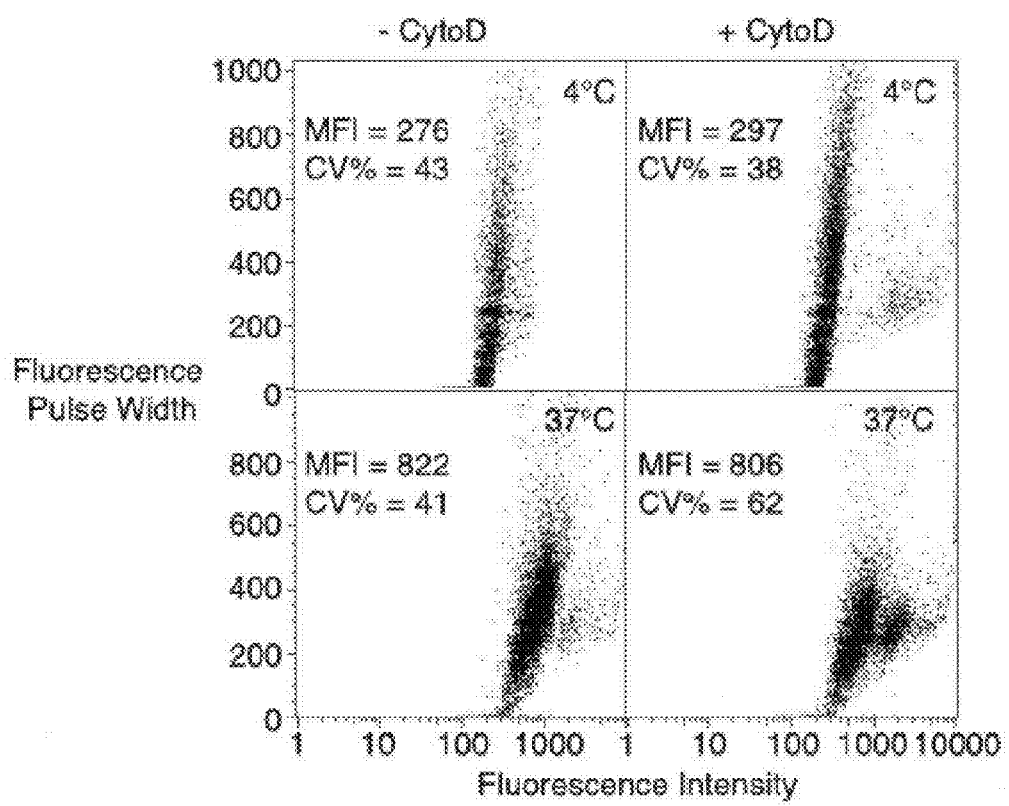
FIG_4D

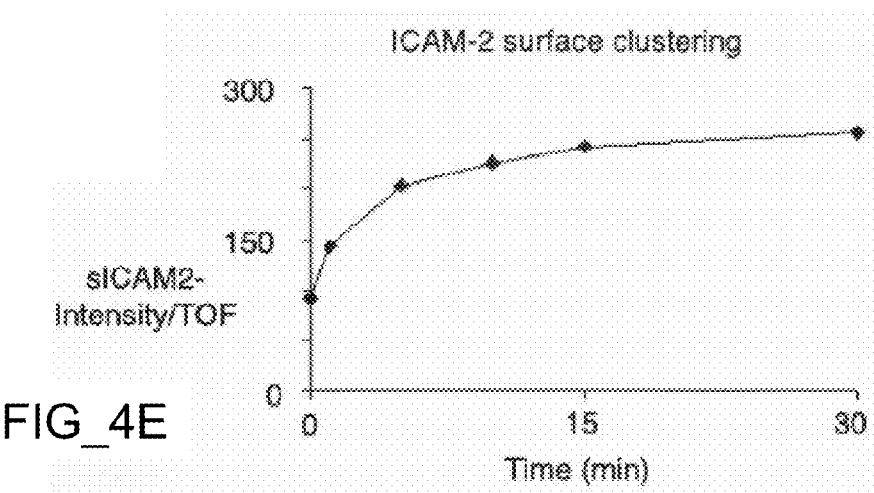
FIG_4E
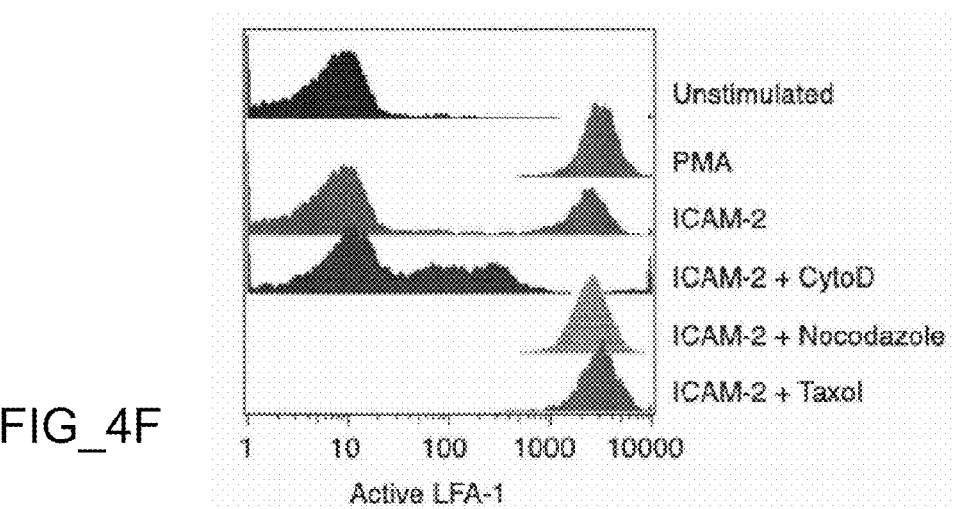
FIG_4F
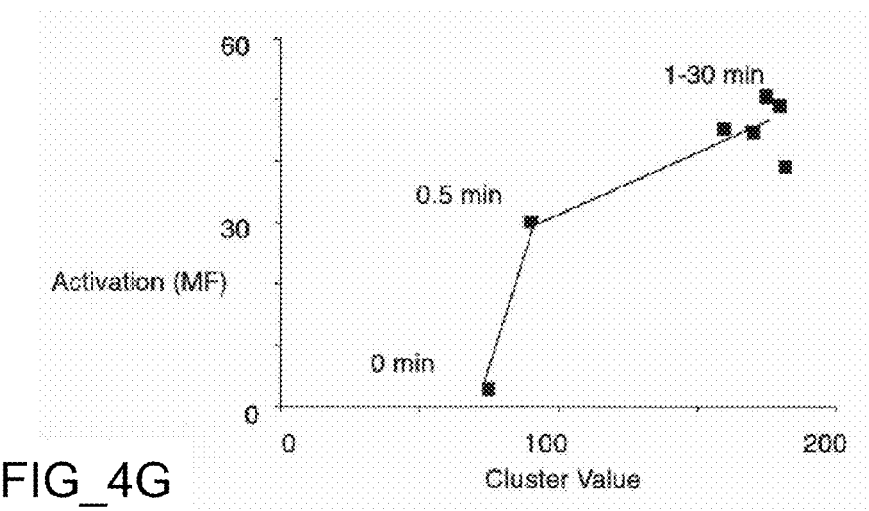
FIG_4G

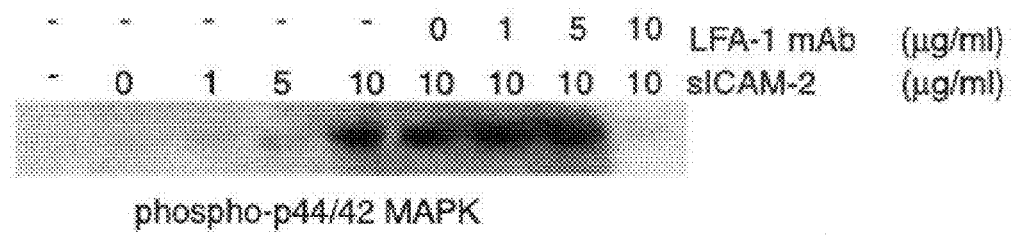
FIG_4H
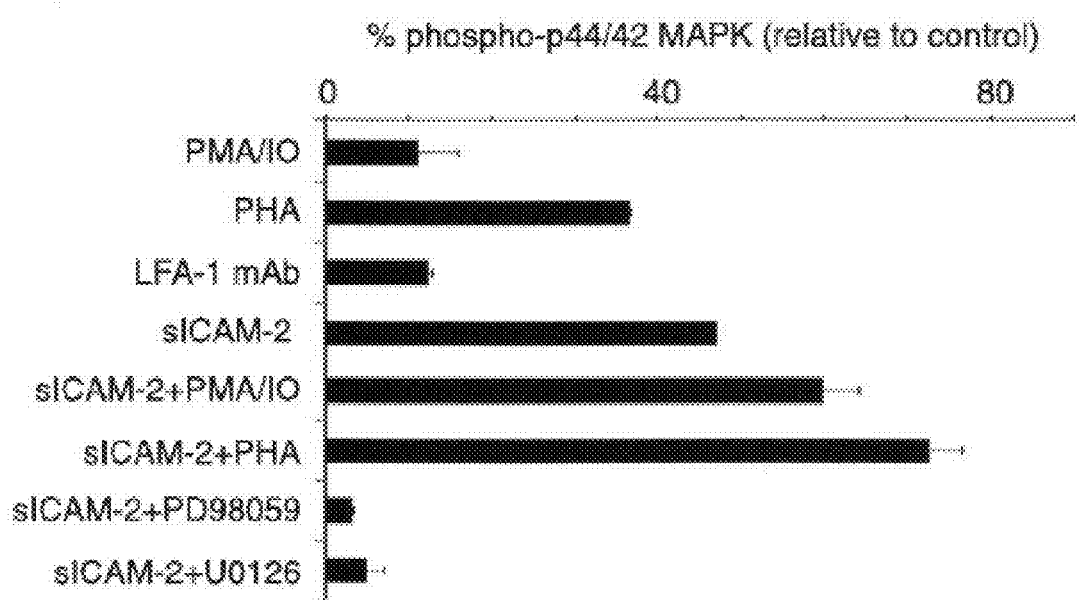
FIG_4I

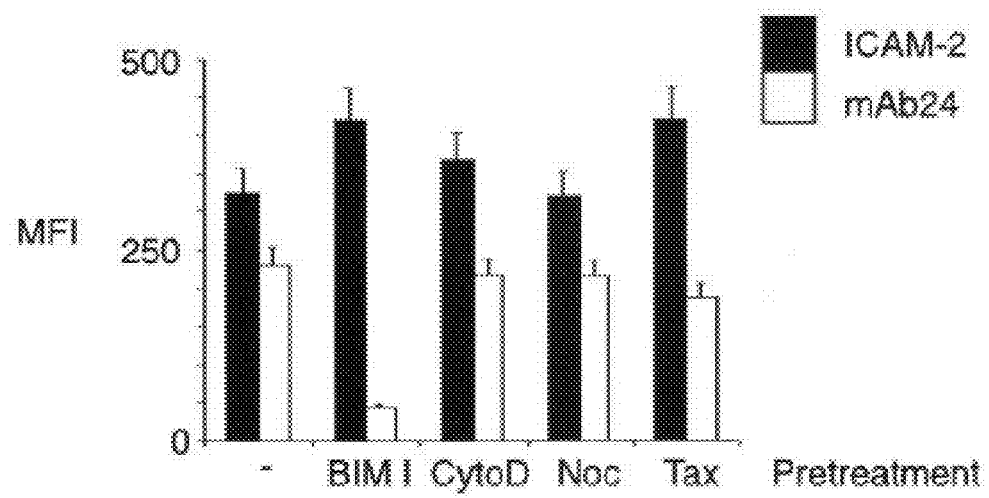
FIG_5A
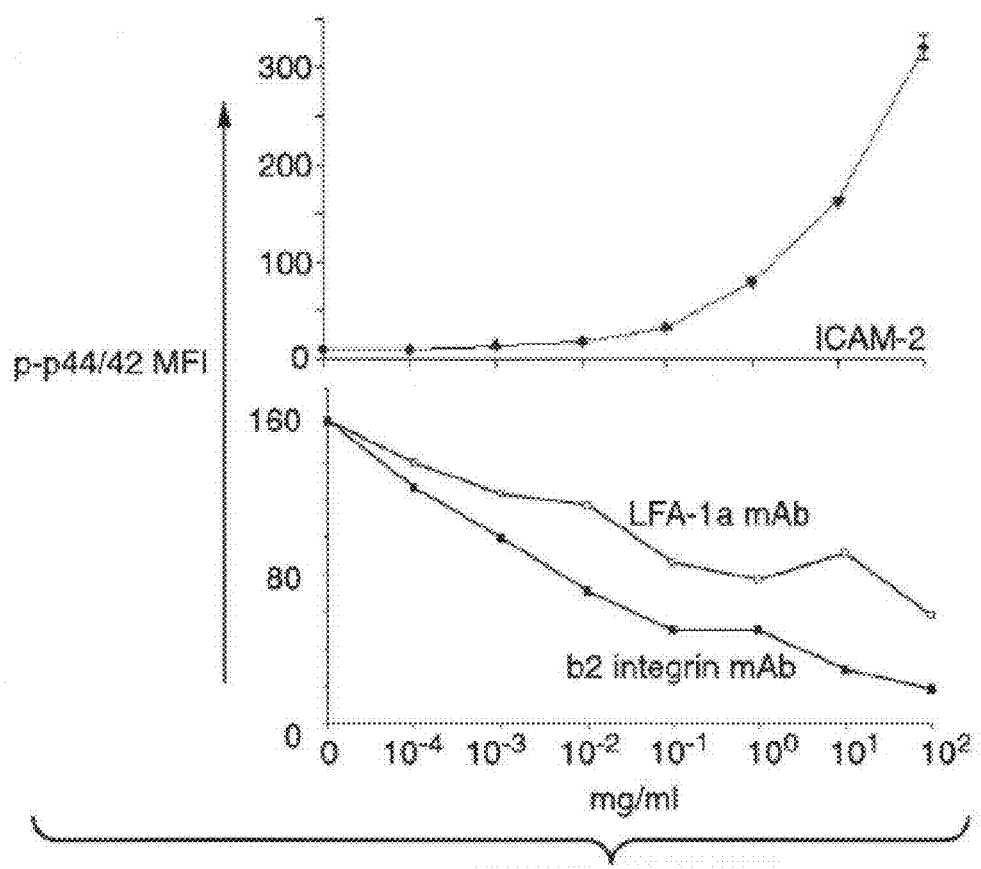
FIG_5B

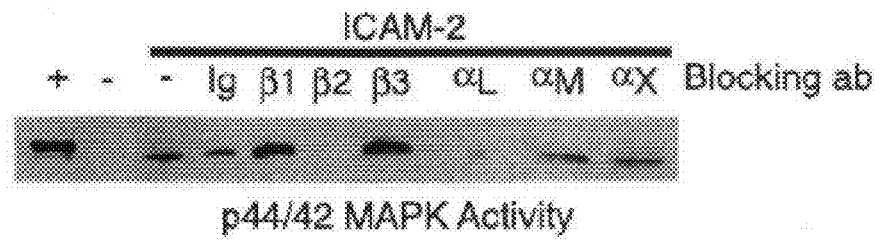
FIG_5C
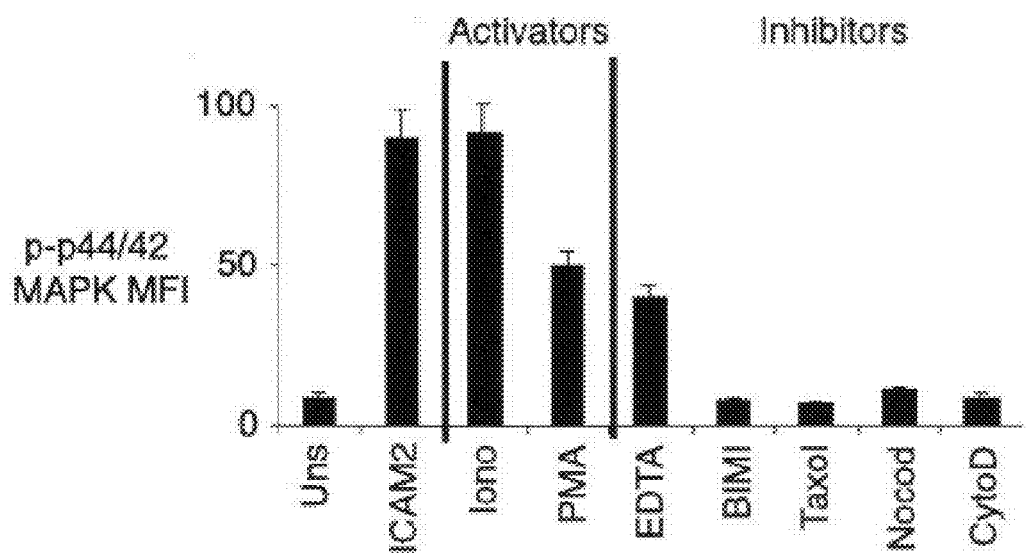
FIG_5D

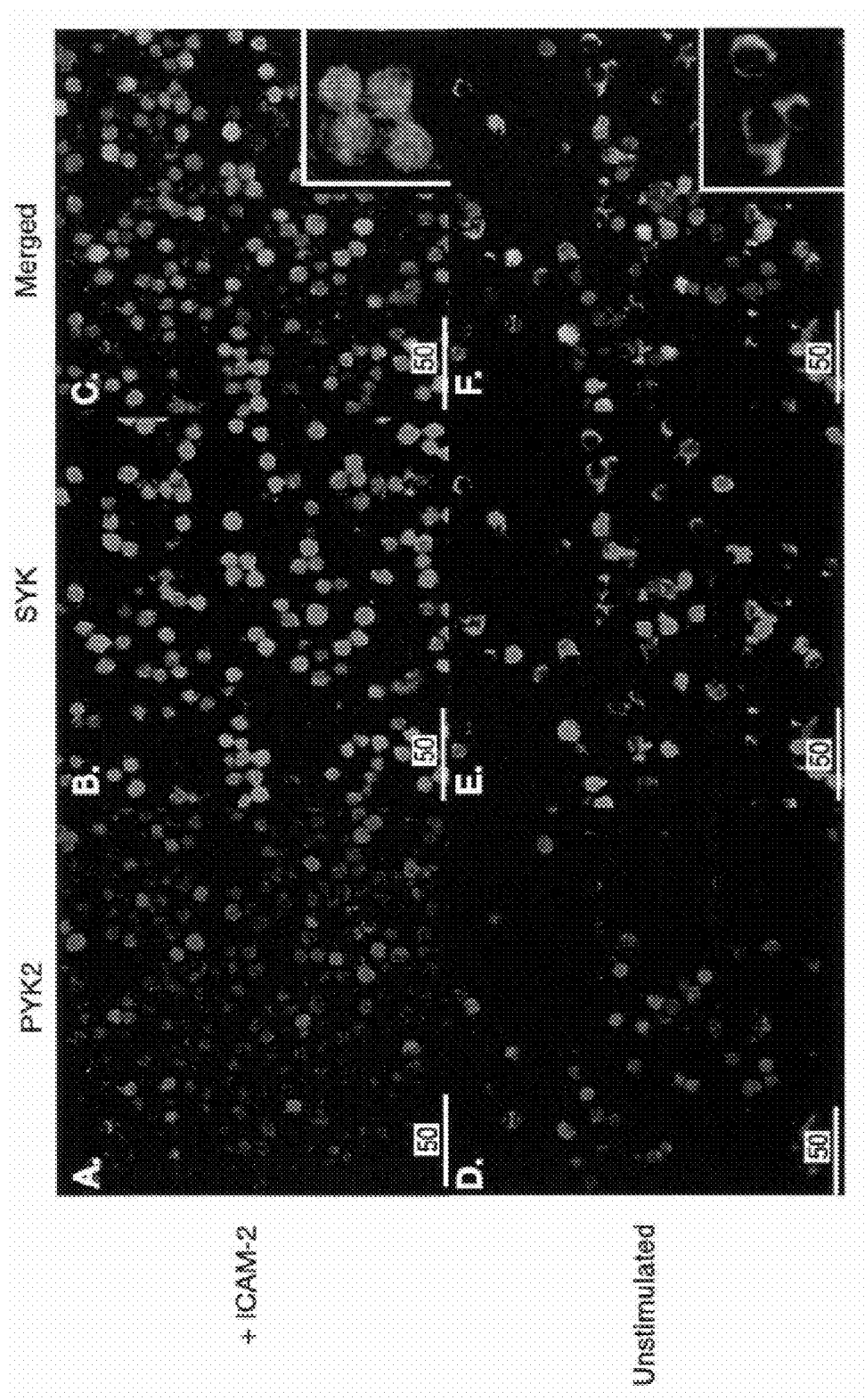
FIG_5E

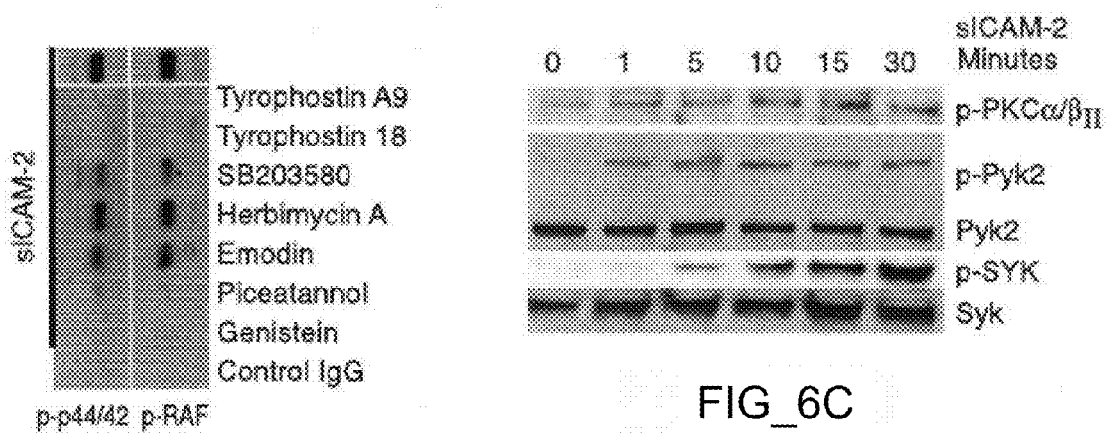
FIG_6A
FIG_6C
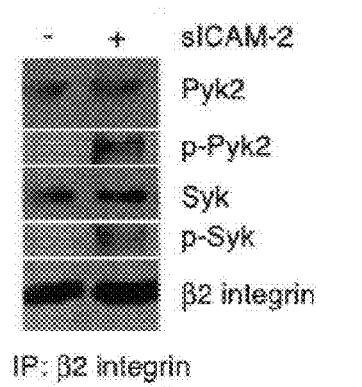
FIG_6B
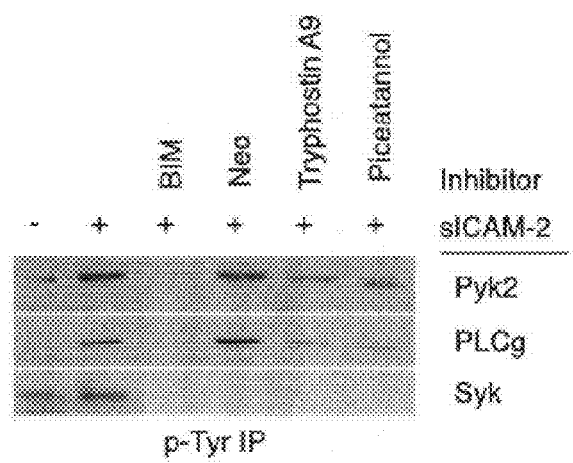
FIG_6E
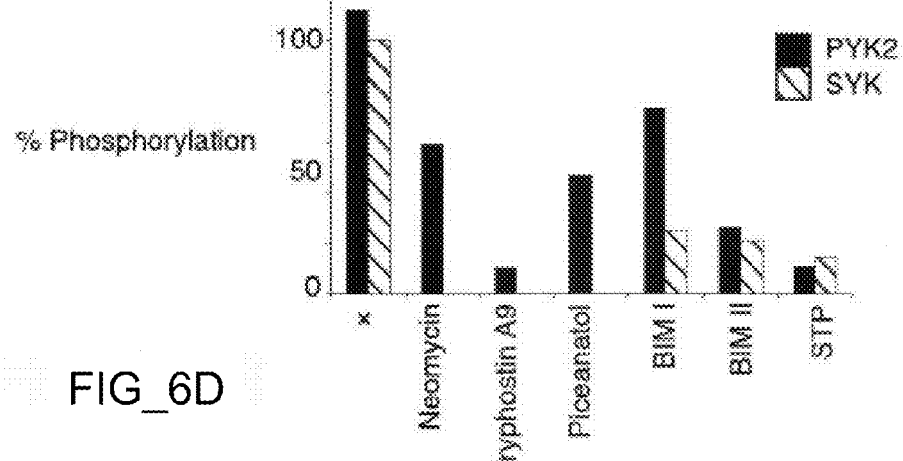
FIG_6D

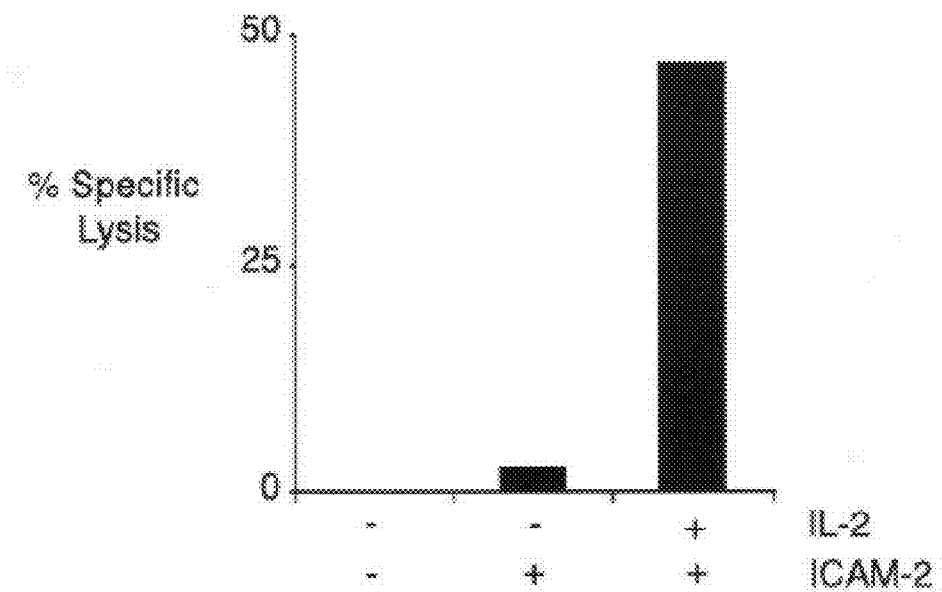
FIG_7A
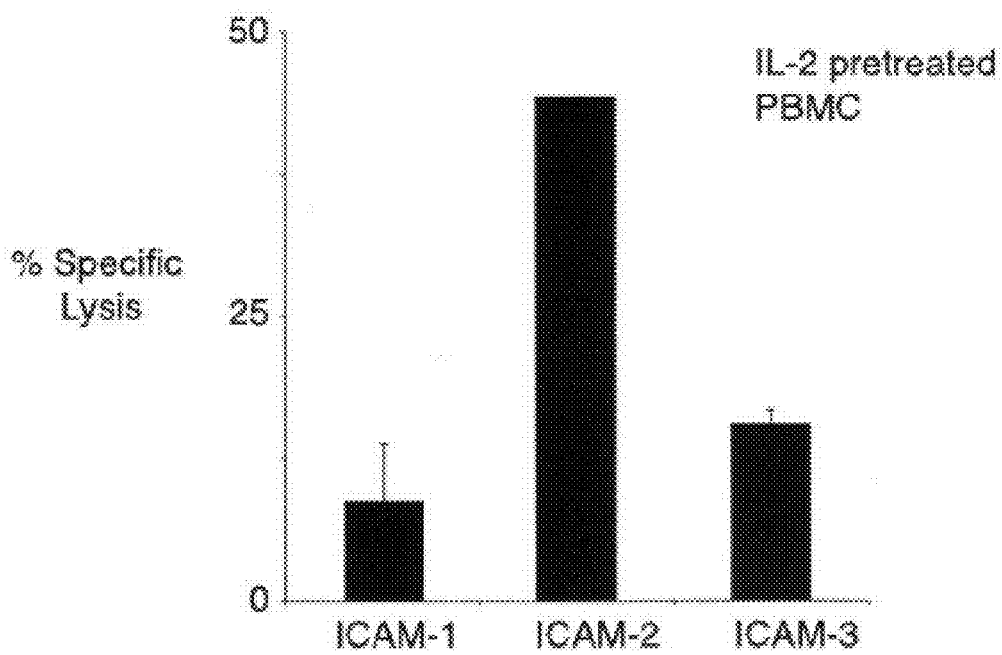
FIG_7B

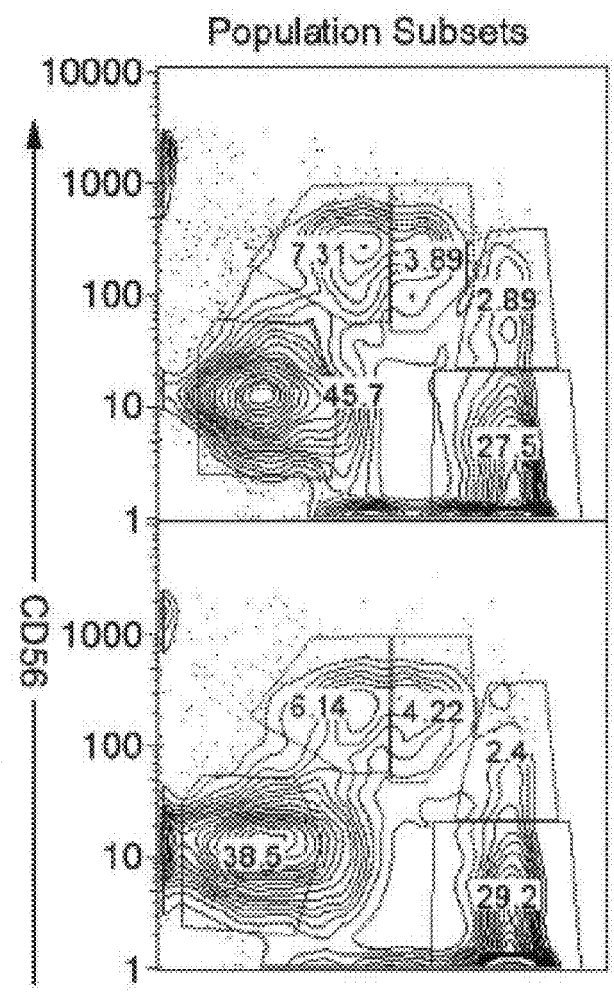
FIG_8A-1

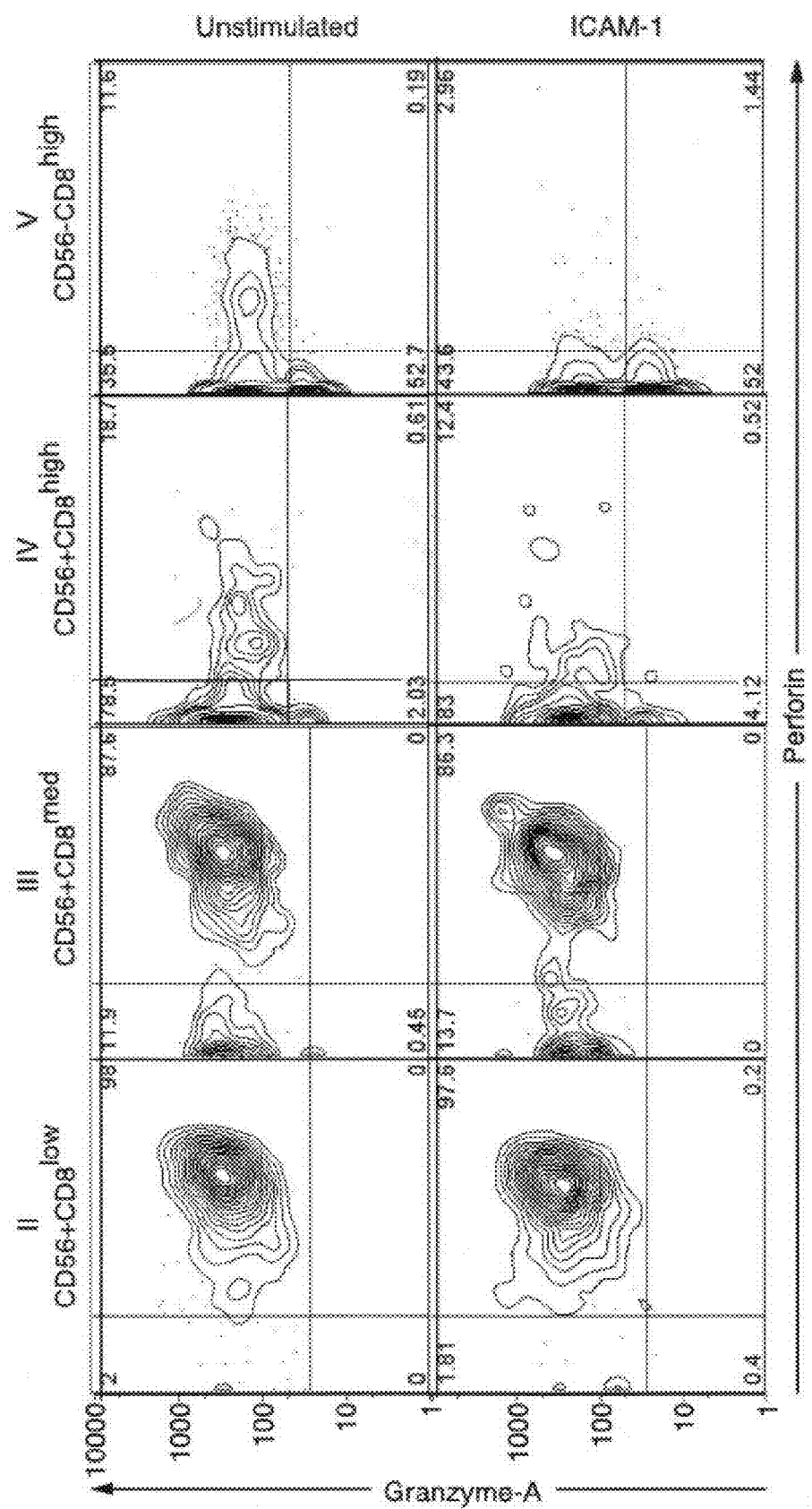
FIG_8A-2

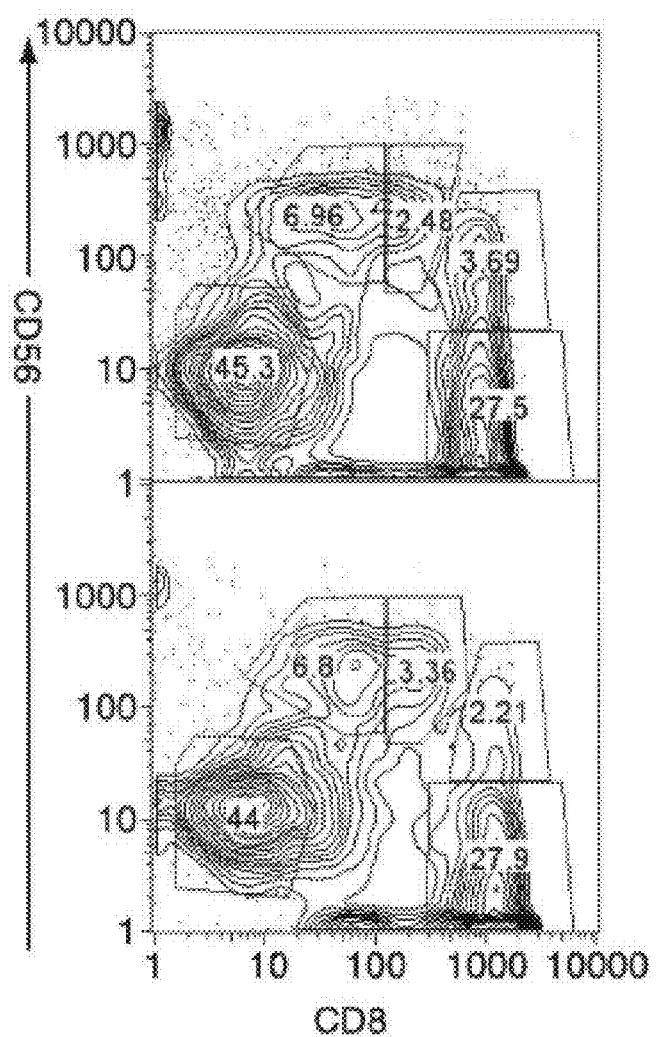
FIG_8A-3

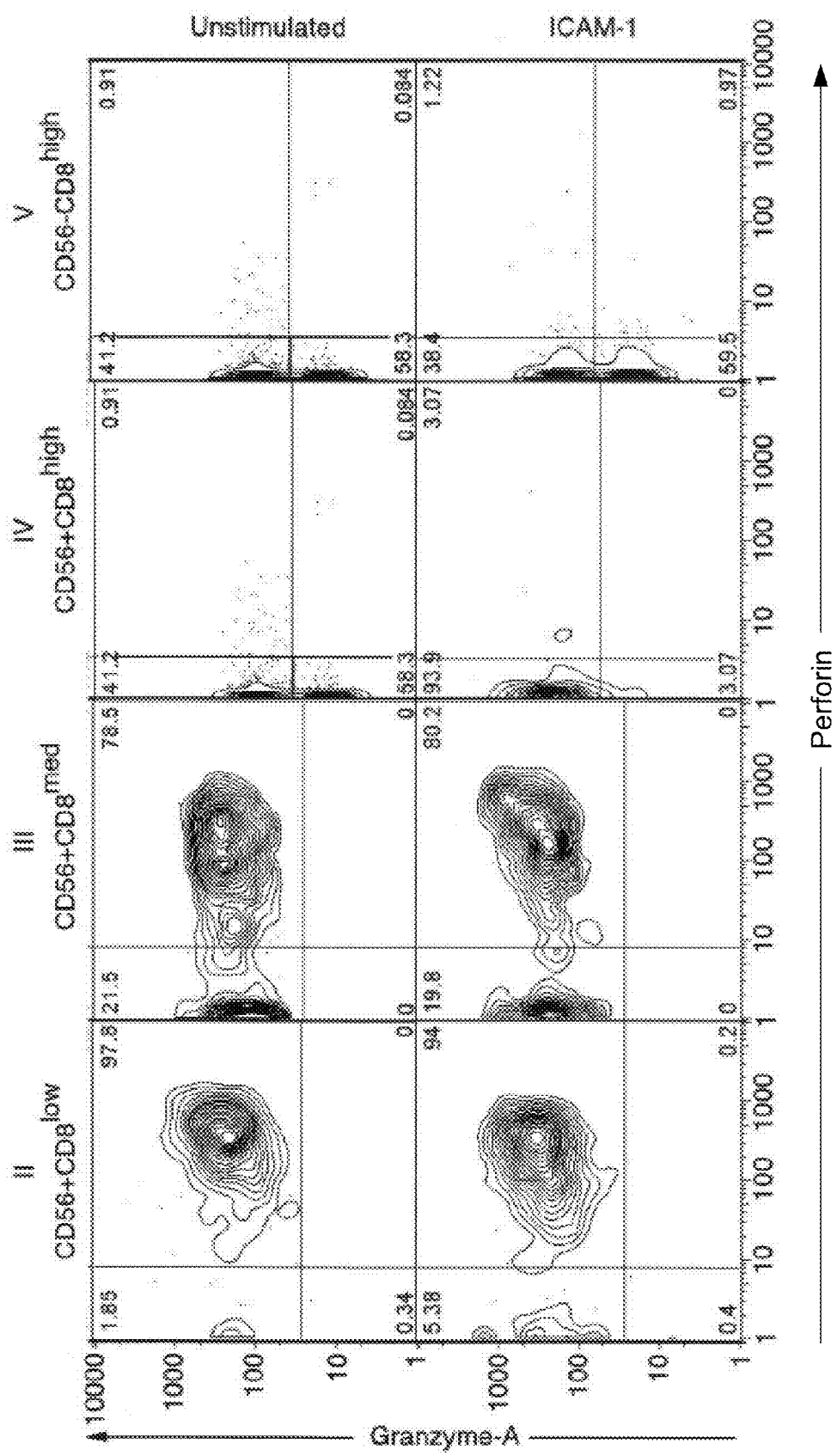
FIG_8A-4

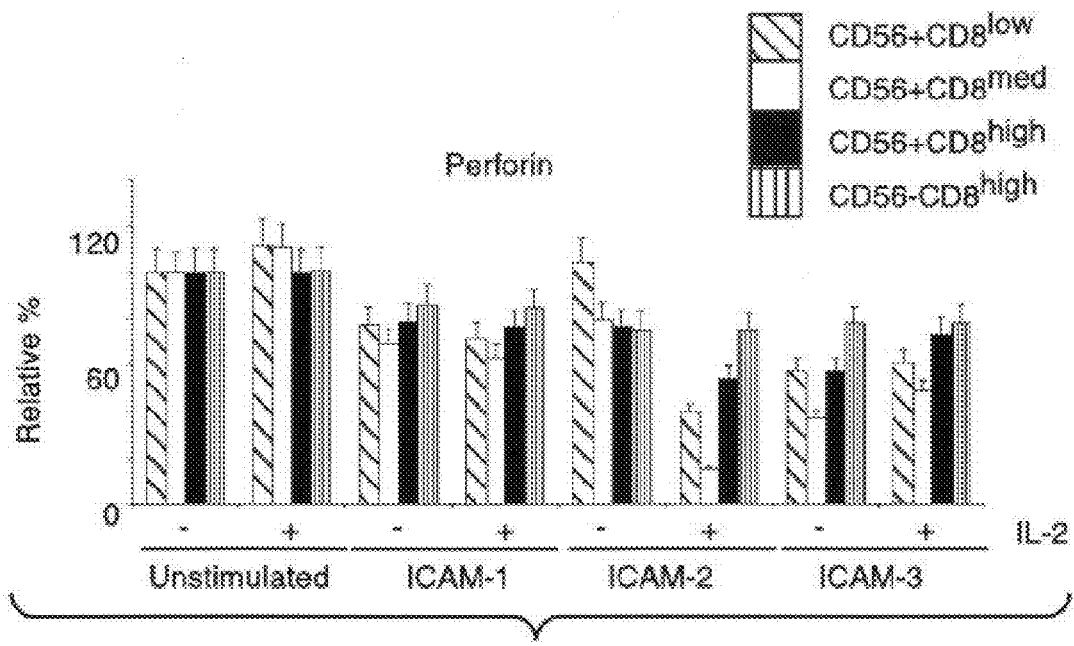
FIG_8B
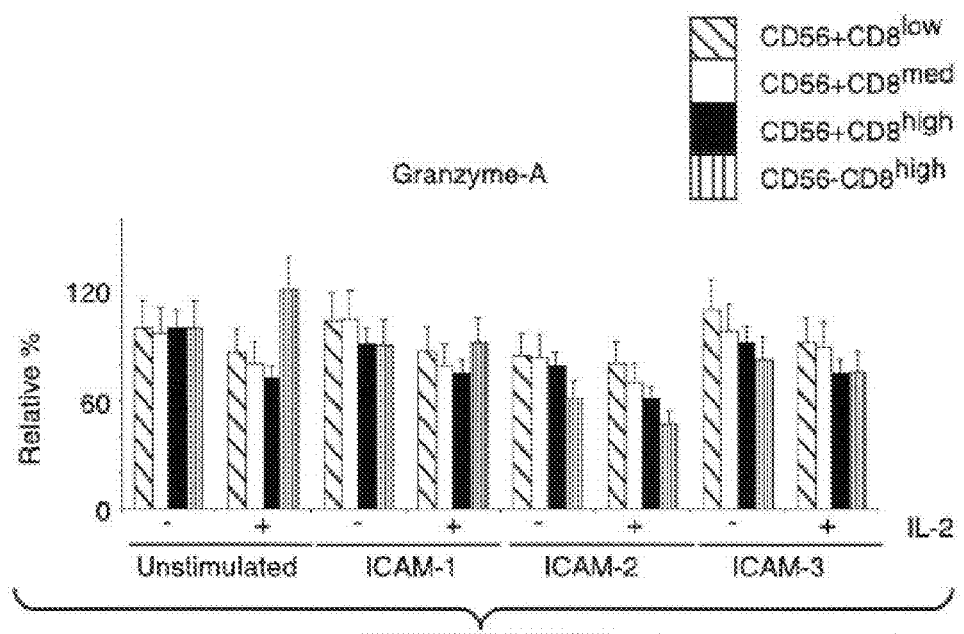
FIG_8C

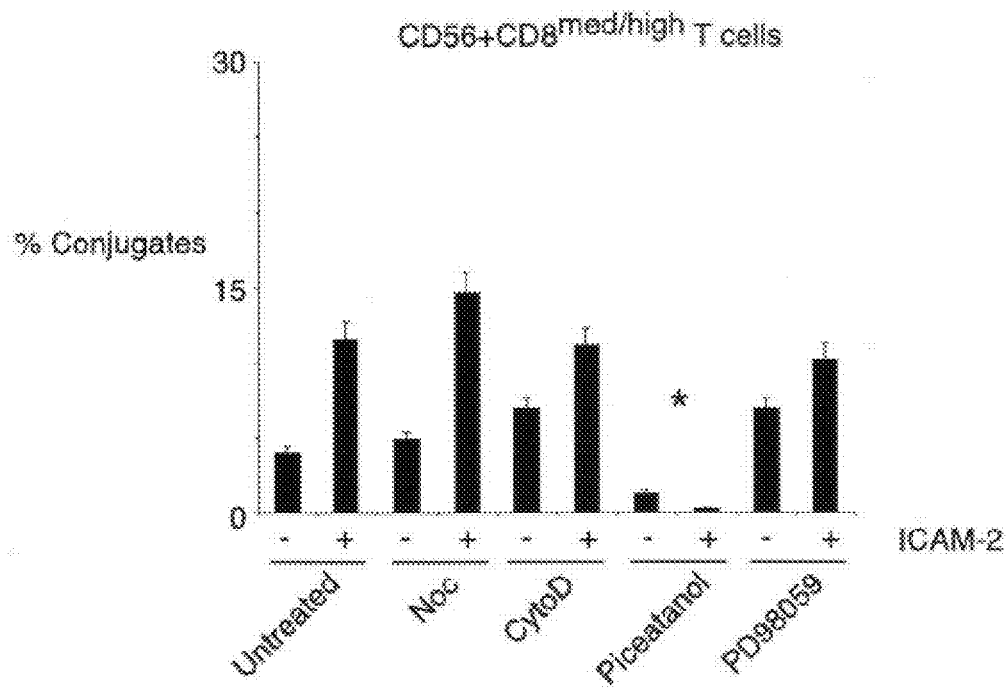
FIG_9A
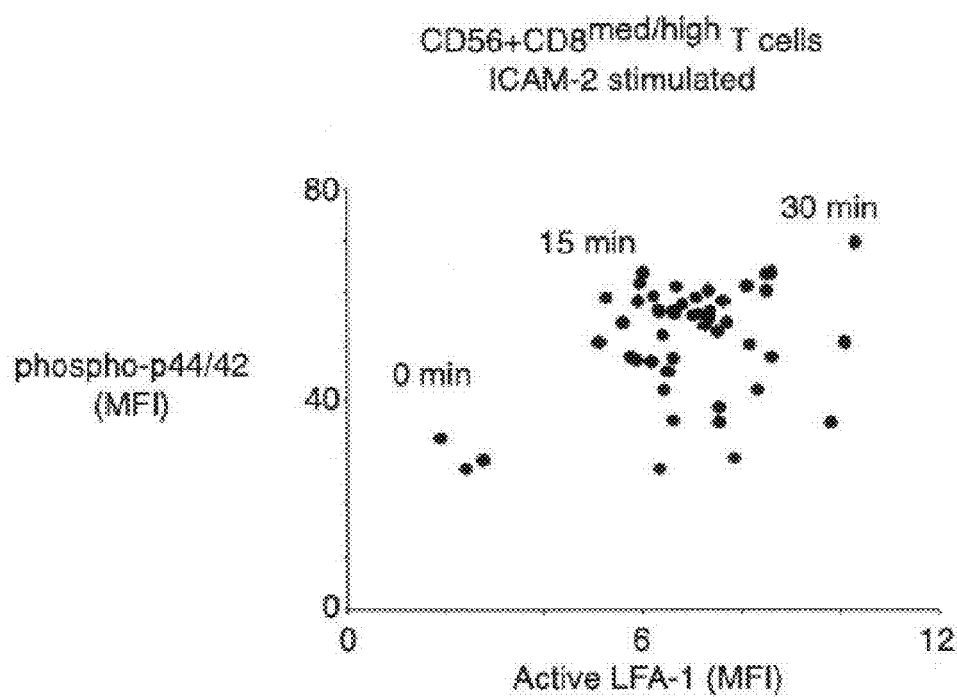
FIG_9B

METHODS AND COMPOSITIONS FOR DETECTING RECEPTOR-LIGAND INTERACTIONS IN SINGLE CELLS

This application is a continuation of U.S. Ser. No. 12/551,333, filed Aug. 31, 2009, which is a continuation of U.S. Ser. No. 11/655,785, filed Jan. 18, 2007, now U.S. Pat. No. 7,695,924, which is a continuation of U.S. Ser. No. 10/346,620, filed Jan. 16, 2003, now U.S. Pat. No. 7,381,535, which is a continuation in part of U.S. Ser. No. 10/193,462, filed Jul. 10, 2002, now U.S. Pat. No. 7,563,584, which claims the benefit of the filing date of U.S. Ser. No. 60/304,434, filed Jul. 10, 2001, and U.S. Ser. No. 60/310,141, filed Aug. 2, 2001, all of which are hereby incorporated by reference.

FIELD OF THE INVENTION

The invention relates generally to the field of protein detection using flow cytometry. More specifically, the invention relates to simultaneously detecting the clustering and activation states of receptor elements in single cells using flow cytometry and, more particularly, using polychromatic flow cytometry.

BACKGROUND OF THE INVENTION

Proteins are the major components of cells. The spatiotemporal expression pattern and the subcellular localization of proteins determines the shape, structure, and function of cells. Proteins are assembled from 20 different amino acids, each with a distinct side chain and chemical property. This provides for enormous variety in the chemical properties of proteins and the activities they exhibit.

Many proteins are dynamically regulated such that their activity is altered in response to certain intracellular or extracellular cues. In general, the response to these cues is mediated by a broad class of proteins termed receptors. While receptors employ a wide variety of means to transduce intracellular and extracellular cues, a general mechanism involves a receptor binding a ligand, which activates the receptor to propagate a signal that eventually results in altered protein activity within the cell. Because receptors play such an integral role in transducing intracellular and extracellular signals, they have been the subject of intense biochemical study.

Study of receptor function often requires immobilization of a receptor on a solid support. In Western blot analysis, receptors of interest are first separated by electrophoresis and then transferred and immobilized onto a nitrocellulose or a polyvinylidene difluoride (PVDF) membrane. In the phage display screening of a protein expression library, several hundred thousand proteins expressed by phages are immobilized on membranes. In both Western blotting and phage display screening, receptors are immobilized non-covalently. The receptor of interest is then selected by its unique property, i.e., interaction with an antibody. In some other applications such as immunoprecipitation and affinity purification, agents (e.g., antibodies, ligands) are covalently conjugated onto solid supports (e.g., agarose beads) through their primary amines, sulfhydryls or other reactive groups. In general, receptors retain their abilities of interacting with other proteins or ligands after immobilization. However, even with the immobilization of a multiplicity of receptors from a sample, the problems of simultaneous detection of receptor expression, receptor form, and receptor activity for a multiplicity of receptors remains.

Thus, an object of the present invention is to overcome the problems described above. Accordingly, the present invention provides an approach for the simultaneous determination of the clustering and activation states of a plurality of receptors in single cells. This approach permits the rapid detection of heterogeneity in a complex cell population based on receptor clustering and activation states, and the identification of cellular subsets that exhibit correlated changes in receptor clustering and activation within the cell population. Moreover, this approach allows the correlation of cellular activities or properties, such as surface molecule expression or cell granularity, with receptor clustering and activation at the single cell level.

SUMMARY OF THE INVENTION

In accordance with the above objects, the present invention provides methods and compositions for simultaneously detecting the clustering and activation state of receptor elements in single cells using flow cytometry. The invention further provides methods and compositions for simultaneously detecting multiple clusters and activation states of receptor elements in single cells using flow cytometry.

In another aspect the present invention the present invention provides a method of detecting the clustering of receptor elements in single cells, said method comprising: a) providing a sample comprising a cell, wherein the cell comprises receptor elements; b) contacting that cell with binding elements that bind to at least one of the receptor elements to activate the formation of clusters, wherein each of the binding elements comprise a label, wherein the clusters comprise; i) at least two receptor elements, ii) at least one binding elements bound to at least one of the receptor elements of the cluster; and c) detecting the label.

In another embodiment the present invention provides a method of simultaneously detecting multiple clusters in single cells, wherein the method comprising: a) providing a sample comprising a cell wherein the cell comprises a plurality of different receptor elements; b) contacting the cell with a plurality of different binding elements that bind to at least one of the different receptor elements to activate the formation of multiple clusters, wherein each of the different binding elements comprise an identifying label, wherein the clusters comprise; i) at least two receptor elements; ii) at least one binding element bound to at least one receptor element of the cluster; and c) detecting the label.

In a further embodiment the instant invention provides a method of simultaneously detecting the activation state and clustering of receptor elements in single cells, said method comprising: a) providing a sample comprising a cell, wherein the cell comprises at least first receptor elements; b) contacting the cell with at least first activation-specific antibodies that binds to an isoform of the first receptor element; wherein each of first activation-specific antibodies comprise an identifying label; c) contacting the cell with at least first binding elements that bind to at least one of the receptor elements to activate the formation of clusters, wherein each of the first binding elements comprise an identifying label, wherein the clusters comprise; i) at least two receptor elements; ii) at least one binding elements bound to at least one receptor elements of the cluster; and d) simultaneously detecting the identifying label of the first activation-specific antibodies and the identifying label each of the clusters.

In another embodiment, the present invention provides the methods described above, wherein the binding of the binding elements to the receptor elements is activated by providing the cell with an activator.

In another embodiment, the present invention provides the methods described above, wherein the label of the binding element comprises an antibody conjugated to a fluorophore, and wherein the antibody binds to the binding element.

In another embodiment, the present invention provides the methods described above, wherein the clustering activates the receptor elements in the clusters.

In another embodiment, the present invention provides the methods described above, wherein the signal is proportional to the number of the clusters.

In another embodiment, the present invention provides the methods described above, wherein the detecting is by flow cytometry.

In another embodiment, the present invention provides the methods described above, wherein the detecting further comprises using a FACS machine.

In another embodiment, the present invention provides the methods described above, wherein the detecting further comprises using a doublet discriminator.

In another embodiment, the present invention provides the methods described above, wherein the sample is from a patient.

In another embodiment, the present invention provides the methods described above wherein the receptor elements are not Leukocyte Function Antigen-1.

In another embodiment, the present invention provides the methods described above wherein the receptor elements are not integrins.

BRIEF DESCRIPTION OF THE DRAWINGS

FIG. 1 depicts a general diagram of receptor element clustering and activation.

FIGS. 2A, 2B and 2C depict diagrams of three general mechanisms of receptor element clustering.

FIG. 3 depicts results demonstrating that soluble ICAM-2 binding induces LFA-1 clustering and cytoskeletal polarization. A) Purified human ICAM-2 from retrovirally transduced NIH3T3 (see materials and methods) was tested for purity, size, and aggregate formation by native gel electrophoresis and gel filtration. Analysis of purified ICAM-2 from two different preps and ICAM2-FC from NSO cells. Molecular weight was calculated using relative distance migration from a molecular weight standard. Concentration was determined using serial dilutions of BSA as a standard. Molecular weight and concentration are displayed in the figure. B) ICAM-2 ligand binding to cell surface as a function of time. $5 \times 10^6$ unstimulated and PMA stimulated (1 µg/ml, 30 min) Jurkat T cells were incubated with ICAM-2-FITC or LFA-1-FITC antibody (1 µg/ml) and subjected to time dependent flow cytometry. Mean fluorescence intensity was plotted per time of a gated homogenous cell population. Flow rate was maintained at 200-300 cells/second, with fluorescence intensity values acquired at 10 millisecond intervals for 1200 seconds. C) Flow cytometric analysis of ICAM-2-FITC and α-LFA-1-FITC surface binding on cytochalasin D treated (10 µM, 30 min) Jurkat cells at 37° C. and 4° C. D) Curve fit analysis of ICAM-2-FITC binding per $10^4$ cells. Jurkat cells were incubated with, ICAM-2-FITC at 37° C. for 30 min at indicated concentrations in 50 µL volume. Cells were washed 1×, and analyzed for mean fluorescent intensity (MFI) of $10^4$ cells. Percent ICAM-2-FITC bound was calculated from the following equation: $100 \times [(MFI_{[x]} - MFI_{unstained})/(MFI_{[saturated]} - MFI_{unstained})]$ where [x]=ICAM-2-FITC concentration and [saturated]=concentration that saturated binding. Values were fit to the equation $Y = m1 \cdot M0/(m2 + M0)$ (see materials and methods). E) Native gel electrophoresis of purified ICAM-2. Gel was coomasie stained and purified ICAM-2 did not display aggregates (after gel filtration, we found that the added glycerol in the purification step eliminated higher molecular weight species formation). F) Purity analysis of ICAM-2 by native PAGE. Quantity was determined from densitometry measurements of entire lane. Percent purity was determined from calculating density of band relative to total density of the lane. ICAM-2 from prep one (left) and from prep 2 (right). Purity was greater than 98%. G) ICAM-2 was conjugated to FITC and purified conjugate (by spin chromatography) was immunoblotted with anti-ICAM-2 antibody (left panel) and subsequently verified for fluorescent conjugation in gel (right panel). H) Treatment of cells with cytochalasin D at low concentrations at 40 C led to enhanced ICAM-2 binding in a subset of cells and saturated at 370 C. Titration of ICAM-2-FITC surface binding at 370 C and 40 C in cytochalasin D treated (10 mM, 30 min) and untreated Jurkat cells by flow cytometry. Median Fluorescence Intensity (MFI) is plotted as a function of ICAM-2-FITC concentration.

FIG. 4 depicts the results of experiments demonstrating the simultaneous detection of ICAM-2 induced LFA-1 clustering, activation, and actin/microtubule reorganization. A) Confocal microscopy of actin and microtubule architecture upon ICAM-2 stimulus (10 µg/ml, 30 min) in Jurkat cells. Actin was stained by phalloidin-alexa633 and tubulin by taxol-alexa546. Inserts display enlarged cell image of representative treatment B) Flow cytometric staining for actin and microtubules as described above. C) Left: Fluorescence topography analysis of ICAM-2-FITC (1 µg/ml, time as indicated) surface distribution. Intensity color gradient depicts high and low fluorescent intensity values. Right: Confocal microscopy of ICAM-2-FITC surface binding (10 µg/ml, 30 min) and anti-β2-alexa568 (clone CTB104). D) Staining for ICAM-2-FITC surface binding (fluorescence intensity) and surface distribution (fluorescence pulse) in cytochalasin D treated Jurkat cells at 37° C. and 4° C. by flow cytometry. E) Values for ICAM-2-FITC fluorescence intensity per time-of-flight per cell as described in text. F) Flow cytometric staining for LFA-1 activation by mAb24-alexa633. Stimuli as indicated (10 µM, 30 min), PMA (1 µg/ml) prior to ICAM-2 stimulation (10 µg/ml, 30 min). Staining was performed at 37° C. G) Mean fluorescence intensity (MFI) values of mAb24-633 and ICAM-2 cluster values, computed as described above, as a function of time.

H-I) depict ICAM-2 induced p44/42 MAPK phosphorylation, and inhibition by LFA-1 mAb and comparison with other stimuli. H) Phospho-p44/42 MAPK immunoblot of total lysates from Jurkat cells stimulated with ICAM-2 (concentrations indicated in figure, 30 min) and subsequently blocked with increasing concentrations of LFA-1 mAb. I) Comparison of phospho-p44/2 MAPK induction to stimuli using FACS based detection of phospho-p44/42 MAPK. Stimuli were either 1 mg/ml (PHA, PMA, ionomycin), 10 mg/ml (LFA-1 mAb and ICAM-2), or 10 mM for PD98059 and U0126. Chemical inhibition was done 30 min prior to stimulation. Data is presented as percent phospho-p44/24 MAPK positive cells relative to unstimulated cells. Note the difference between LFA-1 mAb crosslinking and ICAM-2 stimulation.

FIG. 5 depicts the results of experiments demonstrating ICAM-2 induced p44/42 MAPK activation via LFA-1 interaction. A) Mean fluorescence intensity values (MFI) of ICAM-2-FITC (adhesion) and mAb24-Alexa633 (LFA-1 activation) in treated Jurkat cells (as above). Control unstimulated and/or compound pretreated values were subtracted. B) Top panel: Intracellular phospho-p44/42 MAPK detection as a function of ICAM-2 dose in Jurkat cells by flow cytometry (see Material and Methods). Mean fluorescence intensity values (MFI) were plotted ±standard deviation (SD). Bottom panel:

ICAM-2 treated Jurkat cells were stained for intracellular phospho-p44/42 MAPK as described above. mAbs to β2 and $\alpha_L$ integrins (10 µg/ml, 10 minutes) were titrated prior to ICAM-2 treatment as indicated and plotted for MFI±SD. C) ICAM-2 induced p44/42 MAPK activity is blocked by β2 and $\alpha_L$ integrin antibodies as determined by a p44/42 MAPK kinase assay. Conditions for induction and inhibition are as described above. Recombinant active p44/42 MAPK served as an internal positive control (denoted by "+"). D) Inhibition and activation profile for intracellular phospho-p44/42 by flow cytometry in the presence of chemical agents (10 mM), EDTA (1 mM), or PMA, ionomycin and ICAM-2 stimulus (as indicated above). MFI values±SD are plotted. E) depicts that sICAM-2 induces Pyk2 and Syk membrane localization. Confocal Microscopy of Jurkat cells treated with ICAM-2 protein (10 mg/ml) or bovine serum albumin (Unstimulated, 10 mg/ml) for 10 minutes and prepared for confocal microscopy (see material and methods). Cells were stained for Pyk2 and Syk. Panels A-C represents unstimulated cells and panels D-F represent ICAM-2 treated cells. Scale bar is denoted in lower left corner of panels (in micrometers).

FIG. 6 depicts the results of experiments demonstrating ICAM-2 induced phosphorylation of Pyk2 and Syk, and β2 integrin association. A) Phospho-raf and phospho-p44/42 immunoblot inhibition profile by tyrosine kinase inhibitors. $1 \times 10^6$ cells were treated with indicated compound (10 mM, 30 min) and then stimulated with ICAM-2 (10 mg/ml, 30 min). Cell lysates were immunoblotted for phospho-raf and phospho-p44/42. Compound alone did not induce detectable phosphorylation. B) Pyk2 and Syk are phosphorylated and co-immunoprecipitate with b2 integrin upon ICAM-2 stimulus. Phospho-specificity was determined by phospho-PykpY402 and phospho-syk(Tyr525/526) antibodies. C) Kinetic analyses of the phosphorylation state of PKCa/b, Pyk2, and Syk as a function of ICAM-2 stimulus per time. Cells were treated and processed as above. Phospho-specific $PKCa/b_{II}$ (Thr638) and the following antibodies were used; Pyk2 and Syk were first immunoprecipitated, probed with anti-phosphotyrosine antibody (PY20), stripped and subsequently probed with indicated non-phospho specific antibody. Immunoblots are representative of triplicate experiments. D) and E) depict that LFA-1 induced phosphorylation of Pyk2 and Syk is dependent on PKC. We screened for the inhibition of sICAM-2 induced Pyk2 and Syk phosphorylation by chemical inhibitors to tyrosine kinases using a phospho-tyrosine based ELISA. Pyk2 phosphorylation was abrogated in the presence of PKC inhibitors bisindolylmaleimide II (BIM II) and staurosporine (STP), in addition to tyrphostin A9, a specific Pyk2 inhibitor. Pyk2 phosphorylation was also affected by inhibitors of phospholipase Cg (neomycin), inhibitors of Syk (piceatannol), and PKC inhibitor BIM I. Syk phosphorylation was completely abolished by inhibition of Pyk2, PLCg1, and strongly affected by PKC inhibitors. Thus, both Pyk2 and Syk phosphorylations were dependent on PKC activity, while Syk phosphorylation was additionally dependent on PLCg1 and Pyk2 activity. It was not possible to assess specific PKC isozymes by this method. A chemical genetic approach was undertaken to determine the hierarchy of PKC, Pyk2, PLCg1, and Syk activities in response to sICAM-2 stimulus by verifying phosphorylation status of each kinase in the presence of respective chemical inhibitors. Inhibition of PKC with BIM II abrogated phosphorylation of Pyk2, PLCg1, and Syk. Inhibition of PLCg1 by neomycin abrogated phosphorylation of Syk, with no inhibition observed for Pyk2. Inhibition of Syk by piceatannol did not block phosphorylation of Pyk2 or PLCg1. These observations suggest that PKC activation is upstream of PYK2, PLCg, and SYK activities, and also that SYK activity is consequential to PYK2 and PLCg1 activity. Thus, the upstream signaling events from LFA-1 to Raf-1 appear to involve PKC/Pyk2/PLCg1/Syk.

FIG. 7 depicts the results of experiments demonstrating that ICAM-2 induces cytotoxic lymphocyte activity in IL-2 activated human PBMC. A) PBMC were either treated with ICAM-2 (10 mg/ml) in the presence of IL-2 for 12 hr and then incubated with CFSE labeled target HL60 cells at a 50:1 E:T ratio for 4 hrs. Remaining HL60 cells were quantified by flow cytometry. B) PBMC were treated with IL-2 (100 U/ml, 12 hrs) and treated with ICAM-1, -2, or 3 FC proteins (10 mg/ml) and used in a cytotoxicity assay as described above. Results are representative of 4 independent experiments.

FIG. 8 depicts the results of experiments demonstrating ICAM-2 exhibits differences to ICAM-1 and ICAM-3 in mediating perforin and granzyme release from $CD56^+CD8^+$ cytotoxic lymphocytes subsets. IL-2 activated PBMC (shown in A-1 and A-3) were mock-treated (IgG) (A-2), ICAM-1 (A-2), ICAM-2(A-4), or ICAM-3 (A-4) treated (10 mg/ml of FC fusion protein) for 12 hrs prior to incubation with target HL60 cells at a 50:1 E:T ratio for 4 hrs. Cells were then prepared for flow cytometry with CD8-CY5PE, CD56-PE surface stains, and perforin-CY5 and granzyme-A-FITC intracellular stains. Cells were gated for $CD56^+CD8^{low}$, $CD56^+CD8^{med}$, $CD56^+CD8^{high}$, $CD56^-CD8^-$, $CD56^-CD8^{high}$ populations as shown in A-1 and A-3 and population frequencies within appropriate gate. A-2 and A-4 are subset gated populations displayed for perforin and granzyme-A log fluorescent intensities. Results are representative of 3 independent experiments and were similar at 25:1 and 12.5:1 E:T ratios (data not shown). Manual calibration was performed. B) CD56CD8 population subsets were gated (as indicated) and displayed for intracellular perforin for ICAM-1, -2, -3 stimulated cells. Perforin percentage was calculated from the following equation where MFI equals mean fluorescent intensity: $100 \times [(MFI_{experimental} - MFI_{isotype\ mAb})/(MFI_{control} - MFI_{isotype\ mAb})]$. Unstimulated cells were used as control. C) Intracellular granzyme-A values were calculated and displayed as described above.

FIG. 9 depicts the results of experiments demonstrating that ICAM-2 induced LFA-1 mediated p44/42 MAPK correlates with LFA-1 activation in human $CD56^+CD8^+$ cells. A) Conjugate formation of CFSE labeled HL60 cells and $CD56^+CD8^+$ cells. Conjugate flow cytometric based assay was performed on PBMC treated with indicated chemicals (10 mM, 30 min) prior to treatment with ICAM-2 (10 mg/ml, 30 min). CFSE labeled HL60 cells were incubated at 25:1 E:T ratio for 5 min, and fixed with 1% paraformaldehyde. Cells were then immunolabeled with CD8 and CD56 antibodies, gated for $CD8^+CD56^+$ cell populations and percent HL60 fluorescence was made relative to total HL60 cells. B) IL-2 activated PBMC were either treated with ICAM-2 (10 mg/ml, 30 min) or mock-treated (IgG) and stained for active-LFA-1 (mAb24-Alexa633), phospho-p44/42-Ax488, CD8-CY5PE, and CD56-PE. $CD56^+CD8^+$ cell populations are gated and displayed for active LFA-1 vs. phospho-p44/42. The mean fluorescent intensities (MFI) of mAb24-Ax633 and phospho-44/42-Ax488 were computed and displayed over time as described above.

DETAILED DESCRIPTION OF THE INVENTION

Intracelluar assays of signaling systems have been limited by an inability to correlate functional subsets of cells in complex populations based on the clustering and activation state of receptor elements in a cell. Such correlations are important for distinguishing changes in signaling status that arise in rare cell subsets during signaling or in disease manifestations. The present invention solves these problems by providing methods and compositions for simultaneously detecting the receptor clustering state and activation state of a plurality of activatable receptor elements in single cells using flow cytometry. The invention further provides methods and compositions of screening for bioactive agents capable of coordinately modulating the activity or activation state of a plurality of activatable receptor elements in single cells. The methods and compositions can be used to determine the receptor clustering and activation profile of a cell for predicting or diagnosing a disease state, and for monitoring treatment of a disease state. Further, the methods and compositions of the present invention can be used optionally to sequentially detect the clustering and activation state of a plurality of receptor elements in single cells. In addition, the methods and compositions of the present invention can be used optionally to detect the activation state of a single receptor element or modulate the clustering or activation state of a single receptor element in single cells.

As shown in FIG. 1, detection of receptor element clustering may be determined as follows. First, a receptor element capable of associating with one or more receptor elements to form clusters is chosen. Next, a cell type containing that receptor is chosen. The cell is then contacted with a labeled binding element which is capable of binding to the receptor element and initiating the formation of clustering. Clustering of the receptor element can then be determined by detecting the label attached to the binding element. As will be appreciated by those of skill in the art, the labels may be any label that can be visualized and/or measured or otherwise identified so that its presence or absence can be determined.

Additionally, conversion of the receptor from one form to another (e.g. activation) of the receptor following the binding of a binding element may be detected by determining the presence of particular isoform of the receptor. Conversion from one isoform to another either initiates a signal that mediates the effects of a signaling pathway or conversely, turns off a signal that mediates the effects of a signaling pathway. Thus, by contacting the cell with labeled antibodies specific for a particular isoform, it is possible to determine whether or not that isoform is present.

Accordingly, the methods and compositions of the present invention may be used to detect clustering and conversion of receptor elements from one isoform to another. By "receptor element" is meant any protein, membrane-bound or soluble, capable of interacting with a ligand, e.g. hormone, peptide or small molecule, resulting in the propagation of an intra- or extracellular signal. The term receptor element, as used herein, encompasses both naturally occurring mutant and recombinant receptors.

In preferred embodiment, the receptor element is capable of clustering. By "clustering", and grammatical equivalents used herein, is meant any reversible or irreversible association of one or more receptor elements. Clusters can be made up of 2, 3, 4, etc., receptor elements. Clusters of two elements are termed dimers. Clusters of 3 or more receptor elements are generally termed oligomers, with individual numbers of clusters having their own designation, for example, a cluster of 3 receptor elements is a trimer, a cluster of 4 receptor elements is a tetramer, etc.

Clusters can be made up of identical receptor elements or different receptor elements. Clusters of identical receptor elements are termed "homo" clusters, while clusters of different receptor elements are termed "hetero" clusters. Accordingly, a cluster can be a homodimer, as is the case for the $\beta_2$-adrenergic receptor. Alternatively, a cluster can be a heterodimer, as is the case for $GABA_B$-R. In other embodiments, the cluster is a homotrimer, as in the case of TNFα, or a heterotrimer such the one formed by membrane-bound and soluble CD95 to modulate apoptosis. In further embodiments the cluster is a homo-oligomer, as in the case of Thyrotropin releasing hormone receptor, or a hetero-oligomer, as in the case of TGFβ1.

Activation or conversion of a receptor element from one isoform to another may be mediated either by receptor clustering or by the binding of a binding element to the receptor. Generally, initiation of clustering via the binding of a binding element results in the activation or signaling potential of a receptor. As will be appreciated by those of skill in the art, activation encompasses both the "turning on" or "turning "off" of a signal used to mediate a signaling pathway.

In a preferred embodiment, the activation or signaling potential of receptor elements is mediated by clustering, irrespective of the actual mechanism by which the receptor clustering is induced. As shown in FIG. 2, clustering can occur in a variety of ways. The definition includes receptors that are normally activated to cluster a) as membrane bound receptors by binding to ligands, b) as membrane bound receptors by binding to other surface molecules, or c) as intracellular (non-membrane bound) receptors binding to ligands.

In a preferred embodiment membrane bound receptor elements cluster upon ligand binding. One class of receptor elements includes membrane bound proteins, or complexes of proteins, which are activated to cluster upon ligand binding. As is known in the art, these receptor elements can have a variety of forms, but in general they comprise at least three domains. First, these receptors have a ligand binding domain, which can be oriented either extracellularly or intracellularly. Next, these receptors have a membrane-binding domain, which can take the form of a seven pass transmembrane domain (discussed below in connection with G-protein-coupled receptors) or a lipid modification, such as myristylation, to one of the receptor's amino acids which allows for membrane association when the lipid inserts itself into the lipid bilayer. Finally, the receptor has an signaling domain, which is responsible for propagating the downstream effects of the receptor.

Examples of such receptor elements include hormone receptors, cytokine receptors, steroid receptors, adhesion receptors, PDGF (platelet derived growth factor receptor), EGF (epidermal growth factor), VEGF (vascular endothelial growth factor), uPAR (urokinase plasminogen activator receptor), ACHR (acetylcholine receptor), IgE (immunoglobulin E receptor), estrogen receptor, thyroid hormone receptor, integrins ($\beta 1$, $\beta 2$, $\beta 3$, $\beta 4$, $\beta 5$, $\beta 6$, $\alpha 1$, $\alpha 2$, $\alpha 3$, $\alpha 4$, $\alpha 5$, $\alpha 6$), MAC-1 ($\beta 2$ and cd11b), $\alpha V \beta 3$, opiod receptors (mu and kappa), FC receptors, serotonin receptors (5-HT, 5-HT6, 5-HT7), β-adrenergic receptors, insulin receptor, leptin receptor, TNF receptor (tissue-necrosis factor), cytokine and chemokine receptors (IL1-a, IL-b, IL-2, IL-3, IL-4, IL-5, IL-6, IL-7, IL-8, IL-9, IL-10. IL-12, IL-15, IL-18, IL-21, CCR5, CCR7, CXCR4, CCR-1-10, CCL20), statin receptors, FAS receptor, BAFF receptor, FLT3 receptor, GMCSF receptor, and fibronectin receptor.

In a preferred embodiment the receptor element is a cytokine receptor. Cytokines are a family of soluble mediators of cell-to-cell communication that includes interleukins, interferons, and colony-stimulating factors. The characteristic features of cytokines lie in their functional redundancy and pleiotropy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily activate the Jak protein tyrosine kinase family, with resultant phosphorylation of the STAT transcriptional activator factors. IL-2, IL-4, IL-7 and Interferon γ have all been shown to activate Jak kinases (Frank et al. (1995) Proc. Natl. Acad. Sci. USA 92:7779-7783); Scharfe et al. (1995) Blood 86:2077-2085); (Bacon et al. (1995) Proc. Natl. Acad. Sci. USA 92:7307-7311); and (Sakatsume et al., (1995) J. Biol. Chem. 270:17528-17534). Events downstream of Jak phosphorylation have also been elucidated. For example, exposure of T lymphocytes to IL-2 has been shown to lead to the phosphorylation of signal transducers and activators of transcription (STAT) proteins STAT1α, STAT1β, and STAT3, as well as of two STAT-related proteins, p94 and p95. The STAT proteins were found to translocate to the nucleus and to bind to a specific DNA sequence, thus suggesting a mechanism by which IL-2 may activate specific genes involved in immune cell function (Frank et al. supra). Jak3 is associated with the gamma chain of the IL-2, IL-4, and IL-7 cytokine receptors (Fujii et al. (1995) Proc. Natl. Acad. Sci. 92:5482-5486) and (Musso et al. (1995) J. Exp. Med. 181:1425-1431). The Jak kinases have also been shown to be activated by numerous ligands that signal via cytokine receptors such as, growth hormone and erythropoietin and IL-6 (Kishimoto (1994) Stem cells Suppl. 12:37-44).

In a preferred embodiment the receptor element is a member of the nerve growth factor receptor superfamily, such as the Tumor necrosis factor α receptor. Tumor necrosis factor α (TNF-α or TNF-alpha) is a pleiotropic cytokine that is primarily produced by activated macrophages and lymphocytes; but is also expressed in endothelial cells and other cell types. TNF-alpha is a major mediator of inflammatory, immunological, and pathophysiological reactions. (Grell, M., et al., (1995) Cell, 83:793-802). Two distinct forms of TNF exist, a 26 kDa membrane expressed form and the soluble 17 kDa cytokine which is derived from proteolytic cleavage of the 26 kDa form. The soluble TNF polypeptide is 157 amino acids long and is the primary biologically active molecule.

TNF-alpha exerts its biological effects through interaction with high-affinity cell surface receptors. Two distinct membrane TNF-alpha receptors have been cloned and characterized. These are a 55 kDa species, designated p55 TNF-R and a 75 kDa species designated p75 TNF-R (Corcoran. A. E., et al., (1994) Eur. J. Biochem., 223:831-840). The two TNF receptors exhibit 28% similarity at the amino acid level. This is confined to the extracellular domain and consists of four repeating cysteine-rich motifs, each of approximately 40 amino acids. Each motif contains four to six cysteines in conserved positions. Dayhoff analysis shows the greatest intersubunit similarity among the first three repeats in each receptor. This characteristic structure is shared with a number of other receptors and cell surface molecules, which comprise the TNF-R/nerve growth factor receptor superfamily (Corcoran. A. E., et al., (1994) Eur. J. Biochem., 223:831-840).

TNF signaling is initiated by receptor clustering, either by the trivalent ligand TNF or by cross-linking monoclonal antibodies (Vandevoorde, V., et al., (1997) J. Cell Biol., 137: 1627-1638). Crystallographic studies of TNF and the structurally related cytokine, lymphotoxin (LT) have shown that both cytokines exist as homotrimers, with subunits packed edge to edge in a threefold symmetry. Structurally, neither TNF or LT reflect the repeating pattern of the their receptors. Each monomer is cone shaped and contains two hydrophilic loops on opposite sides of the base of the cone. Recent crystal structure determination of a p55 soluble TNF-R/LT complex has confirmed the hypothesis that loops from adjacent monomers join together to form a groove between monomers and that TNF-R binds in these grooves (Corcoran. A. E., et al., (1994) Eur. J. Biochem., 223:831-840).

In preferred embodiment, the receptor element is a receptor tyrosine kinase. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the EPH/ECK family contain cysteine-rich sequences (Hirai et al., (1987) Science 238: 1717-1720 and Lindberg and Hunter, (1990) Mol. Cell. Biol. 10:6316-6324). The functional domains of the kinase region of these three classes of receptor tyrosine kinases are encoded as a contiguous sequence (Hanks et al. (1988) Science 241: 42-52). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich (1988) supra and Hanks et al. (1988) supra).

The family with by far the largest number of known members is the EPH family. Since the description of the prototype, the EPH receptor (Hirai et al. (1987) Science 238:1717-1720), sequences have been reported for at least ten members of this family, not counting apparently orthologous receptors found in more than one species. Additional partial sequences, and the rate at which new members are still being reported, suggest the family is even larger (Maisonpierre et al. (1993) Oncogene 8:3277-3288; Andres et al. (1994) Oncogene 9:1461-1467; Henkemeyer et al. (1994) Oncogene 9:1001-1014; Ruiz et al. (1994) Mech. Dev. 46:87-100; Xu et al. (1994) Development 120:287-299; Zhou et al. (1994) J. Neurosci. Res. 37:129-143; and references in Tuzi and Gullick (1994) Br. J. Cancer 69:417-421). Remarkably, despite the large number of members in the EPH family, all of these molecules were identified as orphan receptors without known ligands.

As used herein, the terms "EPH receptor" or "EPH-type receptor" refer to a class of receptor tyrosine kinases, comprising at least eleven paralogous genes, though many more orthologs exist within this class, e.g. homologs from different species. EPH receptors, in general, are a discrete group of receptors related by homology and easily recognizable, e.g., they are typically characterized by an extracellular domain containing a characteristic spacing of cysteine residues near the N-terminus and two fibronectin type III repeats (Hirai et al. (1987) Science 238:1717-1720; Lindberg et al. (1990) Mol. Cell. Biol. 10:6316-6324; Chan et al. (1991) Oncogene 6:1057-1061; Maisonpierre et al. (1993) Oncogene 8:3277-3288; Andres et al. (1994) Oncogene 9:1461-1467; Henkemeyer et al. (1994) Oncogene 9:1001-1014; Ruiz et al. (1994) Mech. Dev. 46:87-100; Xu et al. (1994) Development 120: 287-299; Zhou et al. (1994) J. Neurosci. Res. 37:129-143; and references in Tuzi and Gullick (1994) Br. J. Cancer 69:417-421). Exemplary EPH receptors include the eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors.

In another embodiment the receptor element is a member of the hematopoietin receptor superfamily. Hematopoietin receptor superfamily is used herein to define single-pass transmembrane receptors, with a three-domain architecture: an extracellular domain that binds the activating ligand, a short transmembrane segment, and a domain residing in the cytoplasm. The extracellular domains of these receptors have low but significant homology within their extracellular ligand-binding domain comprising about 200-210 amino acids. The homologous region is characterized by four cysteine residues located in the N-terminal half of the region, and a Trp-Ser-X-Trp-Ser (WSXWS) motif located just outside the membrane-spanning domain. Further structural and functional details of these receptors are provided by Cosman, D. et al., (1990). The receptors of IL-1, IL-2, IL-3, IL-4, IL-5, IL-6, IL-7, prolactin, placental lactogen, growth hormone GM-CSF, G-CSF, M-CSF and erythropoietin have, for example, been identified as members of this receptor family.

In a further embodiment, the receptor element is an integrin other than Leukocyte Function Antigen-1 (LFA-1). Members of the integrin family of receptors function as heterodimers, composed of various α and β subunits, and mediate interactions between a cell's cytoskeleton and the extracellular matrix. (Reviewed in, Giancotti and Ruoslahti, Science 285, 13 Aug. 1999). Different combinations of the α and β subunits give rise to a wide range of ligand specificities, which may be increased further by the presence of cell-type-specific factors. Integrin clustering is know to activate a number of intracellular signals, such as RAS, MAP kinase, and phosphotidylinositol-3-kinase. In a preferred embodiment the receptor element is a heterodimer (other than LFA-1) composed of a β integrin and an α integrin chosen from the following integrins; β1, β2, β3, β4, β5, β6, α1, α2, α3, α4, α5, and α6, or is MAC-1 (β2 and cd11b), or αVβ3.

In a preferred embodiment, the receptor element is not the integrin LFA-1.

In an alternative embodiment, the receptor element is not an integrin.

In another embodiment the receptor elements cluster for signaling by contact with other surface molecules. In contrast to the receptors discussed above, these receptor elements cluster for signaling by contact with other surface molecules, and generally use molecules presented on the surface of a second cell as ligands. Receptors of this class are important in cell-cell interactions, such mediating cell to cell adhesion and immunorecognition.

Examples of such receptor elements are CD3 (T cell receptor complex), BCR (B cell receptor complex), CD4, CD28, CD80, CD86, CD54, CD102, CD50 and ICAMs 1, 2 and 3.

In a preferred embodiment the receptor element is a T cell receptor complex (TCR). TCRs occur as either of two distinct heterodimers, αβ or γδ, both of which are expressed with the non polymorphic CD3 polypeptides γ, δ, ε, ζ. The CD3 polypeptides, especially ζ and its variants, are critical for intracellular signaling. The αβ TCR heterodimer expressing cells predominate in most lymphoid compartments and are responsible for the classical helper or cytotoxic T cell responses. In most cases, the αβ TCR ligand is a peptide antigen bound to a class I or a class II MHC molecule (Fundamental Immunology, fourth edition, W. E. Paul, ed., Lippincott-Raven Publishers, 1999, Chapter 10, pp 341-367).

In a preferred embodiment the receptor element is a B cell antigen receptor (BCR). Antigen contact with a specific B cell triggers the transmembrane signaling function of the BCR. BCR molecules are rapidly internalized after antigen binding, leading to antigen uptake and degradation in endosomes or lysosomes. In the case of protein antigens, antigen-derived peptides bind in the groove of class II MHC molecules. Upon binding, this complex is sent to the cell surface, where it serves as a stimulus for specific helper T cells. Antigen recognition by the helper T cell induces it to form a tight and long lasting interaction with the B cell and to synthesize B cell growth and differentiation factors. B cells activated in this way may proliferate and terminally differentiate to antibody secreting cells (also called plasma cells) (Fundamental Immunology, fourth edition, W. E. Paul, ed., Lippincott-Raven Publishers, 1999, Chapters 6-7, pp 183-261)

In a preferred embodiment the receptor element is an intracellular adhesion molecule (ICAM). ICAMs-1, -2, and -3 are cellular adhesion molecules belonging to the immunoglobin superfamily. Each of these receptors has a single membrane-spanning domain and all bind to β2 integrins via extracellular binding domains similar in structure to Ig-loops. (Signal Transduction, Gomperts, et al., eds, Academic Press Publishers, 2002, Chapter 14, pp 318-319).

In a preferred embodiment the receptor elements are intracellular receptors capable of clustering. Receptors of this class are not membrane-bound, rather they are free to diffuse through the intracellular matrix where they bind soluble ligands prior to clustering and signal transduction. In contrast to the previously described receptors, many members of this class are capable of binding DNA after clustering to directly effect changes in RNA transcription.

In a preferred embodiment the intracellular receptors capable of clustering are peroxisome proliferator-activated receptors (PPAR). PPARs are soluble receptors responsive to lipophilic compounds, and induce various genes involved in fatty acid metabolism. The three PPAR subtypes, PPAR α, β, and γ have been shown to bind to DNA after ligand binding and heterodimerization with retinoid X receptor. (Summanasekera, et al., J Biol Chem, M211261200, Dec. 13, 2002.)

In another embodiment, the receptor element is a member of the large family of G-protein-coupled receptors. It has recently been reported that a G-protein-coupled receptors are capable of clustering. (Kroeger, et al., J Biol Chem 276:16, 12736-12743, Apr. 20, 2001; Bai, et al., J Biol Chem 273:36, 23605-23610, Sep. 4, 1998; Rocheville, et al., J Biol Chem 275 (11), 7862-7869, Mar. 17, 2000). As used herein G-protein-coupled receptor, and grammatical equivalents thereof, refers to the family of receptors that bind to heterotrimeric "G proteins." Many different G proteins are known to interact with receptors. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha (α), beta (β) and gamma (γ) subunits, are complexed with the nucleotide guanosine diphosphate (GDP) and are in contact with receptors. When a hormone or other first messenger binds to a receptor, the receptor changes conformation and this alters its interaction with the G protein. This spurs the α subunit to release GDP, and the more abundant nucleotide guanosine triphosphate (GTP), replaces it, activating the G protein. The G protein then dissociates to separate the α subunit from the still complexed beta and gamma subunits. Either the Gα subunit, or the Gβγ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the Gα converts the GTP to GDP, thereby inactivating itself. The inactivated Gα may then reassociate with the Gβγ complex.

Hundreds, if not thousands, of receptors convey messages through heterotrimeric G proteins, of which at least 17 distinct forms have been isolated. Although the greatest variability has been seen in the α subunit, several different β and γ structures have been reported. There are, additionally, many different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (1993) Cell 72, 415; Kouba et al. FEBS Lett. (1993)321, 173; and Birkenbach et al. (1993) J. Virol. 67, 2209.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, histamine, noradrenaline, tyramine/octopamine and other related compounds; peptides such as adrenocorticotrophic hormone (acth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin ii, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheromones, galanin, gastric inhibitory polypeptide receptor (gip), glucagon-like peptides (glps), glucagon, gonadotropin releasing hormone (gnrh), growth hormone releasing hormone (ghrh), insect diuretic hormone, interleukin-8, leutropin (1 h/hcg), met-enkephalin, opioid peptides, oxytocin, parathyroid hormone (pth) and pthrp, pituitary adenylyl cyclase activating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Preferred G protein coupled receptors include, but are not limited to: α1-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2a adenosine receptor, A2b adenosine receptor, A3 adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor (FPR), fMLP-like receptor (FPRL-1), angiotensin II type 1 receptor, endothelin ETA receptor, endothelin ETB receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, CXCR1 (IL-8 receptor A), CXCR2 (IL-8 receptor B), Delta Opioid receptor, Kappa Opioid receptor, mip-1alpha/RANTES receptor (CRR1), Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, melanocyte stimulating hormone receptor, antidiuretic hormone receptor, glucagon receptor, and adrenocorticotropic hormone II receptor. In addition, there are at least five receptors (CC and CXC receptors) involved in HIV viral attachment to cells. The two major co-receptors for HIV are CXCR4, (fusin receptor, LESTR, SDF1 receptor) and CCR5 (m-trophic). More preferred receptors include the following human receptors: melatonin receptor 1a, galanin receptor 1, neurotensin receptor, adenosine receptor 2a, somatostatin receptor 2 and corticotropin releasing factor receptor 1. Melatonin receptor 1a is particularly preferred. Other G protein coupled receptors (GPCRs) are known in the art.

The methods and compositions further provide for activating receptor elements by contacting the cell comprising the receptor elements with a binding element. As used herein, the term activating and grammatical equivalents thereof, is meant to include a step that induces a receptor element to become active. By active herein is meant a change in the isoform of the receptor resulting in either the turning on or turning off of a signal involved in a signaling pathway. A receptor element may be induced to become active either through: 1) the formation of clusters initiated by the binding of a binding element; or 2) directly through the binding of a binding element. For example, this step may take the form of administration of an extracellular signal, such as a small molecule, a change in temperature, or other alteration of the extracellular environment. In addition, this step may originate intracellularly and take the form of a change in transcription or translation rates.

In a preferred embodiment activation is achieved by the administration binding element, which can take the form of an extracellular signal. The term extracellular signal is intended to encompass molecules and changes in the environment that are transduced intracellularly via cell surface proteins that interact, directly or indirectly, with the extracellular signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels. The term, "extracellular signal" also includes as yet unidentified substances that modulate the activity of a cellular receptor, and thereby influence intracellular functions. Such extracellular signals are potential pharmacological agents that may be used to treat specific diseases by modulating the activity of specific cell surface receptors.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes.

In a preferred embodiment, the receptor element is activated to propagate a signal by clustering. In this embodiment, the binding element merely activates clustering of the receptor elements, while intermolecular interactions between the clustered receptor elements, e.g. the creation of disulfide bridges, ionic and polar interactions, etc., activates downstream signaling by the receptor. For example, receptor clustering can induce structural changes that result in the receptor gaining kinase or phosphotase activity.

By "binding element", and grammatical equivalents thereof, is meant any molecule, e.g., protein, small organic molecule, carbohydrates (including polysaccharides), polynucleotide, lipids, etc., as described below. Examples of binding elements are, transcription factors, mRNAs, tRNAs, cell surface receptors, proteinaceous and nonproteinaceous hormones as well as phospholipids, and sugars such as glucose and glycogen.

In a preferred embodiment binding elements are themselves activatable. As discussed in connection with activatable receptor elements, the binding element activator can take many forms, e.g. small molecules, proteins, nucleic acids, changes in extra- or intracellular conditions, etc.

In one embodiment, the BE is a protein, as used herein, the terms "protein" and "polypeptide" may be used interchangeably and mean at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradation. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

Aromatic amino acids may be replaced with D- or L-naphylalanine, D- or L-phenylglycine, D- or L-2-thienylalanine, D- or L-1-, 2-, 3- or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanines, and D- or L-alkylalanines where alkyl may be substituted or unsubstituted methyl, ethyl, propyl, hexyl, butyl, pentyl, isopropyl, iso-butyl, sec-isotyl, iso-pentyl, and non-acidic amino acids of C1-C20.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO3H) threonine, serine, or tyrosine.

Other substitutions may include nonnatural hydroxylated amino acids may made by combining "alkyl" with any natural amino acid. The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Alkyl includes heteroalkyl, with atoms of nitrogen, oxygen and sulfur. Preferred alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the variant polypeptides may be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant polypeptides of to the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues.

Other suitable reagents for derivatizing alpha-amino-containing residues include compounds such as imidoesters, e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues per se is well known, such as for introducing spectral labels into tyrosyl residues by reaction with aromatic diazonium compounds or tetranitromethane.

N-acetylimidizol and tetranitromethane may be used to form O-acetyl tyrosyl species and 3-nitro derivatives, respectively. Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

In an additional embodiment the BE is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more Carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made. Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As described above generally for proteins, nucleic acid BEs may be naturally occurring nucleic acids, random nucleic acids, or "biased" random nucleic acids. For example, digests of prokaryotic or eukaryotic genomes may be used as is outlined above for proteins. Where the ultimate expression product is a nucleic acid, at least 10, preferably at least 12, more preferably at least 15, most preferably at least 21 nucleotide positions need to be randomized, with more preferable if the randomization is less than perfect. Similarly, at least 5, preferably at least 6, more preferably at least 7 amino acid positions need to be randomized; again, more are preferable if the randomization is less than perfect.

In a preferred embodiment, the BE is a mutant cDNA encoding a catalytically inactive polypeptide. Examples of such catalytically inactive polypeptides include, but are not limited to, catalytically inactive activatable proteins and, more specifically, catalytically inactive kinases (e.g., PI3K) or caspases.

In a preferred embodiment, the BE is an RNA, for example an antisense RNA or siRNA (small inhibitory RNA). In another preferred embodiment, the siRNA cleaves RNA encoding an activatable protein. The siRNAs can be prepared using the methods described herein and known in the art.

In a preferred embodiment, the BEs are synthetic compounds. Any number of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

Alternatively, a preferred embodiment utilizes natural compounds, as BEs, in the form of bacterial, fungal, plant and animal extracts that are available or readily produced.

Additionally, natural or synthetically produced compounds are readily modified through conventional chemical, physical and biochemical means. Known pharmacological agents may be subjected to directed or random chemical modifications, including enzymatic modifications, to produce BEs that may be used in the instant invention.

In another preferred embodiment the BE is a small organic compound. BEs can synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracyclines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or BEs which can then be used in the present invention.

In a preferred embodiment the BE is a carbohydrate. As used herein the term carbohydrate is meant to include any compound with the general formula $(CH_2O)_n$. Examples of preferred carbohydrates are di-, tri- and oligosaccharides, as well polysaccharides such as glycogen, cellulose, and starches.

In a preferred embodiment the BE is a lipid. As used herein the term lipid herein is meant to include any water insoluble organic molecule that is soluble in nonpolar organic solvents. Examples of preferred lipids are steroids, such as cholesterol, and phospholipids such as sphingomyelin.

As discussed above, the instant invention provides methods and compositions for the detection of the clustering and activation of receptor elements in cells. As used herein the term cells and grammatical equivalents herein in meant any cell, preferably any prokaryotic or eukaryotic cell.

Suitable prokaryotic cells include, but are not limited to, bacteria such as *E. coli*, various *Bacillus* species, and the extremophile bacteria such as thermophiles, etc.

Suitable eukaryotic cells include, but are not limited to, fungi such as yeast and filamentous fungi, including species of *Aspergillus, Trichoderma*, and *Neurospora*; plant cells including those of corn, sorghum, tobacco, canola, soybean, cotton, tomato, potato, alfalfa, sunflower, etc.; and animal cells, including fish, birds and mammals. Suitable fish cells include, but are not limited to, those from species of salmon, trout, tulapia, tuna, carp, flounder, halibut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes.

Suitable cells also include cell types implicated in a wide variety of disease conditions are particularly. Accordingly, suitable eukaryotic cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, COS, etc. See the ATCC cell line catalog, hereby expressly incorporated by reference.

In one embodiment, the cells may be genetically engineered, that is, contain exogeneous nucleic acid There are a number of widely available assays to detect either the clustering or activation in a cell. For example, to detect clustering, receptor element ligands and/or receptor-specific antibodies can be labeled, and these labels detected to visualize clustering of receptor elements. In one example of this type of assay, a cell comprising the receptor element of interest is contacted with a receptor-specific mouse antibody. The receptor-specific mouse antibody is then labeled by the addition of TRITC-conjugated donkey anti-mouse antibody. Using confocal scanning laser microscopy, fluorescence emitted from the TRITC can be detected to identify the location of the receptor elements. (Van Steensel, et al., J Cell Sci 108, 3003-3011, 1995).

In another technique, the receptor of interest is labeled directly and the label is detected as an indication of clustering. For example, the coding region of a particular receptor element can be fused to the coding sequence of Green Fluorescent Protein (GFP), and the resultant fusion protein is then expressed in a cell. Using confocal scanning laser microscopy, fluorescence emitted by the GFP can be detected to identify the location of the receptor elements. (Gensler, et al., Eur. J. Biochem. 268, 2209-2217, 2001)

A receptor element may also be labeled with one member of a label pair, wherein clustering of that receptor with a receptor labeled with the other member of the label pair is required for detection of the label pair. For example, in bioluminescence resonance transfer, the coding sequence of the receptor element may be fused with either donor *Renilla* luciferase or acceptor enhanced yellow fluorescence protein. In situations where homodimer or homo-oligomerization is suspected, two or more coding sequences of the same receptor will be used, one fused to donor *Renilla* luciferase, and one fused to acceptor enhanced yellow fluorescence protein. If necessary, further coding sequences can be fused to'other known acceptor proteins, such as GFP. In situations where heterodimerization or hetero-oligomerization is suspected, the coding sequence of the first receptor element is fused to donor *Renilla* luciferase and the coding sequence of the second receptor element is fused to acceptor enhanced yellow fluorescence protein. Again, If necessary, further coding sequences can be fused to other known acceptor proteins, such as GFP. Using confocal laser microscopy, fluorescence emitted by the acceptor protein can be detected to identify clustering of the receptor elements. (Kroeger, et al., J Biol Chem 276:16, 12736-12743, Apr. 20, 2001).

As will be appreciated by one of skill in the art, the ability of a receptor to cluster can be determined using any of the above techniques, in addition to other techniques known in the art.

The methods and compositions of the instant invention provide BEs which comprise a label or tag. By label is meant a molecule that can be directly (i.e., a primary label) or indirectly (i.e., a secondary label) detected; for example a label can be visualized and/or measured or otherwise identified so that its presence or absence can be known. A compound can be directly or indirectly conjugated to a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. Preferred labels include, but are not limited to, fluorescent labels, label enzymes and radioisotopes.

In general, labels fall into four classes: a) isotopic labels, which may be radioactive or heavy isotopes; b) magnetic, electrical, thermal labels; c) colored or luminescent dyes or moieties; and d) binding partners. Labels can also include enzymes (horseradish peroxidase, etc.) and magnetic particles. In a preferred embodiment, the detection label is a primary label. A primary label is one that can be directly detected, such as a fluorophore.

Preferred labels include chromophores or phosphors but are preferably fluorescent dyes or moieties. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263 (5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), β-galactosidase (Nolan, et al., Proc Natl Acad Sci USA 85(8):2603-2607 (April 1988)) and *Renilla* WO 92/15673; WO 95/07463; WO 98/14605; WO 98/26277; WO 99/49019; U.S. Pat. Nos. 5,292,658; 5,418,155; 5,683,888; 5,741,668; 5,777,079; 5,804,387; 5,874,304; 5,876,995; and 5,925,558). All of the above-cited references are expressly incorporated herein by reference.

Particularly preferred labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC can be found at drmr.com/abcon Quantitation of fluorescent probe conjugation may be assessed to determine degree of labeling and protocols including dye spectral properties can be found at metazoa.com/UPL3419.

In another preferred embodiment, the fluorescent label is a GFP and, more preferably, a *renilla, ptilosarcus*, or *aequorea* species of GFP.

In a preferred embodiment, a secondary detectable label is used. A secondary label is one that is indirectly detected; for example, a secondary label can bind or react with a primary label for detection, can act on an additional product to generate a primary label (e.g. enzymes), etc. Secondary labels include, but are not limited to, one of a binding partner pair; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. For example, suitable binding partner pairs include, but are not limited to: antigens (such as proteins (including peptides) and small molecules) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises an antigen and an antibody that will specifically bind to the antigen. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

In a preferred embodiment, the secondary label is a chemically modifiable moiety. In this embodiment, labels comprising reactive functional groups are incorporated into the molecule to be labeled. The functional group can then be subsequently labeled (e.g. either before or after the assay) with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or heterobifunctional linkers as are well known (see 1994 Pierce Chemical Company catalog, technical section on cross-linkers, pages 155-200, incorporated herein by reference).

In preferred embodiments, multiple fluorescent labels are employed in the methods and compositions of the present invention. In a preferred embodiment, at least two fluorescent labels are used which are members of a fluorescence resonance energy transfer (FRET) pair.

FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Förster radius (Ro), which is typically 10-100 Å. Changes in the fluorescence emission spectrum comprising FRET pairs can be detected, indicating changes in the number of that are in close proximity (i.e., within 100 Å of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescien, IAEDANS/fluorescein, fluorescein/tetramethylrhodamine, fluorescein/LC Red 640, fluorescein/Cy 5, fluorescein/Cy 5.5 and fluorescein/LC Red 705.

In another aspect of FRET, a fluorescent donor molecule and a nonfluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, TAMRA, DABCYL, QSY 7 and QSY 33. Useful fluorescent donor/quencher pairs include, but are not limited to EDANS/ DABCYL, Texas Red/DABCYL, BODIPY/DABCYL, Lucifer yellow/DABCYL, coumarin/DABCYL and fluorescein/ QSY 7 dye.

The skilled artisan will appreciate that FRET and fluorescence quenching allow for monitoring of binding of labeled molecules over time, providing continuous information regarding the time course of binding reactions.

Preferably, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The ratio-metric fluorescent reporter system described herein has significant advantages over existing reporters for protein integration analysis, as it allows sensitive detection and isolation of both expressing and non-expressing single living cells. In a preferred embodiment, the assay system uses a non-toxic, non-polar fluorescent substrate which is easily loaded and then trapped intracellularly. Modification of the fluorescent substrate by a cognate protein yields a fluorescent emission shift as substrate is converted to product. Because the reporter readout is ratiometric it is unique among reporter protein assays in that it controls for variables such as the amount of substrate loaded into individual cells. The stable, easily detected, intracellular readout eliminates the need for establishing clonal cell lines prior to expression analysis. This system and other analogous flow sorting systems can be used to isolate cells having a particular receptor element clustering and/or activation profile from pools of millions of viable cells.

The methods and composition of the present invention may also make use of label enzymes. By label enzyme is meant an enzyme which may be reacted in the presence of a label enzyme substrate which produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6-9 (1998), Young, J. Virol. Methods 24:227-236 (1989), which are each hereby incorporated by reference in their entirety.

By radioisotope is meant any radioactive molecule. Suitable radioisotopes for use in the invention include, but are not limited to $^{14}C$, $^{3}H$, $^{32}P$, $^{33}P$, $^{35}S$, $^{125}I$, and $^{131}I$. The use of radioisotopes as labels is well known in the art.

As mentioned, labels may be indirectly detected, that is, the tag is a partner of a binding pair. By "partner of a binding pair" is meant one of a first and a second moiety, wherein the first and the second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avid (or biotin/streptavidin) and calmodulin binding protein (CBP)/calmodulin. Other suitable binding pairs include polypeptides such as the FLAG-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)] and the antibodies each thereto. As will be appreciated by those in the art, binding pair partners may be used in applications other than for labeling, as is described herein.

As will be appreciated by those in the art, a partner of one binding pair may also be a partner of another binding pair. For example, an antigen (first moiety) may bind to a first antibody (second moiety) which may, in turn, be an antigen for a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag which is a partner of a binding pair, as just described, is referred to herein as "indirect labeling".

By "surface substrate binding molecule" or "attachment tag" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate [Field et al., Mol. Cell. Biol., 8:2159-2165 (1988)]; the c-myc tag and the 8F9, 3C7, 6E10, G4, B7 and 9E10 antibody substrates thereto [Evan et al., Molecular and Cellular Biology, 5:3610-3616 (1985)]; and the Herpes Simplex virus glycoprotein D (gD) tag and its antibody substrate [Paborsky et al., Protein Engineering, 3(6):547-553 (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of antibody-embedded substrates is well known; see Slinkin at al., Bioconj. Chem. 2:342-348 (1991); Torchilin et al., supra; Trubetskoy at al., Bioconj. Chem. 3:323-327 (1992); King et al., Cancer Res. 54:6176-6185 (1994); and Wilbur et al., Bioconjugate Chem. 5:220-235 (1994) (all of which are hereby expressly incorporated by reference), and attachment of or production of proteins with antigens is described above. Calmodulin-embedded substrates are commercially available, and production of proteins with CBP is described in Simcox et al., Strategies 8:40-43 (1995), which is hereby incorporated by reference in its entirety.

As will be appreciated by those in the art, tag-components of the invention can be made in various ways, depending largely upon the form of the tag. Components of the invention and tags are preferably attached by a covalent bond.

The production of tag-polypeptides by recombinant means when the tag is also a polypeptide is described below. Production of tag-labeled proteins is well known in the art and kits for such production are commercially available (for example, from Kodak and Sigma). Examples of tag labeled proteins include, but are not limited to, a Flag-polypeptide and His-polypeptide. Methods for the production and use of tag-labeled proteins are found, for example, in Winston et al., Genes and Devel. 13:270-283 (1999), incorporated herein in its entirety, as well as product handbooks provided with the above-mentioned kits.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known (Id.).

Methods for labeling of proteins with radioisotopes are known in the art. For example, such methods are found in Ohta et al., Molec. Cell 3:535-541 (1999), which is hereby incorporated by reference in its entirety.

Production of proteins having tags by recombinant means is well known, and kits for producing such proteins are commercially available. For example, such a kit and its use is described in the QIAexpress Handbook from Qiagen by Joanne Crowe et al., hereby expressly incorporated by reference.

The functionalization of labels with chemically reactive groups such as thiols, amines, carboxyls, etc. is generally known in the art. In a preferred embodiment, the tag is functionalized to facilitate covalent attachment. The covalent attachment of the tag may be either direct or via a linker. In one embodiment, the linker is a relatively short coupling moiety, that is used to attach the molecules. A coupling moiety may be synthesized directly onto a component of the invention and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In a preferred embodiment, the covalent attachment is direct, that is, no linker is used. In this embodiment, the component preferably contains a functional group such as a carboxylic acid which is used for direct attachment to the functionalized tag. It should be understood that the component and tag may be attached in a variety of ways, including those listed above. In a preferred embodiment, the tag is attached to the amino or carboxyl terminus of the polypeptide. As will be appreciated by those in the art, the above description of the covalent attachment of a label applies to the attachment of virtually any two molecules of the present disclosure.

In a preferred embodiment, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above or a component of the invention. Thus, for example, for direct linkage to a carboxylic acid group of a protein, amino modified or hydrazine modified tags will be used for coupling via carbodiimide chemistry, for example using 1-ethyl-3-(3-dimethylaminopropyl)-carbodiimide (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the tag, such as is commercially available for many of the tags described herein.

Antibody conjugation may be performed using standard procedures (drmr.com.abcon) or by using protein-protein/protein-dye crosslinking kits from Molecular Probes (Eugene, Oreg.).

In an additional embodiment, the invention provides an activation state-specific antibody. The methods and compositions of the present invention may be used to detect any particular receptor element isoform in a sample that is antigenically detectable and antigenically distinguishable from other isoforms of the receptor element which are present in the sample. For example, as demonstrated (see, e.g., the Examples) and described herein, the activation state-specific antibodies of the present invention can be used in the present methods to identify distinct signaling cascades of a subset or subpopulation of complex cell populations; and the ordering of protein activation (e.g., kinase activation) in potential signaling hierarchies. Further, in the methods of the present invention, the use of flow cytometry, particularly polychromatic flow cytometry, permits the multi-dimensional analysis and functional assessment of the signaling pathway in single cells.

As used herein, the term "activation state-specific antibody" or "activation state antibody" or grammatical equivalents thereof, refer to an antibody that specifically binds to a corresponding and specific antigen. Preferably, the corresponding and specific antigen is a specific isoform of an activable receptor element. Also preferably, the binding of the activation state-specific antibody is indicative of a specific activation state of a specific activatable receptor element.

Thus, in preferred embodiments, the binding of an activation state-specific antibody to a corresponding isoform of an activable receptor element is indicative of the identity of the activatable receptor element and of the activation state of the activatable receptor element.

In a preferred embodiment, the activation state-specific antibody is a peptide comprising a recognition structure that binds to a target structure on an activatable receptor element. A variety of recognition structures are well known in the art and can be made using methods known in the art, including by phage display libraries (see e.g., Gururaja et al. Chem. Biol. (2000) 7:515-27; Houimel et al., Eur. J. Immunol. (2001) 31:3535-45; Cochran et al. J. Am. Chem. Soc. (2001) 123: 625-32; Houimel et al. Int. J. Cancer (2001) 92:748-55, each incorporated herein by reference). In a preferred embodiment, the activation state-specific antibody comprises the following recognition structure: SKVILFE--random peptide loop---SKVILFE. Antibodies having such recognition structures can bind with high affinity to specific target structures. Further, fluorophores can be attached to such antibodies for use in the methods of the present invention.

A variety of recognitions structures are known in the art (e.g., Cochran et al., J. Am. Chem. Soc. (2001) 123:625-32; Boer et al., Blood (2002) 100:467-73, each expressly incorporated herein by reference)) and can be produced using methods known in the art (see e.g., Boer et al., Blood (2002)

100:467-73; Gualillo et al., Mol. Cell. Endocrinol. (2002) 190:83-9, each expressly incorporated herein by reference)), including for example combinatorial chemistry methods for producing recognition structures such as polymers with affinity for a target structure on an activable protein (see e.g., Barn at al., J. Comb. Chem. (2001) 3:534-41; Ju et al., Biotechnol. (1999) 64:232-9, each expressly incorporated herein by reference). In another preferred embodiment, the activation state-specific antibody is a protein that only binds to an isoform of a specific activatable receptor element that is phosphorylated and does not bind to the isoform of this activable receptor element when it is not phosphorylated or nonphosphorylated. In another preferred embodiment the activation state-specific antibody is a protein that only binds to an isoform of an activatable receptor element that is intracellular and not extracellular, or vice versa.

In a preferred embodiment, the recognition structure is an anti-laminin single-chain antibody fragment (scFv) (see e.g., Sanz et al., Gene Therapy (2002) 9:1049-53; Tse at al., J. Mol. Biol. (2002) 317:85-94, each expressly incorporated herein by reference).

As used herein, an "activatable receptor element" or "substrate" or grammatical equivalents thereof, refers to a receptor element that has at least one isoform (and in some cases two or more isoforms) that corresponds to a specific form of the receptor element having a particular biological, biochemical, or physical property, e.g., an enzymatic activity, a modification (e.g., post-translational modification), or a conformation. The activable receptor element can be activated or nonactivated with respect to a particular biological activity, modification, or conformation. Specifically, the "activated" or "active" form of the activatable receptor element has the particular biological activity, modification, or conformation; whereas the "non-activated" or "non-active" form of the activatable receptor element does not have (or has a lesser or diminished level of) the particular biological activity, modification, or conformation, respectively. In some embodiments, there may be more than one isoform associated with activity or activation state; for example, there may be an isoform associated with an "open" conformation available for substrate binding, a second "transition state" isoform, and an isoform devoid of activity (e.g., where the activity is inhibited).

In a preferred embodiment, the biological, biochemical, or physical property (e.g. enzymatic activity, modification, or conformation) of the activatable receptor element is inducible or "activatable" by an activating agent or by cell signaling events. Examples of activating agents include, but are not limited to, kinases, phosphatases, proteases (e.g., caspases), and hormones. Examples of cell signaling events include, but are not limited to, receptor clustering or binding of a cognate molecule or ligand.

As used herein, an "isoform" or grammatical equivalents thereof, refers to a form of an activatable receptor having a specific, and preferably detectable, biological activity, modification, or conformation. The isoform can be an activated (or active) form, or non-activated (or not active) form of an activatable receptor. As mentioned, in preferred embodiments, the binding of an activation state-specific antibody to a corresponding isoform of an activable receptor element is indicative of the identity of the activatable receptor element and of the activation state of the activatable receptor element. In a preferred embodiment, the invention provides methods for determining a receptor element isoform profile which comprise determining the presence of an isoform of an activatable receptor element that is activated (or activated isoform).

In a preferred embodiment, the activated isoform or activated state of an activable receptor element is a form of the activable receptor having a particular or specific biological, biochemical, or physical property that is not possessed by at least one other isoform of activatable receptor element. Examples of such properties include, but are not limited to, enzymatic activity (e.g., kinase activity and protease activity), and receptor element binding activity. Thus, such particular or specific properties or activities are associated with an activated isoform of an activatable receptor element. Such properties or activities are sometimes referred to herein as activation state activities.

An example of activation state activity is kinase activity for an activated receptor element. As used herein, a receptor element with protein kinase activity may refer to a receptor element that when activated is capable of catalyzing the phosphorylation of amino acids, or derivatives thereof, which possess an hydroxyl group. Preferred kinases are those which are capable of catalyzing the phosphorylation of serine, threonine, and tyrosine residues. Kinase activity may be determined by supplying a substrate for phosphorylation by kinase, a source of phosphate usable by kinase, and determining the phosphorylation of substrate in the presence of kinase.

Another example of activation state activity is protease activity for an activated receptor element. As used herein, a receptor element with protease activity may refer to a receptor element that when activated is capable of hydrolyzing a peptide bond within a polypeptide comprising an amino acid sequence.

The antigenicity of an activated isoform of an activatable receptor element is distinguishable from the antigenicity of non-activated isoform of an activatable receptor element or from the antigenicity of an isoform of a different activation state. In a preferred embodiment, an activated isoform of a receptor element possesses an epitope that is absent in a non-activated isoform of a receptor element, or vice versa. In another preferred embodiment, this difference is due to covalent addition of moieties to a receptor element, such as phosphate moieties, or due to a structural change in a receptor element, as through protein cleavage, or due to an otherwise induced conformational change in a receptor element which causes the element to present the same sequence in an antigenically distinguishable way. In another preferred embodiment, such a conformational change causes an activated isoform of a receptor element to present at least one epitope that is not present in a non-activated isoform, or to not present at least one epitope that is presented by a non-activated isoform of the element. In some embodiments, the epitopes for the distinguishing antibodies are centered around the active site of the receptor element, although as is known in the art, conformational changes in one area of a receptor element may cause alterations in different areas of the element as well.

Many antibodies, many of which are commercially available (for example, see Cell Signaling Technology, www.cellsignal.com, the contents which are incorporated herein by reference). have been produced which specifically bind to the phosphorylated isoform of a protein but do not specifically bind to a non-phosphorylated isoform of a protein. Many such antibodies have been produced for the study of signal transducing proteins which are reversibly phosphorylated. Particularly, many such antibodies have been produced which specifically bind to phosphorylated, activated isoforms of protein kinases and are sometimes referred to herein as kinase activation state antibodies or grammatical equivalents thereof. Particularly preferred antibodies for use in the present invention include: phospho-AKT Ser473 monoclonal anti-4E2, phospho-p44/42 MAP kinase (Thr202/Tyr204)

monoclonal antibody, phospho-TYK2 (Tyr1054/1055) antibody, phospho-p38 MAP kinase (Thr180/Tyr182) monoclonal antibody 28B10, phospho-PKC-PAN substrate antibody, phospho-PKA-substrate, phospho-SAPK/JNK (Thr183/Tyr185) G9 monoclonal antibody, phospho-tyrosine monoclonal antibody (P-tyr-100), p44/42 MAPK, p38 MAPK, JNK/SAPK, and phospho-AKT-Thr308.

The present invention provides methods for the determination of a receptor element with kinase activity activation state profile for a sample which comprise simultaneously determining the presence of activated isoforms of a multiplicity of receptor elements using a multiplicity of antibodies that specifically bind to active, phosphorylated isoforms of the multiplicity of receptor elements.

Additional means for determining kinase activation are provided by the present invention. Substrates that are specifically recognized by protein kinases and phosphorylated thereby are known. Antibodies that specifically bind to such phosphorylated substrates but do not bind to such non-phosphorylated substrates (phospho-substrate antibodies) may be used to determine the presence of activated kinase in a sample.

In a further embodiment, a receptor element activation and profile is determined using a multiplicity of activation state antibodies that are immobilized. Antibodies may be non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes, and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. In some cases magnetic beads and the like are included.

The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the antibody on the surface, etc. Following binding of the antibody, excess unbound material is removed by washing. The sample receiving areas may then be blocked through incubation with bovine serum albumin (BSA), casein or other innocuous protein or other moiety.

In a preferred embodiment, an epitope-recognizing fragment of an activation state antibody rather than the whole antibody is used. In another preferred embodiment, the epitope-recognizing fragment is immobilized. In another preferred embodiment, the antibody light chain which recognizes an epitope is used. A recombinant nucleic acid encoding a light chain gene product which recognizes an epitope may be used to produce such an antibody fragment by recombinant means well known in the art.

Using the example of two activation state specific antibodies, by "uniquely labeled" is meant that a first activation state antibody recognizing a first activated receptor element comprises a first label, and second activation state antibody recognizing a second activated receptor element comprises a second label, wherein the first and second label are detectable and distinguishable, making the first antibody and the second antibody uniquely labeled.

Non-activation state antibodies may also be used in the present invention. In a preferred embodiment, non-activation state antibodies bind to epitopes in both activated and non-activated forms of a receptor element. Such antibodies may be used to determine the amount of non-activated plus activated receptor in a sample. In another preferred embodiment, non-activation state antibodies bind to epitopes present in non-activated forms of a receptor but absent in activated forms of a receptor. Such antibodies may be used to determine the amount of non-activated receptor in a sample. Both types of non-activation state antibodies may be used to determine if a change in the amount of activation state receptor, for example from samples before and after treatment with a candidate bioactive agent as described herein, coincide with changes in the amount of non-activation state receptor. For example, such antibodies can be used to determine whether an increase in activated receptor is due to activation of non-activation state receptor, or due to increased expression of the receptor, or both.

In another preferred embodiment, antibodies are immobilized using beads analogous to those known and used for standardization in flow cytometry. Attachment of a multiplicity of activation state specific antibodies to beads may be done by methods known in the art and/or described herein. Such conjugated beads may be contacted with sample, preferably cell extract, under conditions which allow for a multiplicity of activated receptor elements, if present, to bind to the multiplicity of immobilized antibodies. A second multiplicity of antibodies comprising non-activation state antibodies which are uniquely labeled may be added to the immobilized activation state specific antibody-activated receptor complex and the beads may be sorted by FACS on the basis of the presence of each label, wherein the presence of label indicates binding of corresponding second antibody and the presence of corresponding activated receptor.

In a preferred embodiment, the present invention provides methods for determining a receptor element's clustering and/or activation state profile for a single cell. The methods comprise sorting cells by FACS on the basis of the activation state of at least two receptor elements. Activation state-specific antibodies are used to sort cells on the basis of receptor element activation state.

When using fluorescent labeled components in the methods and compositions of the present invention, it will recognized that different types of fluorescent monitoring systems, e.g., FACS systems, can be used to practice the invention. Preferably, FACS systems are used or systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation which has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation.

A chip analogous to a DNA chip can be used in the methods of the present invention. Arrayers and methods for spotting nucleic acid to a chip in a prefigured array are known. In addition, protein chips and methods for synthesis are known. These methods and materials may be adapted for the purpose of affixing activation state antibodies to a chip in a prefigured array.

In a preferred embodiment, such a chip comprises a multiplicity of receptor element activation state antibodies, and is used to determine a receptor element activation state profile for a sample. In a preferred embodiment, such a sample is a cell extract. In such a method, detection of activated receptor elements is by "sandwich assay" as known in the art. Briefly, a sample, preferably a cell extract, is passed over a the chip under conditions which allow the multiplicity of immobilized receptor element activation state antibodies to simultaneously bind to a multiplicity of activated receptor elements if present in the sample. The immobilized antibody-receptor element complex is optionally washed and contacted with a second plurality of antibodies comprising non-activation state antibodies that are capable of specifically binding to activated receptor elements while the elements are specifically bound to receptor element activation state specific antibodies. Such non-activation state specific antibodies specifically bind to activated receptor elements via an epitope that is not recognized by the receptor element activation state specific antibody. Binding of the non-activation state specific antibodies to the activation state antibody-activated receptor element complex is determined and reveals the presence of activated receptor element in sample. As will be appreciated, the determination of binding of second antibody in the sandwich assay can be accomplished in many different ways. Preferably, the multiplicity of non-activation state specific antibodies are uniquely labeled to facilitate detection.

In an alternative embodiment, a chip comprises a multiplicity of non-activation state specific antibodies. Such a chip is contacted with sample, preferably cell extract, and a second multiplicity of antibodies comprising receptor element activation state specific antibodies is used in the sandwich assay to simultaneously determine the presence of a multiplicity of activated receptor elements in sample. Preferably, the multiplicity of activation state specific antibodies are uniquely labeled to facilitate detection.

In a preferred embodiment, flow cytometry is used to detect fluorescence. Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remacle et al., Proc. Natl. Sci. USA (2000) 18:553-8, each expressly incorporated herein by reference).

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety FACS systems are known in the art and can be used in the methods of the invention (see e.g., WO99/54494, filed Apr. 16, 1999; U.S.A.N. 20010006787, filed Jul. 5, 2001, each expressly incorporated herein by reference).

In a preferred embodiment, a FACS cell sorter (e.g. a FACSVantage™ Cell Sorter, Becton Dickinson Immunocytometry Systems, San Jose, Calif.) is used to sort and collect cells based on their receptor element clustering and/or activation profile (positive cells). The cells are first contacted with fluorescent-labeled activation state-specific antibodies directed against specific isoforms of specific activatable receptor elements. In one embodiment, the amount of bound antibody on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell sorting procedures are described in detail, for example, in the FACSVantage™ Training Manual, with particular reference to sections 3-11 to 3-28 and 10-1 to 10-17.

In another embodiment, positive cells can be sorted using magnetic separation of cells based on the presence of an isoform of an activatable receptor element. In such separation techniques, cells to be positively selected are first contacted with specific binding element (e.g., an antibody or reagent that binds an isoform of an activatable protein). The cells are then contacted with retrievable particles (e.g., magnetically responsive particles) which are coupled with a reagent that binds the specific binding element. The cell-binding element-particle complex can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual.

In a preferred embodiment, methods for the determination of a receptor element activation state profile for a single cell are provided. The methods comprise providing a population of cells and sorting the population of cells by FACS. Preferably, cells are separated on the basis of the activation state of at least two receptor elements. In a preferred embodiment, a multiplicity of receptor element activation state antibodies (sometimes referred to herein as receptor activation state specific antibodies) are used to simultaneously determine the activation state of a multiplicity of receptor elements.

In a preferred embodiment, cell sorting by FACS on the basis of the activation state of at least two receptor elements is combined with a determination of other FACS readable outputs, such as the presence of surface markers, granularity and cell size to provide a correlation between the activation state of a multiplicity of receptor elements and other cell qualities measurable by FACS for single cells.

As will be appreciated, the present invention also provides for the ordering of receptor element clustering and activation events in signal transduction. Particularly, the present invention allows the artisan to construct a receptor element clustering and activation hierarchy based on the correlation of levels of clustering and activation of a multiplicity of receptor elements within single cells.

The present invention may also be used to determine the presence of cellular subsets, based on correlated receptor element activation within complex cellular mixtures such as peripheral blood mononuclear cells. These subsets may represent different differentiation or activation states or different cell lineages or sublineages.

It will also be recognized that a homogeneous cell population is desirable for studying signal transduction in order that variances in signaling between cells not qualitatively and quantitatively mask signal transduction events. The ultimate homogeneous system is the single cell. The present invention provides methods for the analysis of signal transduction in single cells, where the activated state of the signal transducing receptor element involved is antigenically distinguishable from a non-activated state.

As will be appreciated, these methods provide for the identification of distinct signaling cascades for both artificial and stimulatory conditions in complex cell populations, such a peripheral blood mononuclear cells, or naive and memory lymphocytes.

The methods provided herein may also involve the use of specific inhibitors of particular receptor elements. The methods provided herein may also involve the use of other pharmacological inhibitors of signaling pathways. These inhibitors may be used as controls to ensure that antibodies specifically bind to activated isoforms of receptor elements. For example, an inhibitor of a receptor element known to phosphorylate and activate a kinase may be used to inhibit phosphorylation of the kinase and examine whether an antibody specifically recognizes a phosphorylated isoform of the kinase. Alternatively, the inhibitors may be used to further probe signaling pathways and correlations in protein activity, particularly in single cells.

In a preferred embodiment, a method for screening for a bioactive agent capable of modulating receptor element clustering and activity is provided which comprises contacting a cell with a candidate bioactive agent and determining receptor element activation in said cell by cell sorting said cell by FACS.

In a preferred embodiment, the method comprises contacting a plurality of cells with a plurality of candidate bioactive agents and sorting the cells by FACS on the basis of the clustering and activation of at least one receptor element.

By "candidate bioactive agent", "candidate agent", "candidate modulator", "candidate modulating agent", or "exogeneous compound" or grammatical equivalents herein is meant any molecule, e.g., protein, small organic molecule, carbohydrates (including polysaccharides), polynucleotide, lipids, etc. Generally a plurality of assay mixtures can be run in parallel with different agent concentrations to obtain a differential response to the various concentrations. Typically, one of these concentrations can serve as a negative control, i.e., at zero concentration or below the level of detection. In addition, positive controls can be used.

Candidate agents encompass numerous chemical classes. In a preferred embodiment, the candidate agents are small molecules. In another preferred embodiment, the candidate agents are organic molecules, particularly small organic molecules, comprising functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more chemical functional groups.

Candidate agents are obtained from a wide variety of sources, as will be appreciated by those in the art, including libraries of synthetic or natural compounds. As will be appreciated by those in the art, the present invention provides a rapid and easy method for screening any library of candidate modulators, including the wide variety of known combinatorial chemistry-type libraries.

In a preferred embodiment, candidate agents are synthetic compounds, as described above in connection with binding elements. One advantage of the present method is that it is not necessary to characterize the candidate agent prior to the assay. Using the methods of the present invention, any candidate agents can be screened for the ability to modulate (e.g., increase or decease) the activity of an activatable protein. In addition, as is known in the art, coding tags using split synthesis reactions may be used to essentially identify the chemical moieties tested.

Alternatively, a preferred embodiment utilizes libraries of natural compounds, as candidate agents, in the form of bacterial, fungal, plant and animal extracts that are available or readily produced.

Additionally, natural or synthetically produced libraries and compounds are readily modified through conventional chemical, physical and biochemical means. Known pharmacological agents may be subjected to directed or random chemical modifications, including enzymatic modifications, to produce structural analogs.

In a preferred embodiment, candidate agents include proteins, nucleic acids, and chemical moieties.

In a preferred embodiment, the candidate agents are proteins, as defined above. In a preferred embodiment, the candidate agents are naturally occurring proteins or fragments of naturally occurring proteins. Thus, for example, cellular extracts containing proteins, or random or directed digests of proteinaceous cellular extracts, may be tested, as is more fully described below. In this way libraries of prokaryotic and eukaryotic proteins may be made for screening against any number of candidate agents. Particularly preferred in this embodiment are libraries of bacterial, fungal, viral, and mammalian proteins, with the latter being preferred, and human proteins being especially preferred.

In a preferred embodiment, the candidate agents are peptides of from about 2 to about 50 amino acids, with from about 5 to about 30 amino acids being preferred, and from about 8 to about 20 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

The library should provide a sufficiently structurally diverse population of randomized agents to effect a probabilistically sufficient range of diversity to allow interaction with a particular activatable protein. Accordingly, an interaction library must be large enough so that at least one of its members will have a structure that interacts with an activatable protein or other specific components of the signal transduction pathway involving the activable protein. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for a target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bias is towards peptides or nucleic acids that interact with known classes of molecules. For example, when the candidate agent is a peptide, it is known that much of intracellular signaling is carried out via short regions of polypeptides interacting with other polypeptides through small peptide domains. For instance, a short region from the HIV-1 envelope cytoplasmic domain has been previously shown to block the action of cellular calmodulin. Regions of the Fas cytoplasmic domain, which shows homology to the mastoparan toxin from Wasps, can be limited to a short peptide region with death-inducing apoptotic or G protein inducing functions. Magainin, a natural peptide derived from *Xenopus*, can have potent anti-tumor and anti-microbial activity. Short peptide fragments of a protein kinase C isozyme (βPKC), have been shown to block nuclear translocation of βPKC in *Xenopus* oocytes following stimulation. And, short SH-3 target peptides have been used as psuedosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate modulators as well.

Thus, a number of molecules or protein domains are suitable as starting points for the generation of biased randomized candidate modulators. A large number of small molecule domains are known, that confer a common function, structure or affinity. In addition, as is appreciated in the art, areas of weak amino acid homology may have strong structural homology. A number of these molecules, domains, and/or corresponding consensus sequences, are known, including, but are not limited to, SH-2 domains, SH-3 domains, Pleckstrin, death domains, protease cleavage/recognition sites, enzyme inhibitors, enzyme substrates, and Traf.

In a preferred embodiment, the candidate modulating agent is a polypeptide. In another preferred embodiment, the polypeptide is a cyclic peptide having at least 4 to 20 amino acids. Also in another preferred embodiment, the polypeptide is a catalytically inactive polypeptide. Examples of catalytically inactive polypeptides include, but are not limited to, catalytically inactive activable proteins and, more specifically a catalytically inactive kinases (e.g., PI3K) or caspases. In a further aspect, the candidate modulating agent is peptide fragment of an activatable protein, wherein the peptide fragment comprises an amino acid sequence that is a subsequence of the full-length amino acid sequence of the activatable protein.

In a preferred embodiment, the candidate agents are nucleic acids as described above in connection with binding elements.

In a preferred embodiment, the candidate agents are organic moieties as described above in connection with binding elements. Chemical (including enzymatic) reactions may be done on the moieties to form new substrates or candidate agents which can then be tested using the present invention.

As will be appreciated by those in the art, it is possible to screen more than one type of candidate agent at a time, e.g., by combining the candidate agents in the methods of the present invention. Thus, the library of candidate agents used may include only one type of agent (i.e. peptides), or multiple types (peptides and organic agents).

By "combining" is meant the combining of the various components in a reaction mixture in vitro or in a cell in vivo under conditions which promote an activity that is detectable using known methods or using the methods of the present invention (e.g., the binding of an antibody to a corresponding antigen or isoform of an activatable protein, or activation state of an activatable protein).

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, blocking steps, etc.

In a preferred embodiment, the reaction mixture or cells are contained in a well of a 96 well plate or other commercially available multiwell plate. In an alternate preferred embodiment, the reaction mixture or cells are in a FACS machine. Other multiwell plates useful in the present invention include, but are not limited to 384 well plates and 1536 well plates. Still other vessels for containing the reaction mixture or cells and useful in the present invention will be apparent to the skilled artisan.

The addition of the components of the assay for detecting the activation state or activity of an activatable protein, or modulation of such activation state or activity, may be sequential or in a predetermined order or grouping under conditions appropriate for the activity that is assayed for. Such conditions are described here and known in the art. Moreover, further guidance is provided below (see, e.g., in the Examples).

In a preferred embodiment, the methods of the invention include the use of liquid handling components. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In a preferred embodiment, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In a preferred embodiment, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradeable modular platform for additional capacity. This modular platform includes a variable speed orbital shaker, and multi-position work decks for source samples, sample and reagent dilution, assay plates, sample and reagent reservoirs, pipette tips, and an active wash station.

In a preferred embodiment, thermocycler and thermoregulating systems are used for stabilizing the temperature of heat exchangers such as controlled blocks or platforms to provide accurate temperature control of incubating samples from 0° C. to 100° C.

In a preferred embodiment, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In a preferred embodiment, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In a preferred embodiment, the detecting is by FACS. In another aspect, the detecting is by high pressure liquid chromatography (HPLC), for example, reverse phase HPLC, and in a further aspect, the detecting is by mass spectrometry.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

In a preferred embodiment, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety, including the parent application U.S. Ser. No. 10/193,462, filed July 2002, which claims the benefit of the filing dates of U.S. Ser. No. 60/304,434 and U.S. Ser. No. 60/310,141.

EXAMPLES

Example 1

In this Example, using the methods and compositions of the present invention, the present inventors (also referred to herein as "we") show that Leukocyte Function Antigen-1 (LFA-1) is essential in the formation of immune cell synapses and has a role in the pathophysiology of various autoimmune diseases. In this Example, using the methods and compositions of the present invention, the present inventors demonstrate that ICAM-2 induced an LFA-1 signal transduction pathway that is linked to receptor clustering and activation by both the microtubule and actin cytoskeleton. ICAM-2 exhibited a 21.7 pM/cell binding affinity as determined by single cell analysis. ICAM-2/LFA-1 engagement induced activation of PKC and a reorganization of both the actin and microtubule cytoskeleton. These events resulted in a Syk dependent activation of the p44/42 MAPK pathway upon cytotoxic T cell effector-target cell binding via active LFA-1. ICAM-2 mediated human $CD56^+CD8^+$ perforin release and resultant cytotoxicity to target leukemia cells. In comparison to the other ICAMs, ICAM-3 was found to be most similar to ICAM-2's effect and dissimilar to ICAM-1. In IL-2 pre-activated human PBMC, ICAM-2>ICAM-3>>ICAM-1 in mediating perforin release of a CD56+CD8$^{med}$ population. All ICAMs contributed to perforin and granzyme-A loss in CD56+CD8$^{high}$ populations. These results identify a specific functional consequence for ICAM-2/LFA-1 in subset-specific cytotoxic T cell immunity.

Introduction

Leukocyte Function Antigen-1 (LFA-1) is an α,β heterodimer integrin involved in leukocyte adhesion (van Kooyk, Y., and Figdor, C. G. (2000) Curr Opin Cell Biol 12, 542-547). At present, it is well understood that LFA-1 participates in lymphocyte adhesion, with prominent roles in the formation of the immunological synapse (Dustin, M. L., and Shaw, A. S. (1999) Science 283, 649-650), and lymphocyte extravasation and recirculation (Volkov, Y., at al., (2001). Nat Immunol 2, 508-514). LFA-1 adhesion is governed by the intercellular adhesion molecule (ICAMs)-1, -2, and -3 ligands (van Kooyk and Figdor, 2000). Patients afflicted with Leukocyte Adhesion Deficiency disorder (LAD), a syndrome in which the LFA-1 integrin is mutated or missing, suffer sever recurrent bacterial infections and impaired overall immunity (Bunting, M., et al., (2002) Curr Opin Hematol 9, 30-35). Among these clinical manifestations, the LFA-1 knockout mouse has suggested that LEA-1 may have a potential role in mediating tumor regression in adoptive immunotherapy (Mukai, S., et al., (1999) Cell Immunol 192, 122-132; Nishimura, T., et al., (1999) J Exp Med 190, 617-627). Although these studies genetically link a lymphocyte adhesion molecule with impaired immune function, the molecular details that mediate these immunopathologies are less well understood.

Investigations of LFA-1 have primarily focused on the integrin's adhesive role. It is unclear as to how the physical processes of LEA-1 integrin activation and receptor clustering are interconnected and translated into cellular signals upon ligand binding. It is less understood how the absence of these events leads to the devastating effects of LAD and the impaired immune responses in LFA-1 knockout mice. We therefore sought to decipher the molecular details of a model interaction of ICAM-LFA-1 to understand LEA-1 signaling mechanisms initiated upon cell-to-cell contact. Utilizing multiparameter single cell analysis to monitor LFA-1 receptor dynamics upon treatment with a soluble ICAM-2, we found that both the actin and the microtubule cytoskeleton couple ICAM-2 adhesion to LFA-1 activation and clustering. The microtubule cytoskeleton constrained the LFA-1 conformational change (activation), an event that preceded LFA-1 clustering as measured by multiparameter flow cytometry. The induced LFA-1 activation led to the activation of the p44/42 Mitogen Activated Protein Kinase pathway (MAPK; RAF/MEK/ERK), an event that was dependent on both Pyk2 and Syk kinase activities.

The present inventors investigated these molecular details of the ICAM-2 mediated LFA-1 activation in the adhesion between cytotoxic T cells and a target leukemia cell, an event that requires cell-to-cell contact. ICAM-2 stimulation of human CD56+CD8+ T cells could induce perforin/granzyme-A mediated cytotoxicity of leukemia cells. This directed killing was shared by ICAM-3 and to a lesser extent by ICAM-1, two other LFA-1 ligands. These results distinguish a signaling mechanism for ICAM-2/LFA-1 directed cytotoxic T lymphocyte immunity and suggest possible mechanisms by which tumor secretion of ICAM-2 and possibly ICAM-3 might allow for evasion of a directed cytotoxic T cell immune response.

Results

Recombinant ICAM-2 Promotes LFA-1 Mediated Adhesion

The present inventors chose a model Jurkat T cell line as a system to initially dissect the LFA-1 signaling mechanism and then verified the findings in human T cells. A biochemically purified ICAM-2 protein was produced to study ICAM-2/LFA-1 interactions in the absence of other ligands (FIG. 3A-H). We purified human ICAM-2 from retrovirally transduced N I H3T3 cells using immunoaffinity chromatography and subsequent gel filtration. We compared it to an ICAM-2-FC fusion protein produced in NSO murine myeloma cells. These murine based mammalian expression systems were chosen on the basis that they yielded a bioactive form of ICAM-2. Biochemical analysis of ICAM-2FC protein was consistent with the expected molecular weight of the fusion protein (76 kD, FIG. 3A) and purified human ICAM-2 displayed a molecular weight of 72-74 kD (FIG. 3A). This size was similar to the 75 kD ICAM-2 purified from Jurkat T cells (data not shown).

The present inventors generated a FITC conjugated ICAM-2 (ICAM-2-FITC) to study LFA-1 receptor dynamics by flow cytometry and laser scanning confocal microscopy (LSCM). We tested for ligand binding of the LFA-1 receptor by monitoring the binding kinetics of ICAM2-FITC on single cells. Low binding was observed in the first 150 seconds, whereupon there was a progressive increase until 750 seconds, and leveled thereafter (FIG. 3B, middle panel). In contrast, an a-LFA-1 antibody displayed an initial spike in the first 50-100 seconds and equilibrated until 800 seconds (FIG. 3B, bottom panel). Pre-activating LFA-1 by treatment with PMA (McDowall, A., et al., (1998) J Biol Chem 273, 27396-27403) showed an immediate binding of ICAM-2 (FIG. 3C, top panel). The gradual ICAM-2 binding after 150 seconds suggested an enhanced LFA-1 binding for its ICAM-2 ligand after some binding-induced event a property not observed using the a-LFA-1 or upon PMA activated LFA-1 (FIG. 3B). Binding of ICAM-2-FITC was not observed in trypsinized cells (data not shown) and was blocked by antibodies to LFA-1 (described below). Therefore, there appeared to be an increase in binding of the ICAM-2 ligand as a function of time, suggesting the presence of an induced binding site on the target cells.

Analysis of the ICAM-2 binding population by flow cytometry showed a dependency on both the actin cytoskeleton and temperature. ICAM-2 adhesion was enhanced at 37° C. vs. 4° C. (FIG. 3C). Pre-treatment with the actin depolymerizing agent cytochalisin D revealed two ICAM-2 binding populations at both 37° C. and 4° C., contrasting with the binding phenomena observed for a-LFA-1 (FIG. 3C). Saturation of ICAM-2-FITC was observed at 37° C. more readily than at 4° C. (data not shown, FIG. 3H). Single cell binding affinity measurements for ICAM-2 were obtained by computing the percent ICAM-2-FITC bound per cell (FIG. 3D). Curve fit analysis indicated a dissociation constant of 0.21 +0.07 mM/10$^4$ cells (FIG. 3D). This value equates to 21.7 pM/cell, representing the first ligand binding measurements reported for ICAM-2 within the physiological context of cell surface LFA-1. Thus, quantitative single cell analysis of ICAM-2 ligand binding suggests strong binding at physiological temperatures.

Soluble ICAM-2 Induces LFA-1 Clustering and Cytoskeleton Polarization

The present inventors investigated if LFA engagement altered cytoskeletal structures and observed a reorganization of both the actin and microtubule cytoskeleton upon ICAM-2 stimulus (FIG. 4A). The present inventors monitored the cytoskeletal architecture by flow cytometry and observed a simultaneous change in the actin and microtubule organization upon ICAM-2 binding (FIg. 4B), an effect consistent with depolymerization. ICAM-2 treatment induced a rapid clustering of LFA-1 within one minute, with multiple clustering events at five minutes (FIG. 4C, left panel). Using the ICAM-2-FITC ligand to visualize the cell surface, indicated that the ICAM-2 ligand induced clustering of the LFA-1 receptor (FIG. 4C, left panel). The clustering event showed some colocalization using a non-blocking b2 integrin antibody (clone CTB104) (FIG. 4C, right panel). Thus, we speculated that ICAM-2 binding to LFA-1 induced a signal that resulted in a reorganization of the LFA-1/ICAM-2 complex. We therefore decided to investigate this in relation to the observed changes in the actin/microtubule cytoskeleton.

The present inventors assessed LFA-1 receptor dynamics by multiparameter flow cytometry upon ICAM-2 binding to correlate LFA-1 activation and clustering. We utilized the doublet discriminator module on a FACSCalibur machine to distinguish between distributed and focalized fluorescence pulses (FFP) upon laser excitation of single cells. Incubation of ICAM-2 at 37° C. vs. 4° C. displayed a decrease in the FFP, an effect that was greatly enhanced upon cytochalisin D treatment (FIG. 4D). ICAM-2-FITC surface binding was monitored by the fluorescence intensity and normalized against the time-of-flight (TOF) of the fluorescence pulse (FP). We interpreted the value of ICAM-2-FITC intensity per TOF as a quantitative assessment for LFA-1 clustering, as the TOF is proportional to the laser-excited cellular area. Computing this value as a function of time for an ICAM-2 stimulus (FIG. 4E) is proportional to the increased clustering events observed by LSCM (see FIG. 4C).

ICAM-2 Adhesion Induces a Conformational Change in LFA-1 that is Regulated by the Microtubule Cytoskeleton.

Although the enhanced ICAM-2 adhesion and induced LFA-1 clustering is reflective of overall increased avidity for the ICAM-2 ligand, it does not necessarily reflect an LFA-1 activation state (high affinity state) (McDowall et al., 1998). Upon LFA-1 activation, a conformational change exposes an epitope that is recognized by the mAb24 antibody (Neeson, P. J., et al., (2000) J Leukoc Biol 67, 847-855). A mAb24-ALEXA FLUOR®633 conjugate was used to assess the activation state of LFA-1 upon ICAM-2 stimulus by flow cytometry. Unstimulated cells did not display mAb24 binding, contrasting the induction observed with PMA treatment (FIG. 4F). ICAM-2 stimulated cells displayed a bimodal population in active LFA-1, an effect that was attenuated by cytochalisin D (FIG. 4F). Treatment with microtubule disrupting agents, nocodazole and taxol, resulted in full activation of LFA-1 upon ICAM-2 stimulus (FIG. 4F). In contrast, disrupting the actin cytoskeleton via cytochalisin D diminished the ICAM-2 induced LFA-1 activation, although it enhanced LFA-1 receptor clustering and subsequent ICAM-2 binding (see FIG. 4D). Therefore, the actin and microtubule cytoskeletal network differentially impact LFA-1 activity and avidity.

The present inventors monitored LFA-1 activation and clustering simultaneously as a function of ICAM-2 stimulus per time by flow cytometry. Correlating the mean fluorescence of mAb24 antibody with the LFA-1 clustering value revealed LFA-1 activation preceded LFA-1 clustering (FIG. 4G) within 30 seconds there was a significant increase in binding of the mAb24 antibody but only a modest increase in clustering. However, after another 30 seconds up to 30 minutes the relative binding of mAb24 increased somewhat but there was a significant increase in the clustering value (FIG. 4G). Thus, these results suggest that the ICAM-2 ligand induced activation of LFA-1 is followed by subsequent LFA-1 clustering.

The present inventors observed that treating cells with a PKC inhibitor, bisindolymaleimide I (BIM I), inhibited ICAM-2 induced LFA-1 activation as measured by using mAb24 binding (FIG. 5A). ICAM-2 adhesion, as measured by the binding of ICAM-2-FITC, was not affected (FIG. 5A). This suggested that the ligand induced receptor conformational change was dependent on intracellular kinases. Interestingly, ICAM-2 induced a calcium influx, a component necessary in PKC activation (data not shown). Thus, these observations suggest that the ICAM-2 ligand induced exposure of the mAb24 neoepitope triggers a PKC dependent intracellular signaling event. We decided to investigate the downstream signaling consequences of ICAM-2 binding to LFA-1.

ICAM-2 Induces p44/42 MAPK Activity through LFA-1

Flow cytometric based kinase profiling experiments were performed to identify a signaling pathway downstream of PKC activation upon ICAM-2 stimulus. Treatment with ICAM-2 induced both p44/42 MAPK phosphorylation and activation (FIG. 5B-D). An ICAM-2 titration correlated with phosphorylation of p44/42 MAPK as determined by single cell flow cytometric analysis (FIG. 5B, top panel), results congruent with kinase activity analysis (see FIG. 5C). Titration of mAbs to a.sub.L and b2 integrins competed with ICAM-2 binding, and thus diminished the induced p44/42 MAPK phosphorylation (FIG. 5B, bottom panel). This inhibition was not observed after pretreatment with mAbs to b1, b3, $a_m$, or $a_x$ integrins (FIG. 5C) indicating that the ICAM-2/LFA-1 interaction was mediating the p44/42 MAPK activation.

Activation of PKC, PYK2, and SYK are Necessary for the ICAM-2/LFA-1 Induction of p44/42 MAPK Activity The present inventors undertook flow cytometric based p44/42 MAPK kinase inhibition and activation profiling to identify necessary components for LFA-1 signaling. PKC inhibitor BIM I, cytoskeletal disrupting agents cytochalisin D, taxol, nocodozole, and sequestering of divalent cations by EDTA diminished the ICAM-2 induced p44/42 MAPK signal (FIG. 5D), suggesting that the ligand-induced events of LFA-1 are mechanically linked to signal transduction by the actin-microtubule cytoskeleton. To identify upstream kinases that were responsible for signal transmission from LFA-1 to p44/42 MAPK, a series of kinase inhibitors were applied and tested for their ability to abrogate the ICAM-2 induced p44/42 MAPK activity (FIG. 4H-I). Whereas Herbimycin A and Emodin, inhibitors of src and P56lck had no effect, tyrphostin A9 and piceatannol, specific inhibitors of proline-tyrosine kinase 2 (Pyk2) and Spleen-tyrosine kinase (Syk), respectively (Avdi, et al. (2001) J Biol Chem 276, 2189-2199.; Fuortes, et al., (1999) J Clin Invest 104, 327-335) abrogated the ICAM-2 induced activation of p44/42 MAPK and its upstream activator Raf-1 (FIG. 6A).

The present inventors tested whether Pyk2 and Syk interacted with the b2 integrin. Pyk2 and Syk were phosphorylated and co-immunoprecipitated with b2 integrin upon ICAM-2 treatment (FIG. 6B), indicating Pyk2 and Syk translocated to the membrane (FIG. 5E). This was coincident with phosphorylation of Pyk2 and Syk upon ICAM-2 stimulus as a function of time (FIG. 6B-C). Phosphorylation of PKCa/$b_{II}$, and Pyk2 were detected at one minute, followed by Syk phosphorylation at 5 minutes (FIG. 6C). We confirmed that Pyk2 and Syk activities were dependent on PKC activation (data not shown FIG. 6D-E). Taken together with the above results, this suggested that the LFA-1 signaling mechanism imparted by ICAM-2 is at least initiated by PKC and relayed to the p44/42 MAPK pathway by Pyk2 and Syk.

LFA-1 is Involved in Effector-Target Cell Adhesion and Facilitates Human Cytotoxic T Cell Activation Since LFA-1 is involved in adhesion between lymphocytes, a process that occurs at several immunological synapses, we were interested in investigating the molecular events identified for the ICAM-2/LFA-1 interaction in a physiological context. It has been suggested that a clustered topographic presentation of ICAM-2, independent of expression levels, is an effective target structure by which natural killer cells initiated cytotoxicity (Helander, T. S., et al., (1996) Nature 382, 265-268). We first applied a FACS based effector-target killing assay to quantitatively monitor target cell lysis of HL60 leukemic cells upon treatment with stimulated human PBMC at various effector: target cell ratios. Flow cytometric detection of target cell lysis has been reported to be more sensitive than the standard chromium release assays (Lecoeur, H., et al., (2001) J Immunol Methods 253, 177-187). We labeled HL60 cells with the fluorescent dye CFSE and monitored the cell quantity by flow cytometry in standard effector-target cell based assays. Soluble ICAM-2 could initiate target cell lysis in the presence of IL-2 but not in the absence of IL-2 (FIG. 7A). In IL-2 pre-activated cells, ICAM-1 and ICAM-3 did not initiate as potent a cytotoxic cell response in contrast to ICAM-2 (FIG. 7B).

Since natural killer cells (NK) comprise a heterogeneous population, namely specific cytotoxic T lymphocytes (CTL, with C8$^+$ subsets therein), NK cells (CD16$^+$and subsets therein), and CD4$^+$ TH1 cells (Biron, C. A., and Brossay, L. (2001) Curr Opin Immunol 13, 458-464.), we determined if ICAM-2 was unique to a particular human NK cell subset. We utilized the multidimensional gating capability of flow cytometry to identify distinct cellular populations that were contributing to the cytolytic activity observed in human PBMC. We also monitored intracellular levels of perforin and granzyme-A by flow cytometry, two proteins that mediate target cell lysis by NK cells in these populations. We identified 6 distinct populations by CD8 and CD56 surface stains in human PBMC (FIG. 8A panel I) and gated on these subsets for all subsequent intracellular functional assays (FIG. 8A panels II-V). We performed effector-target cytotoxicity assays in the presence of ICAM-1, ICAM-2, and ICAM-3 soluble ligand and HL60 target cells. We did not observe significant changes in population subset frequencies post stimulation (FIG. 8A, panel I). The CD56$^+$CD8$^{low}$ population displayed no significant changes in intracellular perforin or granzyme-A upon stimulation with ICAM-1, -2, or -3 (FIG. 8A, panel II). The CD56$^+$CD8$^{med}$ population displayed a slight increase (1.5-2 fold) in the frequency of the perforin negative population for ICAM-2 and ICAM-3 (21.5% ICAM-2>19.8% ICAM-3>13.7% ICAM-1) (FIG. 8A, panel III). The CD56$^+$CD8$^{high}$ population displayed a loss in both granzyme-A and perforin for ICAM-1, -2, -3 stimulations compared to unstimulated with a significant loss in the granzyme-A negative population for ICAM-2 (58.3%) compared to ICAM-1 (4.12%) or ICAM-3 (3.07%) (FIG. 8A, panel IV). The CD56$^{-CD}$8$^{high}$ also displayed a loss of both granzyme-A and perforin by all ICAM stimulations (FIG. 8A panel V). Since it was not possible to positively identify the subsets within the CD56$^-$CD8$^-$population, they were omitted from analysis.

Quantifying the intracellular amounts of perforin and granzyme-A in the CD56CD8 subsets relative to unstimulated cells also identified similarities and differences for the ICAMs as evidenced below. ICAM-2 and ICAM-3 mediated loss of granzyme-A and perforin to a greater extent than ICAM-1 (FIG. 8B-C). Additionally, in IL-2 pre-activated cells, differences where seen with the ICAM stimulations: ICAM-2>ICAM-3>>ICAM-1 displayed a loss of perforin, particularly in the CD56$^+$CD8$^{med/high}$ populations (FIG. 8B). ICAM-2 and ICAM-3 also induced perforin loss in the CD56$^+$CD8$^{low}$, however ICAM-2 required preactivation by IL-2 (FIG. 8B). There were lower levels of granzyme-A detected for the CD8$^{high}$ subsets (CD56$^+$ or CD56$^-$) for ICAM-2>ICAM-3>ICAM-1>unstimulated (FIG. 8C). In the presence of IL-2 pre-activation, all the ICAMs induced release of granzyme-A in the CD56$^+$CD8$^{high/med}$ populations, with a particular decrease by ICAM-2 (FIG. 8C). No significant changes were seen in the CD56$^+$CD8$^{low}$ population for granzyme-A (FIG. 8C). These differences were similar at various effector-target cell ratios (50:1, 25:1, 12.5:1) (data not shown). Thus, similarities and difference exist for ICAM-1, -2, and -3 stimulation of cytolytic activity in CD56CD8 subsets. All three ICAMs mediated perforin release in the CD56$^-$CD8$^{high}$ populations. ICAM-2 and ICAM-3 were most similar in mediating perforin/granzyme-A release in the CD56$^+$CD8$^{high}$ and CD56$^+$CD8$^{med}$ populations.

We focused on the CD56$^+$CD8$^+$ cells (both the CD8.sup.med and CD8.sup.high subsets) and tested if inhibition of Syk, p44/42 MAPK or disruption of the cytoskeleton detrimentally affected effector-target (E:T) cell conjugation as measured by a flow cytometric conjugate formation assay (Morgan, M. M., et al., (2001) J Immunol 167, 5708-5718). Disruption of cytoskeletal actin and microtubules enhanced E:T conjugate formation (FIG. 9A) congruent with prior results that disruption by these agents enhanced LFA-1 activation. Inhibition of Syk by piceatannol inhibited conjugate formation whereas inhibiting p44/42 MAPK by PD98059 did not (FIG. 9A). These results suggest that Syk activity is necessary for LFA-1 adhesion of effector-target cells and is consistent with a report indicating that Syk/ZAP-70 are necessary for LFA-1 to LFA-1 activation on the same cell (Soede, R. D., et al., (1999) J Immunol 163, 4253-4261). P44/42 MAPK appeared to not be necessary for E:T conjugate formation. Monitoring active LFA-1 and intracellular activation of p44/42 depicted a time dependent correlation between these two markers in CD56$^+$CD8$^+$ cells as stimulated by ICAM-2 (FIG. 9B).

Discussion

In this report it was observed that (1) ICAM-2 can induce LFA-1 clustering, activation, and cytoskeletal reorganization in the absence of exogenous activators such as cytokines or TCR signaling; (2) LFA-1 transmits a signal to the p44/42 MAPK pathway involving PKC, Pyk2, and Syk upon ligand binding; and (3) LFA-1 receptor dynamics are mechanically coupled to signal transduction by both the actin and microtubule cytoskeleton network. The physiological outcome of these molecular events triggered perforin and granzyme A mediated CD56$^+$CD8$^+$ T cell cytotoxicity that were mostly shared by ICAM-2 and ICAM-3 but not ICAM-1.

b2 integrin signaling mechanisms vary depending on the system of study and are centered on adhesive roles in Cell morphology and motility (Dib, K. (2000) Front Biosci 5, D438-451). b2 integrin signaling has been shown to involve cytoskeletal reorganization via tyrosine phosphorylation of paxillin, vav, and GTPase activating proteins among others (Fuortes, M., et al., (1994) J Cell Biol 127, 1477-1483; Zheng, L., et al., (1996) Proc Natl Acad Sci USA 93, 8431-8436). Studies focused on LFA-1 mediated leukocyte adhesion (CD11a/CD18) have shown a regulatory role for PKC in LFA-1 avidity (Bleijs, D. A., et al., (2001) J Biol Chem 276, 10338-10346; Hedman, H., and Lundgren, E. (1992) J Immunol 149, 2295-2299) and have demonstrated that TCR signaling can activate LFA-1 (Peterson, E. J., et al., (2001) Science 293, 2263-2265). It has also been shown that chemokines, in the absence of TCR signaling, can serve as activators of LFA-1 during lymphocyte/endothelial contact (Constantin, G., et al., (2000) Immunity 13, 759-769). It has not been clear how LFA-1 integrin adhesion, clustering, and activation are coupled to intracellular signaling events, in the absence of external (chemokine) or internal (TCR or costimulatory molecule) stimulation.

A synthesized peptide of ICAM-2's first Ig domain (P1, amino acids 21-42) can induce LFA-1 mediated adhesion at high concentrations (62 mM), which was comparable to a 48-fold lower ICAM-2 soluble protein concentration (1.3 mM) in a bulk cellular adhesion assay (Kotovuori, A., et al., (1999) J Immunol 962, 6613-6620). However, P1 binding did not induce the active conformation of LFA-1 and did not induce calcium influx (Kotovuori et al., 1999), whereas full length ICAM-2 binding resulted in active LFA-1 (see FIG. 4F) and a calcium influx event (data not shown). The calculated ICAM-2 affinity of 217±66 nM (per $10^4$ cells) contrasts the 605±55 nM k.sub.D reported using BIAcore analysis of an engineered "active" locked I domain of LFA-1 (Shimaoka, M., et al., (2001) Proc Natl Acad Sci USA 98, 6009-6014). The reported affinities for ICAM-2 binding here take advantage of single cell resolution within a physiological context, something not possible utilizing purified or genetically engineered LFA-1. The differences observed for peptide vs. protein concentrations are likely attributed to impurities in the peptide synthesis and/or presence of carbohydrate moieties native to the endogenous ICAM-2, which comprise greater than 30 kD of its approximate 66 kD molecular weight and have been suggested to orient ICAM-2 binding to LFA-1 (Casasnovas, J. M., et al. (1997) Nature 387, 312-315; de Fougerolles, A. R., et al. (1991) J Exp Med 174, 253-267).

We investigated the role of the actin and microtubule cytoskeleton in LFA-1 receptor activation and clustering as induced by the ICAM-2 ligand by multiparameter flow cytometry. Disruption of the actin cytoskeleton enhanced LFA-1 clustering and ICAM-2 binding, corroborating previous studies that suggested the actin cytoskeleton constrains LFA-1 mobility (Lub, M., et al., (1997) Mol Biol Cell 8, 341-351). Interestingly, actin depolymerization abrogated the ICAM-2 induced LFA-1 activation. In contrast, disruption of the microtubules by both nocodazole and taxol enhanced LFA-1 activation as determined by exposure of the neo-epitope recognized by the mAb24. Recently, it has been reported that depolymerization of microtubules increases the lateral mobility of b2 integrins in macrophage cell lines (Zhou, X., et al., (2001) J Biol Chem 276, 44762-44769); therefore its conceivable that the microtubules regulate the conformational change upon ligand binding necessary for exposure of the LFA-1 activation epitope. These observations suggest the actin-microtubule cytoskeleton regulates both the high-avidity and high affinity state of LFA-1 upon ligand binding. We observed that LFA-1 signal transduction was abrogated in the presence of all cytoskeletal disrupting agents tested (cytochalasin D, nocodazole, and taxol) indicating that the LFA-1 receptor is linked to signal transduction machinery by the cytoskeleton. Thus, the mechanistic uncoupling of the high avidity and high affinity states of LFA-1 suggests that intracellular events that regulate/mediate these two states exist at the LFA-1 integrin-cytoskeletal juncture and relay the LFA-1 receptor dynamics to intracellular signaling proteins upon ligand binding.

Several chemical inhibition screens were designed to identify the proteins involved in the LFA-1 to p44/42 MAPK signaling event. Both Pyk2 and Syk were identified to be necessary for activation of the p44/42 MAPK pathway and were dependent on PKC activity upon ICAM-2 binding. Phosphorylation of Pyk2 has been associated with homotypic adhesion mediated by an LFA-1/ICAM-1 interaction in B cells (McDonald, J. T., et al., (2000) Immunol Invest 29, 71-80). In addition, Pyk2 activation has been shown to be necessary for p44/42 MAPK activity in other model systems (Barsacchi, R., et al., J. (1999) FEBS Lett 461, 273-276; Lev, S., et al., (1995) Nature 376, 737-745). Syk is a tyrosine kinase essential in aIIb3 signaling (Saci, A., et al., (2000) Biochem J 351 Pt 3, 669-676), and links FceRI signaling to the ras/MAPK pathway (Jabril-Cuenod, et al., (1996) J Biol Chem 271, 16268-16272). Inhibition or ablation of Syk, either by pharmacological means (via inhibition by piceatannol), biochemical means (dominant negative Syk), or genetic means (Syk$^{-/-}$ mice) inhibits natural cytotoxicity (Brumbaugh, K. M., et al., (1997) Exp Med 186, 1965-1974; Colucci, F., et al., (1999) J Immunol 163, 1769-1774). Thus LFA-1 activation signaling to Syk, a kinase that has been shown to be important for NK cell function, provides a biochemical link between surface integrin activation and effector cell function.

The present inventors demonstrated that both Pyk2 and Syk are necessary in ICAM-2 induced LFA-1 signaling to Raf-1, the upstream kinase in the p44/42 MAPK (RAF/MEK/ERK) cascade. Inhibition of p44/42 MAPK did not prevent the occurrence of CD56$^+$CD8$^+$ cell conjugation. By immunofluorescence analysis, it has been shown that treatment of the NK leukemic cell line YT with the p44/42 MAPK inhibitor PD98059 inhibits perforin redistribution to the site of effector-target cell contact (Wei, S., et al., (1998) J Exp Med 187, 1753-1765). In addition, the p44/42 MAPK pathway has been shown to be important in the regulation of cytoxicity in natural killer cells (Jiang, K., et al., (2000) Nat Immunol 1, 419-425). Thus, the p44/42 MAPK pathway, here demonstrated to become active upon LFA-1/ICAM-2 binding, has been shown to be connected to at least perforin granule exocytosis. Thus, the LFA-1 signaling pathway as elicited by ICAM-2 contains signaling junctures that map to both the effector-target cell adhesion event and activation of cytolytic machinery in the human CD56$^+$CD8$^+$ cytotoxic T cell population. These results provide direct evidence for a functional consequence of LFA-1 integrin adhesion with cytolytic signaling mechanisms.

We also observed that ICAM-2 was similar to ICAM-3 in mediating cytolytic activity as evidenced by release of perforin and granzyme-A in effector-cell conjugation, effects of which contrasted ICAM-1 (see FIG. 8C). We have previously observed similarities between ICAM-2 and ICAM-3 intracellular signaling mechanism that also differed from that of ICAM-1 (Perez, O. D., et al., (2002) Immunity 16, 51-65). However, the results do not exclude the possibility of ICAM-2 stimulating other yet to be identified cytotoxic capable subsets, as high cytolytic activity was observed in bulk PBMC (see FIG. 7A-B).

Prior investigations into cytotoxic T cells have established that blocking the LFA-1/ICAM interactions inhibits effector-target cell adhesion and therefore concluded that it also blocks cytolytic activity in NK cells (Donskov, F., et al., (1996) Nat Immun 15, 134-146; Krensky, A. M., et al., (1984) J Immunol 132, 2180-2182; Matsumoto, G., et al., (2000) Eur J Immunol 30, 3723-3731). Functional studies of NK cells from LFA-1$^{-/-}$ mice have demonstrated that LFA-1 adhesion is necessary for IL-2 activated NK killing (Matsumoto et al., 2000) and also that LFA-1$^{-/-}$ CD8$^+$ T cells are defective for T cell activation and effector function (Shier, P., et al., (1999) J Immunol 163, 4826-4832). Interestingly, NK cell cytotoxicity is defective in NK cells from LAD patients (Shibuya, K., et al., (1999) Immunity 11, 615-623). It has only recently been shown that the directed killing of cytotoxic T lymphocytes involves polarization of the microtubule-organizing center (MTOC) towards LFA-1 at the CTL-target site (Kuhn, J. R., and Poenie, M. (2002) Immunity 16, 111-121), an indication that LFA-1 may possess a functional role other than strictly adhesion.

In conclusion we find that ICAM-2, as an LFA-1 ligand, can mediate activation and clustering of the LFA-1 receptor—an event that in turn polarizes the microtubule and actin cytoskeleton and activates the p44/42 MAPK pathway. These events were found to be necessary for effector-target cell binding of $CD56^+CD8^+$ T cells, and perforin/granzyme A mediated cytolytic activity. This effect was shared by ICAM-3. The mechanisms governing LFA-1 receptor dynamics and intracellular signaling reported here suggest LFA-1 signaling functionally contributes in $CD56^+CD8^+$ cytolytic activity in addition to possessing an adhesive role upon which other molecular interactions occur. Improper localization of the MTOC has been shown to inhibit exocytosis of lytic granules in $CD8^+$ tumor infiltrating T cells, thereby ablating perforin mediated cytolytic activity necessary for a CTL response in murine tumor models (Radoja, S., et al., (2001) J Immunol 167, 5042-5051). Ironically, defective $CD8^+$ tumor infiltrating T cells can effectively mediate cell killing in vitro (Radoja, S., et al., (2001) J Immunol 166, 6074-6083), suggesting tumor mediated inhibitory mechanisms exist within the tumor microenvironment. The production of soluble ICAMs (1 and 3) has been observed in sera from cancer and autoimmunity patients, though analysis has not been extended to ICAM-2 (Bloom, et al., (2002) J Rheumatol 29, 832-836). Only one report has indicated that elevated levels of soluble ICAM-2 were present in leukemia patients and decreased upon chemotherapy (Mustjoki, S., at al., (2001) Br J Haematol 113, 989-1000). The etiology of these observations is unknown. In the context of the work presented here, it is plausible to speculate that either dysregulation of surface ICAM-2 or secretion of soluble ICAM-2 can prematurely trigger or block $CD56^+CD8^+$ cytolytic activity at the effector-target site and permit tumor escape from T cell lysis. Other, specific roles, of ICAM-2 in its interaction with other integrin ligands could lead to a better understanding of events that promulgate from the effector:target cell interface Materials and Methods Immunological and Chemical Reagents mAbs to b1, b2, b3, b4, b5, b6, a1, a4, a5, $a_L$, LFA-1, Pyk2, SyK, Mac-1, ICAM-1, and ICAM-3 (PharMingen). CD3, CD4, CD8, CD19, CD56, CD45 direct conjugates (FITC/PE/PERCP/APC/Biotin), granzyme-A-FITC (PharMingen). Perforin-CY5 and CD8-CY5PE (gift from the Herzenberg Laboratory, Stanford University). ICAM-2 mAb and ICAM-2-FITC (IC2/2 Research Diagnostics). Anti-phospho PYK2 (Y402), anti-phospho-p44/42 (pT185Py187) (Biosource). Anti-phospho PKCa/b(Thr638), anti-phospho-Syk(Tyr525/526), anti-phosphoRaf1 (Ser259) (Cell Signaling Technologies). Protein and chemical reagents used: fluorescein isothiocyanate (FITC) (Pierce), Alexa fluor dye series 488, 546, 568, 633, taxol-alexa546, phalloidin-alexa633, and CFSE (Molecular Probes). Tyrphostin A9 and 18, SB203580, piceatannol, bisindolylmaleimide I and II, herbimycin A (Calbiochem). Emodin, genistein, DMSO, PMA, PHA, staurosporine, ionomycin, propidium iodide, cytochalasin D (Sigma). Protein NG agarose (SCBT). Recombinant human IL-2 (Roche), recombinant human ICAM-1-FC, ICAM2-FC, ICAM3-FC (Genzyme). Secondary antibodies to mouse and rabbit IgG (Santa Cruz). Mock treatments consisted of mouse IgG (for antibodies), 1% BSA (for proteins), or 0.001% DMSO vehicle (for chemicals).

Cell Culture

NIH3T3 cells were maintained in DMEM, 10% DCS, 1% PSQ (Duelbecco Modified Eagle Media, 10% Donor calf serum, 1% penicillin-streptomycin (1000 units/ml and 2 mM L-glutamine PSQ). Jurkat T-cells were maintained in RPMI-1640, 10% FCS, 1% PSQ at $1\times10^5$ cells/ml and serum starved 12 hours for all functional assays. Cells were maintained at 5% $CO_2/37°$ C. humidified incubator. Human peripheral blood monocytes were obtained by Ficoll-plaque density centrifugation (Amersham Pharmacia, Uppsala, Sweden) of whole blood from healthy donors (Stanford Blood Bank) and depleted for adherent cells. Magnetically activated cell sorting was used to negatively isolate naïve $CD8^+$ T cells for studies as indicated (Dynal, Oslo, Norway).

Soluble ICAM-2 Generation and Synthesis of ICAM-2-FITC and ICAM2-Beads

Full length ICAM2 cDNA was obtained from Jurkat cells and cloned into retroviral vector PBM-Z-IN at the BamHI/SalI site as described (Perez of al., 2002). Human ICAM-2 was overexpressed in NIH3T3 cells by retroviral infection and harvested by immunoaffinity chromatography. ICAM-2 was affinity purified using a two step lysing procedure and subsequent purification on an anti-ICAM-2 solid support. Cells were lysed in buffer A (20 mM Tris pH 7.5, 150 mM NaCl 1 mM EDTA 1 mM EGTA, 0.1% NP40, 2.5 mM $Na_2PO_4$, 1 mM b-glycerophosphate, 1 mM $Na_3VO_4$, 1 mg/ml Leupeptin, 1 mM PMSF, protease inhibitor cocktail tablet (Boehringer Mannheim) for 5 min 4° C., and subsequently permeabilized with 50% v/v with buffer B (Buffer A plus 1% Triton-X-100) for 30 min 4° C. Supernatant was harvested by centrifugation (14,000 RPM, 5 min, 4° C.). An Anti-ICAM-2 pAb to the C-terminal (4 mgs, Santa Cruz) was conjugated to an Affi-Gel Hz activated support (Biorad) as suggested by manufacturer. This support couples Ig molecules via the FC region, resulting in higher antigen binding capacity. Batch lysate of harvested supernatant was performed (4° C., for 2 hrs), and washed 4 times in buffer C (0.1% Tween-20, PBS pH 7.4). ICAM-2 protein was eluted by 4.5 M NaCl (in Tris pH 6.8), dialyzed overnight (in PBS pH 7.4, 0.001% azide, 0.01% glycerol, 4° C.), concentrated using size exclusion spin chromatography and stabilized using 0.01% glycerol. Anti-ICAM-2 solid support was re-equilibrated in buffer C, stored in 0.001% thimerosal and re-used up to 3 times. Purity was >98% as assessed by coomasie gel. Size exclusion chromatography removed higher molecular weight aggregates and were not observed on purified ICAM-2 by native gel electrophoresis. 20 mgs were purified by this method and used for this study. ICAM-2-FITC synthesis was achieved by chemical conjugation to NHS-Fluorescein (Pierce) and unreactive dye was removed by gel filtration. ICAM-2-FITC probe did not integrate into trypsinized Jurkat cells or bind when blocked by LFA-1 antibody clones TS1/22 or TS1/18 (Developmental Hybridoma Studies Bank) or unlabeled ICAM-2 protein as determined by flow cytometry. ICAM-2-FITC binding was not blocked by b2 integrin clone CT104 (Santa Cruz). Purified ICAM-2 was comparable to human recombinant ICAM-2FC fusion protein purified from NSO murine myeloma cells (Genzyme). ICAM-1 FC and ICAM-3FC were also purified from NSO cells (Genzyme). Proteins were spun at 14,000 RPM, 5 min prior to use. 1 mg of ICAM-2 protein was conjugated to $2\times10^8$ epoxy activated beads as suggested by manufacturer (Dynal). $4\times10^5$ beads containing a total of 2 mg ICAM-2 protein were used as indicated. Gel imaging was performed on a VersaDoc machine (Biorad) and analyzed using Quantity One quantitation software (Biorad).

Flow Cytometry

Intracellular and extracellular staining was performed as described (Perez and Nolan, 2002). Intracellular probes for active kinases were made by conjugating phospho-specific antibodies to the Alexa Fluor dye series as described and used in phospho-protein optimized conditions (Perez and Nolan, 2002). Kinetic analyses was performed by direct application of fixation buffer in time synchronized 96-wells maintained at 37° C. Intracellular actin and microtubule staining was performed using phalloidin-Alexa633 and taxol-Alexa546 dyes (Molecular Probes). Adhesion and clustering assays were performed using ICAM-2-FITC as described in text. LFA-1 activation was assessed by either mAb24-Alexa633 or mAb24-Alexa546 conjugate, surface stained at 37° C. Flow cytometry data are representative of 3 independent experiments of $10^5$ cells/sample. 10-50,000 events were collected and manually calibrated on a FACSCalibur machine. Data plotted in bar graph format is expressed as geometric mean fluorescence intensity (MFI) and normalized for isotype controls. Log ratios are defined as the MFI of stimulus to the MFI of unstimulated cells. Data was analyzed using Flowjo software (Treestar).

Single Cell ICAM-2 Binding Measurements

Percentage of ICAM-2-FITC binding was expressed as $100*((MFI_{exp}-MFI_{ctl})/(MFI_{final}-MFI_{ctl}))$, where $MFI_{exp}$ equals the mean fluorescence intensity of experimental concentration, MFI, equals mean fluorescent intensity of unstained cells, $MFI_{final}$ equals mean fluorescent intensity of final concentration that saturated binding. The samples were incubated with final concentrations as indicted in Figure for 30 min at 37° C. in 50 mL staining media (def RPMI, 4% FCS), washed 1× (500 mL, PBS pH 7.4, containing 1 mM EDTA), and resuspended in 100 mL (1% paraformaldehyde). Dilution factor of staining conditions and molecular weight of 72.1 kD was used in determining molar concentrations. The staining buffer contained 2.4 mM calcium and 2 mM magnesium. The data were fit to the equation $V=V_{max}[S]/(K_m+[S])$ where V is the percent bound, [S] is the ICAM-2-FITC concentration, and $K_m$ is the Michaelis-Menten binding constant using Kaleidagraph software.

Laser Scanning Confocal Microscopy

Jurkat cells were treated as indicated and adhered to poly-L-lysine (Sigma) coated sterilized coverslips (1 mg/ml, 30 min) by mild centrifugation (1000 RPM, 10 min), washed twice in phosphate buffered saline pH 7.4 (PBS) and fixed in 2.7% paraformaldehyde (in PBS). Cells were permeabilized (5 min, 0.1% Triton-X-100 in PBS), washed twice in PBS, blocked in 4% FCS, and subjected to antibody or intracellular staining as indicated. Stained coverslips were mounted and visualized using a Zeiss laser scanning confocal microscope 510.

Immunoprecipitations, Immunoblotting and Kinase Assays

Cell extracts were prepared by washing $2 \times 10^6$ cells (treated as indicated) in ice cold PBS and harvesting in lysis buffer (20 mM Tris pH 7.5, 150 mM NaCl 1 mM EDTA 1 mM EGTA, 1% Triton X-100, 2.5 mM $Na_2PO_4$, 1 mM b-glycerophosphate, 1 mM $Na_3VO_4$, 1 mg/ml Leupeptin, 1 mM PMSF, protease inhibitor cocktail tablet (Boehringer Mannheim). Extracts were centrifuged 14,000 RPM (5 min, 4° C.) and 10-20 mg (BCA protein assay (Pierce)) were immunoblotted using standard procedures. Immunoprecipitations (IP) were pre-cleared with protein A/G plus-agarose beads, incubated with primary ab (1 h), protein A/G plus-agarose beads (1 h) and washed 4× with lysis buffer. Blots were incubated with the indicated antibodies and developed using ECL (Amersham). Immunoblots stripped and reprobed (as indicated) were done by incubating with stripping buffer (62.5 mM Tris, pH 6.8, 10% SDS, 1% b-mercaptoethanol) (30 min, 55° C.). MAPK activity was detected by a p44/42 MAPK kinase kit as suggested by manufacturer (Cell Signaling Technologies).

Cytolytic Activity, Perforin Release Assays, and Conjugate Formation Assays

Target cell lysis was measured by flow cytometric based detection of CFSE labeled HL60 cells. HL60 cells were labeled with 1 mg of CFSE (30 min, 37° C.). Targets were washed twice and mock treated, IL-2 activated (100 U/ml), CD3/CD28 activated (1 mg/ml), or treated with ICAM2 beads or soluble ICAM-1, -2, or 3 (10 mg/ml, 30 min, 37° C.) before plating at $10^4$ target cells/well of a 96-well round bottom plate. CTLs were added at 50:1, 25:1, and 12.5:1 E:T ratio, and incubated at 37° C. for 4 hrs. Cells were then processed for multiparameter flow cytometry and intracellular perforin stain. Percent specific lysis was calculated by the following equation: % specific lysis=100−100×(experimental HL60 count/total control HL60 count). HL60 counts were detectable by the CFSE fluorescence. Percent perforin was calculated by the following equation: % perforin=100×[(experimental perforin MFI−isotype mAb MFI)/(total perforin MFI−isotype mAb MFI)]. MFI refers to mean fluorescent intensity of flow cytometric based intracellular detection. Cell conjugates were determined by flow cytometry as described (Morgan et al., 2001). Chemical inhibition was done at 10 mM of indicated compound (30 min, 37° C.) prior to stimulation as indicated. All experiments were performed in triplicate.

We claim:

1. A composition for determining the activation profile of one or more cells, the composition comprising:
    a sample comprising one or more cells;
    a first activation state specific binding member specific for an isoform corresponding to an activation state of a first activatable element, wherein the first activatable element comprises a first activation state and a second activation state; and
    a second activation state specific binding member specific for an isoform corresponding to an activation state of a second activatable element, wherein the second activatable element comprises a first activation state and a second activation state, and wherein the first and the second activatable elements are different and are distinguishably detectable from one another;
    wherein the first and second activation state specific binding members detect binding to their corresponding activatable elements simultaneously or sequentially in single cells bound to their corresponding activatable element inside the one or more cells and said binding indicates the activation profile of each of the one or more cells in the sample.

2. The composition according to claim 1, wherein the first and second activation state specific binding members are antibodies or binding fragments thereof.

3. The composition according to claim 1, wherein the first and second activation state specific binding members are labeled.

4. The composition according to claim 3, wherein the first and second activation state specific binding members are labeled with directly detectable label.

5. The composition according to claim 4, wherein the directly detectable label is a fluorescent label.

6. The composition according to claim 3, wherein the first and second activation state specific binding members are labeled with an indirectly detectable label.

7. The composition according to claim 6, wherein the indirectly detectable label is an enzyme.

8. The composition according to claim 1, wherein the composition further comprises an activator.

9. The composition according to claim 8, wherein the activator activates a signaling pathway.

10. The composition according to claim 8, wherein the binding element is selected from the group consisting of polypeptides, nucleic acids and small binding molecules.

11. The composition according to claim 1, wherein the composition is present in a vessel.

12. The composition according to claim 1, wherein the first activation state specific binding member is specific for a phosphorylation state of the first activatable element and the second activation state specific binding member is specific for a phosphorylation state of the second activatable element.

13. A system for determining the activation profile of one or more cells, the system comprising a multi-well plate comprising a well comprising:
   a sample comprising one or more cells, each of the one or more cells comprising:
      a first activation state specific binding member specific for an isoform corresponding to an activation state of a first activatable element, wherein the first activatable element comprises a first activation state and a second activation state; and
      a second activation state specific binding member specific for an isoform corresponding to an activation state of a second activatable element, wherein the second activatable element comprises a first activation state and a second activation state, and wherein the first and the second activatable elements are different and are distinguishably detectable from one another;
   wherein the first and second activation state specific binding members detect binding to their corresponding activatable elements simultaneously or sequentially in single cells bound to their corresponding activatable element inside the one or more cells and said binding indicates the activation profile of each of the one or more cells in the sample.

14. The system according to claim 13, wherein the multi-well plate is a 96-well plate.

15. The system according to claim 13, wherein the first and second activation state specific binding members are antibodies or binding fragments thereof.

16. The system according to claim 15, wherein the first and second activation state specific binding members are labeled.

17. The system according to claim 16, wherein the first and second activation state specific binding members are labeled with directly detectable label.

18. The system according to claim 17, wherein the directly detectable label is a fluorescent label.

19. The system according to claim 16, wherein the first and second activation state specific binding members are labeled with an indirectly detectable label.

20. The system according to claim 19, wherein the indirectly detectable label is an enzyme.

21. The system according to claim 13, wherein the well further comprises an activator.

22. The system according to claim 21, wherein the activator activates a signaling pathway.

23. The system according to claim 13, wherein the first activation state specific binding member is specific for a phosphorylation state of the first activatable element and the second activation state specific binding member is specific for a phosphorylation state of the second activatable element.

* * * * *